US012569237B2

(12) United States Patent
Jaramaz et al.

(10) Patent No.: US 12,569,237 B2
(45) Date of Patent: Mar. 10, 2026

(54) FORCE-INDICATING RETRACTOR DEVICE AND METHODS OF USE

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventors: Branislav Jaramaz, Pittsburgh, PA (US); Samuel C. Dumpe, Beaver, PA (US); Cedric Corpa De La Fuente, Gibsonia, PA (US); Gary David Carlson, Jr., Arlington, MA (US); Brett J. Bell, Pittsburgh, PA (US); Brian W. McKinnon, Arlington, TN (US); Daniel Farley, Memphis, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 880 days.

(21) Appl. No.: 17/266,712

(22) PCT Filed: Aug. 7, 2019

(86) PCT No.: PCT/US2019/045564
§ 371 (c)(1),
(2) Date: Feb. 8, 2021

(87) PCT Pub. No.: WO2020/033589
PCT Pub. Date: Feb. 13, 2020

(65) Prior Publication Data
US 2021/0298734 A1 Sep. 30, 2021

Related U.S. Application Data

(60) Provisional application No. 62/875,049, filed on Jul. 17, 2019, provisional application No. 62/844,451, (Continued)

(51) Int. Cl.
*A61B 17/02* (2006.01)
*A61B 34/30* (2016.01)
(Continued)

(52) U.S. Cl.
CPC ............ *A61B 17/025* (2013.01); *A61B 34/30* (2016.02); *G16H 20/40* (2018.01); *G16H 30/20* (2018.01);
(Continued)

(58) Field of Classification Search
CPC ....... A61B 17/025; A61B 34/20; A61B 34/25; A61B 34/30; A61B 2090/064
See application file for complete search history.

(56) References Cited

U.S. PATENT DOCUMENTS 5,380,311 A 1/1995 Mikhail
5,380,331 A * 1/1995 Mikhail ................. A61B 17/02
606/86 R
(Continued)

FOREIGN PATENT DOCUMENTS

DE 202010000341 U1 6/2010
WO 2007024990 A2 3/2007

OTHER PUBLICATIONS

European Patent Office, Examination Report, dated Jun. 26, 2024; 7 pages.
(Continued)

*Primary Examiner* — Si Ming Ku
(74) *Attorney, Agent, or Firm* — KDW Firm PLLC

(57) ABSTRACT

Devices, systems, and methods for measuring a force applied to a joint during a surgical procedure are disclosed.
(Continued)

The device includes an insertion tool, a handle, and one or more force indicators. The insertion tool includes an insertion end and a base end. The one or more force indicators may be attached to the insertion tool and the handle. The insertion end of the device may be inserted into a joint during a surgical procedure and used to apply a force to the joint and/or measure the force using the one or more force indicators when the force is applied.

15 Claims, 37 Drawing Sheets

Related U.S. Application Data filed on May 7, 2019, provisional application No. 62/811,766, filed on Feb. 28, 2019, provisional application No. 62/792,246, filed on Jan. 14, 2019, provisional application No. 62/715,576, filed on Aug. 7, 2018.

(51) Int. Cl.

| | | |
|---|---|---|
| *G16H 20/40* | (2018.01) | |
| *G16H 30/20* | (2018.01) | |
| *A61B 17/00* | (2006.01) | |
| *A61B 34/20* | (2016.01) | |
| *A61B 90/00* | (2016.01) | |

(52) U.S. Cl.

CPC ............... *A61B 2017/00115* (2013.01); *A61B 2017/00221* (2013.01); *A61B 2017/0268* (2013.01); *A61B 2034/2055* (2016.02); *A61B 2090/3945* (2016.02); *A61B 2090/397* (2016.02); *A61B 2562/0261* (2013.01)

(56) References Cited

U.S. PATENT DOCUMENTS

| | | | |
|---|---|---|---|
| 2009/0198240 A1 | 8/2009 | Kaufman | |
| 2011/0257655 A1 | 10/2011 | Copf, Jr. | |
| 2013/0274763 A1* | 10/2013 | Drapeau | A61B 17/1671 |
| | | | 606/132 |
| 2015/0342588 A1* | 12/2015 | Bechtold | A61B 17/025 |
| | | | 606/90 |
| 2018/0132839 A1* | 5/2018 | Friedrich | A61B 17/0206 |
| 2018/0333061 A1* | 11/2018 | Pracyk | A61B 5/24 |
| 2019/0388078 A1 | 12/2019 | Otto | |

OTHER PUBLICATIONS

European Patent Office, Examination Report, dated Sep. 30, 2024; 10 pages.

* cited by examiner

T + 1 minute

T + 0.5 minutes

T + 5 minutes

500F

515F

505F

530F

520F

535F

510F

1000B

1005B
INSERT DEVICE
INTO JOINT

1010B
BEND JOINT

1015B
MEASURE
FORCE APPLIED

1400

1415

1425C

1410

1420

1405

1425A

1425B

1425D

Determine First Vector Between Tracking Arrays — 1805

Apply Force to Tool — 1810

Determine Second Vector Between Tracking Arrays — 1815

Determine Deflection — 1820

Determine Applied Force — 1825

Provide Force Information to User — 1830

Receive Value(s) for Soft
Tissue Behavior Properties — 1905

Apply Force to Joint
Distraction Device — 1910

Determine Magnitude of
Force Applied to Joint
Distraction Device — 1915

Determine Ligament
Response Outputs — 1920

Determine Ligament
Tissue Properties — 1925

Provide or Revise Surgical
Plan — 1930

FORCE-INDICATING RETRACTOR DEVICE AND METHODS OF USE

CLAIM OF PRIORITY

This application is a U.S. National Stage filing under 35 U.S.C. § 371 of International PCT Application No. PCT/US2019/045564, filed Aug. 7, 2019, which claims the benefit of priority to U.S. Provisional Application No. 62/715,576, titled "FORCE-INDICATING RETRACTOR DEVICE AND METHODS OF USE," filed Aug. 7, 2018, U.S. Provisional Application No. 62/792,246, titled "FORCE-INDICATING RETRACTOR DEVICE AND METHODS OF USE," filed Jan. 14, 2019, U.S. Provisional Application No. 62/844,451, titled "FORCE-INDICATING RETRACTOR DEVICE AND METHODS OF USE," filed May 7, 2019, U.S. Provisional Application No. 62/811,766, titled "METHODS OF MEASURING FORCE USING A TRACKING SYSTEM," filed Feb. 28, 2019, and U.S. Provisional Application No. 62/875,049, titled "METHODS AND SYSTEMS FOR LIGAMENT BALANCING," filed Jul. 17, 2019, each of which is incorporated herein by reference in its entirety.

TECHNICAL FIELD

The present disclosure relates generally to methods, systems, and apparatuses related to a computer-assisted surgical system that includes various hardware and software components that work together to enhance surgical workflows. The disclosed techniques may be applied to, for example, shoulder, hip, and knee arthroplasties, as well as other surgical interventions such as arthroscopic procedures, spinal procedures, maxillofacial procedures, rotator cuff procedures, and ligament repair and replacement procedures.

BACKGROUND

The use of computers, robotics, and imaging to aid orthopedic surgery is known in the art. There has been a great deal of study and development of computer-aided navigation and robotic systems used to guide surgical procedures. For example, surgical navigation systems can aid surgeons in locating patient anatomical structures, guiding surgical instruments, and implanting medical devices with a high degree of accuracy. Surgical navigation systems often employ various forms of computing technology to perform a wide variety of standard and minimally invasive surgical procedures and techniques. Moreover, these systems allow surgeons to more accurately plan, track and navigate the placement of instruments and implants relative to the body of a patient, as well as conduct pre-operative and intra-operative body imaging.

Orthopedic implants are used for resurfacing or replacing joints, such as knees, hips, shoulders, ankles, and elbows that typically experience high levels of stress and wear or traumatic injury. Implants used to replace these joints must be strong and able to withstand the daily stress and wear at these joints, especially for weight-bearing knee and hip replacements. However, providing a sufficiently strong implant that also fits properly is challenging. Traditional orthopedic implants are made from polymer, ceramic, metal or other appropriate material and are formed so that they fit the patient's bone securely. In knee replacement surgeries, for example, typical approaches involve cutting the end of the tibia and/or femur, then fitting a new implant to the cut end. The size of the implant is typically determined by a surgeon based on hand measurements and visual estimates. The size and fit between the bone and implant can vary—in some cases the size and fit may be too loose, and in others cases, the size and fit may be too tight.

Robotically assisted total knee arthroplasty (TKA) provides a user with the ability to plan an implant surgical procedure and view a projected outcome prior to performing bone resection. In order to perform virtual planning, information regarding two physiological aspects of the patient's knee is required. Specifically, the virtual planning system requires (1) anatomical information pertaining to the patient's femur and tibia, and (2) information pertaining to the soft tissue tension/laxity within the joint. Obtaining information pertaining to the patient's femur and tibia (i.e., the bony anatomy) can be reliably performed in a number of ways whether pre-operatively or intraoperatively. However, the properties of the surrounding soft tissue are much less objective. The lack of objectivity in a major system input has the potential to lead to inconsistent results.

During a robotically assisted TKA, a user may be provided with an indication of the varus and valgus stress when the knee is moved through a range of motion. For example, a graphical user interface may display such measures to assist surgeons performing TKA procedures. Identifying the varus/valgus stress assists in quantifying the laxity of various ligaments and other soft tissues within the knee. However, the stress is typically applied manually or via a z-retractor placed between the medial and lateral tibiofemoral articular surfaces of the knee. As a result, quantifying ligament laxity in such a procedure is challenging because the amount of varus/valgus force applied to the knee is not standardized.

As such, devices and methods for standardizing the collection of soft tissue tension and/or laxity information in a joint, such as a knee, would be desirable.

SUMMARY

A device for use during a surgical procedure is provided. The device includes a tissue retractor, a handle, and one or more force indicators. The tissue retractor includes an insertion end and a base end. The insertion end of the tissue retractor is configured to be inserted between articular surfaces of a patient's joint. The base end of the tissue retractor is attached to the handle. The handle is configured to facilitate the application of a force to the device by a user, thereby distracting the joint when the insertion end of the tissue retractor is inserted between the femoral and tibial articular surfaces of the patient's knee.

According to certain embodiments, the articular surfaces of the patient's joint are the femoral and tibial articular surfaces of the patient's knee. In certain embodiments, the insertion end is configured to be inserted between a condyle of a femur and a corresponding condyle of a tibia of a knee of the patient. In certain embodiments, the insertion end is configured to be inserted between both condyles of a femur and both corresponding condyles of a tibia of a knee of the patient.

According to certain embodiments, the one or more force indicators are in electronic communication with a robotic surgical system. The electrical communication can be wired or wireless.

According to certain embodiments, the device includes a display in electronic communication with the one or more force indicators. In certain embodiments, the display is a digital display.

According to certain embodiments, the device includes one or more location tracking devices. In certain embodiments, the location tracking devices are optical tracking arrays. In certain embodiments, the one or more location tracking devices are in electronic communication with a robotic surgical system.

According to certain embodiments, the device includes a power supply cord. According to certain embodiments, the device includes a wireless power source. The wireless power source can include a fixed battery, a removable battery, a fluctuating magnetic field, a photovoltaic array, or any combination thereof.

According to certain embodiments, the one or more force indicators include one or more strain gauges located in the base end of the tissue retractor. The tissue retractor further includes a pivot feature located adjacent to the one or more strain gauges located in the base end of the tissue retractor and configured to concentrate the stress forces that result when a user applies a force to the device at the handle when the insertion end of the tissue retractor is inserted between the articular surfaces of the patient's joint at the location of the one or more strain gauges. The one or more strain gauges included in the base end of the tissue retractor measure the resulting stress forces as the user applies the force to the device at the handle. The distraction force can be estimated by using the stress forces measured by the one or more strain gauges included in the base end of the tissue retractor, and by assuming a location of a point of contact between the articular surfaces of a patient's joint and the insertion end of the tissue retractor when the user applies a force to the device at the handle. According to certain embodiments, the one or more strain gauges include a digital strain gauge.

According to certain embodiments, the one or more force indicators include one or more pressure sensors located in the insertion end of the tissue retractor. When the insertion end of the tissue retractor is inserted between the articular surfaces of a patient's joint, the one or more surface pressure sensors are configured to measure the pressure forces that result when a user applies a force to the device at the handle. The distraction force is estimated by using the stress forces measured by the one or more pressure sensors included on the insertion end of the tissue retractor and by the known location of the point of contact between the articular surfaces of the patient's joint and the insertion end of the tissue retractor when the user applies a force to the device at the handle. According to certain embodiments, the one or more surface pressure sensors include a piezo effect sensor.

According to certain embodiments, the device additionally includes one or more components of a tissue retractor each with an insertion end and a base end, and one or more handles arranged around a rotational joint. A rotational spring is wrapped around the rotational joint. The one or more force indicators include one or more electrical or magnetic contact sensors. When the insertion end of each of the one or more components of the tissue retractor is inserted between the articular surfaces of a patient's joint and a user applies a force to the one or more handles, the one or more components of the tissue retractor pivot around the rotational joint until the rotational spring reaches a displacement point at which a predetermined torque is achieved. The one or more electrical or magnetic sensors may be triggered when the handle reaches the displacement point at which the predetermined torque is achieved. According to certain embodiments, the one or more electrical or magnetic contact sensors include a piezo effect sensor, a Hall effect sensor, an inductive sensor, a microelectromechanical systems (MEMS) sensor, a piezo-resistive sensor, a load sensor, an ultrasonic resonator in conjunction with a compressible propagation structure, a capacitive sensor, and/or a temperature sensor.

According to certain embodiments, when a desired distraction force or displacement point is achieved, the robotic surgical system generates a signal to trigger the collection of location data from one or more location sensors located on a patient's tibia and/or femur.

According to certain embodiments, when a desired distraction force or displacement point is achieved, the robotic surgical system generates an alarm. The alarm can be visual, aural, or haptic.

A method of measuring forces applied to a joint using a surgical device is also provided. The method includes attaching a plurality of location tracking devices to a portion of a patient's body, inserting a device into a portion of a joint, applying a force onto a portion of the device and measuring the force applied to the device. In certain embodiments, the location tracking devices are optical tracking arrays. In certain embodiments, the device includes a tissue retractor, a handle, and one or more force indicators. The tissue retractor includes an insertion end and a base end. The insertion end of the tissue retractor is configured to be inserted between the femoral and tibial surfaces of a patient's knee. The base end of the tissue retractor is attached to the handle. The handle is configured to facilitate the application of a force onto a portion of a body.

In an alternative embodiment, the method includes attaching a plurality of location tracking devices to a portion of a patient's body, inserting a device into a portion of a joint, bending the joint, and measuring the force applied to the device.

According to certain embodiments, the plurality of location tracking devices attached to a portion of the patient's body are attached to the patient's tibia and femur. In certain embodiments, the plurality of location tracking devices are in electronic communication with a robotic surgical system. In certain embodiments, the electronic communication is wireless.

According to certain embodiments, each of the one or more force indicators is in electronic communication with a robotic surgical system. In certain embodiments, the electronic communication is wireless.

According to certain embodiments, the device further includes one or more location tracking devices in electronic communication with a robotic surgical system. In certain embodiments, the location tracking devices are optical tracking arrays. In certain embodiments, the electronic communication can be wireless.

In certain embodiments, location data from the one or more location tracking devices attached to the device is used to determine the directionality of the forces applied by the user onto the patient's body using the device. In certain embodiments, the directionality of the forces applied by the user onto the patient's body using the device is used to determine the kinematic properties of the portion of the patient's body at varying amounts of user-applied force.

According to certain embodiments, data from the plurality of location tracking devices attached to the portion of the patient's body is used to capture the position of the portion of the patient's body when the device is inserted into the portion of the joint and the force is applied to the portion of the patient's body. In certain embodiments, the data from the plurality of location tracking devices attached to the portion of the patient's body is used to capture the positions of the femur and tibia when the device is inserted into the portion of the joint and the force is applied to the portion of the patient's body. In certain embodiments, the positions of the femur and tibia are captured by the robotic surgical system. In certain embodiments, the positions of the femur and tibia are used to determine the flexion angle of the femur and tibia when the device is inserted into the portion of the joint and the force is applied to the portion of the patient's body. In certain embodiments, the data from the plurality of location tracking devices attached to the portion of the patient's body is used to capture the flexion angle of the femur and tibia when the device is inserted into the portion of the joint and the force is applied to the portion of the patient's body. In certain embodiments, the flexion angle is captured by the robotic surgical system.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Definitions

For the purposes of this disclosure, the term "implant" is used to refer to a prosthetic device or structure manufactured to replace or enhance a biological structure. For example, in a total hip replacement procedure a prosthetic acetabular cup (implant) is used to replace or enhance a patients worn or damaged acetabulum. While the term "implant" is generally considered to denote a man-made structure (as contrasted with a transplant), for the purposes of this specification an implant can include a biological tissue or material transplanted to replace or enhance a biological structure.

For the purposes of this disclosure, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

Although much of this disclosure refers to surgeons or other medical professionals by specific job title or role, nothing in this disclosure is intended to be limited to a specific job title or function. Surgeons or medical professionals can include any doctor, nurse, medical professional, or technician. Any of these terms or job titles can be used interchangeably with the user of the systems disclosed herein unless otherwise explicitly demarcated. For example, a reference to a surgeon could also apply, in some embodiments to a technician or nurse.

CASS Ecosystem Overview

Figure 1:
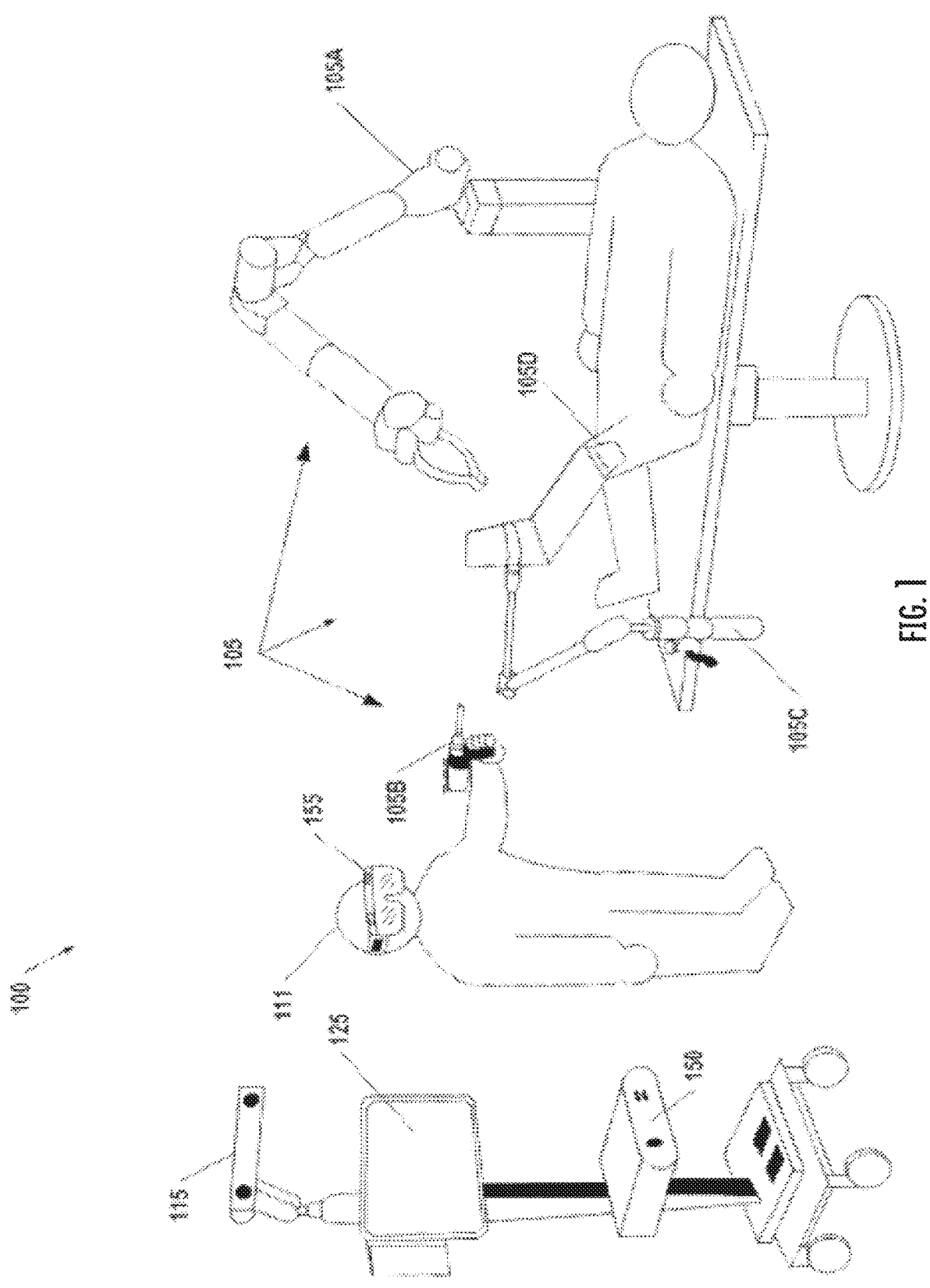
FIG. 1 depicts an operating theatre including an illustrative computer-assisted surgical system (CASS) in accordance with an embodiment.

FIG. 1 provides an illustration of an example computer-assisted surgical system (CASS) 100, according to some embodiments. As described in further detail in the sections that follow; the CASS uses computers, robotics, and imaging technology to aid surgeons in performing orthopedic surgery procedures such as total knee arthroplasty (TKA) or total hip arthroplasty (THA). For example, surgical navigation systems can aid surgeons in locating patient anatomical structures, guiding surgical instruments, and implanting medical devices with a high degree of accuracy. Surgical navigation systems such as the CASS 100 often employ various forms of computing technology to perform a wide variety of standard and minimally invasive surgical procedures and techniques. Moreover, these systems allow surgeons to more accurately plan, track and navigate the placement of instruments and implants relative to the body of a patient, as well as conduct pre-operative and intra-operative body imaging.

An Effector Platform 105 positions surgical tools relative to a patient during surgery. The exact components of the Effector Platform 105 will vary, depending on the embodiment employed. For example, for a knee surgery, the Effector Platform 105 may include an End Effector 105B that holds surgical tools or instruments during their use. The End Effector 105B may be a handheld device or instrument used by the surgeon (e.g., a NAVIO® hand piece or a cutting guide or jig) or, alternatively, the End Effector 105B can include a device or instrument held or positioned by a Robotic Arm 105A.

The Effector Platform 105 can include a Limb Positioner 105C for positioning the patient's limbs during surgery. One example of a Limb Positioner 105C is the SMITH AND NEPHEW SPIDER2 system. The Limb Positioner 105C may be operated manually by the surgeon or alternatively change limb positions based on instructions received from the Surgical Computer 150 (described below).

Resection Equipment 110 (not shown in FIG. 1) performs bone or tissue resection using, for example, mechanical, ultrasonic, or laser techniques. Examples of Resection Equipment 110 include drilling devices, burring devices, oscillatory sawing devices, vibratory impaction devices, reamers, ultrasonic bone cutting devices, radio frequency ablation devices, and laser ablation systems. In some embodiments, the Resection Equipment 110 is held and operated by the surgeon during surgery. In other embodiments, the Effector Platform 105 may be used to hold the Resection Equipment 110 during use.

The Effector Platform 105 can also include a cutting guide or jig 105D that is used to guide saws or drills used to resect tissue during surgery. Such cutting guides 105D can be formed integrally as part of the Effector Platform 105 or Robotic Arm 105A, or cutting guides can be separate structures that can be matingly and/or removably attached to the Effector Platform 105 or Robotic Arm 105A. The Effector Platform 105 or Robotic Arm 105A can be controlled by the CASS 100 to position a cutting guide or jig 105D adjacent to the patient's anatomy in accordance with a pre-operatively or intraoperatively developed surgical plan such that the cutting guide or jig will produce a precise bone cut in accordance with the surgical plan.

The Tracking System 115 uses one or more sensors to collect real-time position data that locates the patient's anatomy and surgical instruments. For example, for TKA procedures, the Tracking System may provide a location and orientation of the End Effector 105B during the procedure. In addition to positional data, data from the Tracking System 115 can also be used to infer velocity/acceleration of anatomy/instrumentation, which can be used for tool control. In some embodiments, the Tracking System 115 may use a tracker array attached to the End Effector 105B to determine the location and orientation of the End Effector 105B. The position of the End Effector 105B may be inferred based on the position and orientation of the Tracking System 115 and a known relationship in three-dimensional space between the Tracking System 115 and the End Effector 105B. Various types of tracking systems may be used in various embodiments of the present invention including, without limitation, Infrared (IR) tracking systems, electromagnetic (EM) tracking systems, video or image based tracking systems, and ultrasound registration and tracking systems.

Any suitable tracking system can be used for tracking surgical objects and patient anatomy in the surgical theatre. For example, a combination of IR and visible light cameras can be used in an array. Various illumination sources, such as an IR LED light source, can illuminate the scene allowing three-dimensional imaging to occur. In some embodiments, this can include stereoscopic, tri-scopic, quad-scopic, etc. imaging. In addition to the camera array, which in some embodiments is affixed to a cart, additional cameras can be placed throughout the surgical theatre. For example, handheld tools or headsets worn by operators/surgeons can include imaging capability that communicates images back to a central processor to correlate those images with images captured by the camera array. This can give a more robust image of the environment for modeling using multiple perspectives. Furthermore, some imaging devices may be of suitable resolution or have a suitable perspective on the scene to pick up information stored in quick response (QR) codes or barcodes. This can be helpful in identifying specific objects not manually registered with the system.

In some embodiments, specific objects can be manually registered by a surgeon with the system preoperatively or intraoperatively. For example, by interacting with a user interface, a surgeon may identify the starting location for a tool or a bone structure. By tracking fiducial marks associated with that tool or bone structure, or by using other conventional image tracking modalities, a processor may track that tool or bone as it moves through the environment in a three-dimensional model.

In some embodiments, certain markers, such as fiducial marks that identify individuals, important tools, or bones in the theater may include passive or active identifiers that can be picked up by a camera or camera array associated with the tracking system. For example, an IR LED can flash a pattern that conveys a unique identifier to the source of that pattern, providing a dynamic identification mark. Similarly, one or two dimensional optical codes (barcode, QR code, etc.) can be affixed to objects in the theater to provide passive identification that can occur based on image analysis. If these codes are placed asymmetrically on an object, they can also be used to determine an orientation of an object by comparing the location of the identifier with the extents of an object in an image. For example, a QR code may be placed in a corner of a tool tray, allowing the orientation and identity of that tray to be tracked. Other tracking modalities are explained throughout. For example, in some embodiments, augmented reality headsets can be worn by surgeons and other staff to provide additional camera angles and tracking capabilities.

In addition to optical tracking, certain features of objects can be tracked by registering physical properties of the object and associating them with objects that can be tracked, such as fiducial marks fixed to a tool or bone. For example, a surgeon may perform a manual registration process whereby a tracked tool and a tracked bone can be manipulated relative to one another. By impinging the tip of the tool against the surface of the bone, a three-dimensional surface can be mapped for that bone that is associated with a position and orientation relative to the frame of reference of that fiducial mark. By optically tracking the position and orientation (pose) of the fiducial mark associated with that bone, a model of that surface can be tracked with an environment through extrapolation.

The registration process that registers the CASS 100 to the relevant anatomy of the patient can also involve the use of anatomical landmarks, such as landmarks on a bone or cartilage. For example, the CASS 100 can include a 3D model of the relevant bone or joint and the surgeon can intraoperatively collect data regarding the location of bony landmarks on the patient's actual bone using a probe that is connected to the CASS. Bony landmarks can include, for example, the medial malleolus and lateral malleolus, the ends of the proximal femur and distal tibia, and the center of the hip joint. The CASS 100 can compare and register the location data of bony landmarks collected by the surgeon with the probe with the location data of the same landmarks in the 3D model. Alternatively, the CASS 100 can construct a 3D model of the bone or joint without pre-operative image data by using location data of bony landmarks and the bone surface that are collected by the surgeon using a CASS probe or other means. The registration process can also include determining various axes of a joint. For example, for a TKA the surgeon can use the CASS 100 to determine the anatomical and mechanical axes of the femur and tibia. The surgeon and the CASS 100 can identify the center of the hip joint by moving the patient's leg in a spiral direction (i.e., circumduction) so the CASS can determine where the center of the hip joint is located.

A Tissue Navigation System 120 (not shown in FIG. 1) provides the surgeon with intraoperative, real-time visualization for the patient's bone, cartilage, muscle, nervous, and/or vascular tissues surrounding the surgical area. Examples of systems that may be employed for tissue navigation include fluorescent imaging systems and ultrasound systems.

The Display 125 provides graphical user interfaces (GUIs) that display images collected by the Tissue Navigation System 120 as well other information relevant to the surgery. For example, in one embodiment, the Display 125 overlays image information collected from various modalities (e.g., CT, MRI, X-ray, fluorescent, ultrasound, etc.) collected pre-operatively or intra-operatively to give the surgeon various views of the patient's anatomy as well as real-time conditions. The Display 125 may include, for example, one or more computer monitors. As an alternative or supplement to the Display 125, one or more members of the surgical staff may wear an Augmented Reality (AR) Head Mounted Device (HMD). For example, in FIG. 1 the Surgeon 111 is wearing an AR HMD 155 that may, for example, overlay pre-operative image data on the patient or provide surgical planning suggestions. Various example uses of the AR HMD 155 in surgical procedures are detailed in the sections that follow.

Surgical Computer 150 provides control instructions to various components of the CASS 100, collects data from those components, and provides general processing for various data needed during surgery. In some embodiments, the Surgical Computer 150 is a general purpose computer. In other embodiments, the Surgical Computer 150 may be a parallel computing platform that uses multiple central processing units (CPUs) or graphics processing units (GPU) to perform processing. In some embodiments, the Surgical Computer 150 is connected to a remote server over one or more computer networks (e.g., the Internet). The remote server can be used, for example, for storage of data or execution of computationally intensive processing tasks.

Various techniques generally known in the art can be used for connecting the Surgical Computer 150 to the other components of the CASS 100. Moreover, the computers can connect to the Surgical Computer 150 using a mix of technologies. For example, the End Effector 105B may connect to the Surgical Computer 150 over a wired (i.e., serial) connection. The Tracking System 115, Tissue Navigation System 120, and Display 125 can similarly be connected to the Surgical Computer 150 using wired connections. Alternatively, the Tracking System 115, Tissue Navigation System 120, and Display 125 may connect to the Surgical Computer 150 using wireless technologies such as, without limitation, Wi-Fi, Bluetooth, Near Field Communication (NFC), or ZigBee.

Powered Impaction and Acetabular Reamer Devices

Part of the flexibility of the CASS design described above with respect to FIG. 1 is that additional or alternative devices can be added to the CASS 100 as necessary to support particular surgical procedures. For example, in the context of hip surgeries, the CASS 100 may include a powered impaction device. Impaction devices are designed to repeatedly apply an impaction force that the surgeon can use to perform activities such as implant alignment. For example, within a total hip arthroplasty (THA), a surgeon will often insert a prosthetic acetabular cup into the implant host's acetabulum using an impaction device. Although impaction devices can be manual in nature (e.g., operated by the surgeon striking an impactor with a mallet), powered impaction devices are generally easier and quicker to use in the surgical setting. Powered impaction devices may be powered, for example, using a battery attached to the device. Various attachment pieces may be connected to the powered impaction device to allow the impaction force to be directed in various ways as needed during surgery. Also in the context of hip surgeries, the CASS 100 may include a powered, robotically controlled end effector to ream the acetabulum to accommodate an acetabular cup implant.

In a robotically-assisted THA, the patient's anatomy can be registered to the CASS 100 using CT or other image data, the identification of anatomical landmarks, tracker arrays attached to the patient's bones, and one or more cameras. Tracker arrays can be mounted on the iliac crest using clamps and/or bone pins and such trackers can be mounted externally through the skin or internally (either posterolaterally or anterolaterally) through the incision made to perform the THA. For a THA, the CASS 100 can utilize one or more femoral cortical screws inserted into the proximal femur as checkpoints to aid in the registration process. The CASS 100 can also utilize one or more checkpoint screws inserted into the pelvis as additional checkpoints to aid in the registration process. Femoral tracker arrays can be secured to or mounted in the femoral cortical screws. The CASS 100 can employ steps where the registration is verified using a probe that the surgeon precisely places on key areas of the proximal femur and pelvis identified for the surgeon on the display 125. Trackers can be located on the robotic arm 105A or end effector 105B to register the arm and/or end effector to the CASS 100. The verification step can also utilize proximal and distal femoral checkpoints. The CASS 100 can utilize color prompts or other prompts to inform the surgeon that the registration process for the relevant bones and the robotic arm 105A or end effector 105B has been verified to a certain degree of accuracy (e.g., within 1 mm).

For a THA, the CASS 100 can include a broach tracking option using femoral arrays to allow the surgeon to intraoperatively capture the broach position and orientation and calculate hip length and offset values for the patient. Based on information provided about the patient's hip joint and the planned implant position and orientation after broach tracking is completed, the surgeon can make modifications or adjustments to the surgical plan.

For a robotically-assisted THA, the CASS 100 can include one or more powered reamers connected or attached to a robotic arm 105A or end effector 105B that prepares the pelvic bone to receive an acetabular implant according to a surgical plan. The robotic arm 105A and/or end effector 105B can inform the surgeon and/or control the power of the reamer to ensure that the acetabulum is being resected (reamed) in accordance with the surgical plan. For example, if the surgeon attempts to resect bone outside of the boundary of the bone to be resected in accordance with the surgical plan, the CASS 100 can power off the reamer or instruct the surgeon to power off the reamer. The CASS 100 can provide the surgeon with an option to turn off or disengage the robotic control of the reamer. The display 125 can depict the progress of the bone being resected (reamed) as compared to the surgical plan using different colors. The surgeon can view the display of the bone being resected (reamed) to guide the reamer to complete the reaming in accordance with the surgical plan. The CASS 100 can provide visual or audible prompts to the surgeon to warn the surgeon that resections are being made that are not in accordance with the surgical plan.

Following reaming, the CASS 100 can employ a manual or powered impactor that is attached or connected to the robotic arm 105A or end effector 105B to impact trial implants and final implants into the acetabulum. The robotic arm 105A and/or end effector 105B can be used to guide the impactor to impact the trial and final implants into the acetabulum in accordance with the surgical plan. The CASS 100 can cause the position and orientation of the trial and final implants vis-à-vis the bone to be displayed to inform the surgeon as to how the trial and final implant's orientation and position compare to the surgical plan, and the display 125 can show the implant's position and orientation as the surgeon manipulates the leg and hip. The CASS 100 can provide the surgeon with the option of re-planning and re-doing the reaming and implant impaction by preparing a new surgical plan if the surgeon is not satisfied with the original implant position and orientation.

Preoperatively, the CASS 100 can develop a proposed surgical plan based on a three dimensional model of the hip joint and other information specific to the patient, such as the mechanical and anatomical axes of the leg bones, the epicondylar axis, the femoral neck axis, the dimensions (e.g., length) of the femur and hip, the midline axis of the hip joint, the ASIS axis of the hip joint, and the location of anatomical landmarks such as the lesser trochanter landmarks, the distal landmark, and the center of rotation of the hip joint. The CASS-developed surgical plan can provide a recommended optimal implant size and implant position and orientation based on the three dimensional model of the hip joint and other information specific to the patient. The CASS-developed surgical plan can include proposed details on offset values, inclination and anteversion values, center of rotation, cup size, medialization values, superior-inferior fit values, femoral stem sizing and length.

For a THA, the CASS-developed surgical plan can be viewed preoperatively and intraoperatively, and the surgeon can modify CASS-developed surgical plan preoperatively or intraoperatively. The CASS-developed surgical plan can display the planned resection to the hip joint and superimpose the planned implants onto the hip joint based on the planned resections. The CASS 100 can provide the surgeon with options for different surgical workflows that will be displayed to the surgeon based on a surgeon's preference. For example, the surgeon can choose from different workflows based on the number and types of anatomical landmarks that are checked and captured and/or the location and number of tracker arrays used in the registration process.

According to some embodiments, a powered impaction device used with the CASS 100 may operate with a variety of different settings. In some embodiments, the surgeon adjusts settings through a manual switch or other physical mechanism on the powered impaction device. In other embodiments, a digital interface may be used that allows setting entry, for example, via a touchscreen on the powered impaction device. Such a digital interface may allow the available settings to vary based, for example, on the type of attachment piece connected to the power attachment device. In some embodiments, rather than adjusting the settings on the powered impaction device itself, the settings can be changed through communication with a robot or other computer system within the CASS 100. Such connections may be established using, for example, a Bluetooth or Wi-Fi networking module on the powered impaction device. In another embodiment, the impaction device and end pieces may contain features that allow the impaction device to be aware of what end piece (cup impactor, broach handle, etc.) is attached with no action required by the surgeon, and adjust the settings accordingly. This may be achieved, for example, through a QR code, barcode. RFID tag, or other method.

Examples of the settings that may be used include cup impaction settings (e.g., single direction, specified frequency range, specified force and/or energy range); broach impaction settings (e.g., dual direction/oscillating at a specified frequency range, specified force and/or energy range); femoral head impaction settings (e.g., single direction/single blow at a specified force or energy); and stem impaction settings (e.g., single direction at specified frequency with a specified force or energy). Additionally, in some embodiments, the powered impaction device includes settings related to acetabular liner impaction (e.g., single direction/single blow at a specified force or energy). There may be a plurality of settings for each type of liner such as poly, ceramic, oxinium, or other materials. Furthermore, the powered impaction device may offer settings for different bone quality based on preoperative testing/imaging/knowledge and/or intraoperative assessment by surgeon.

In some embodiments, the powered impaction device includes feedback sensors that gather data during instrument use, and send data to a computing device such as a controller within the device or the Surgical Computer 150. This computing device can then record the data for later analysis and use. Examples of the data that may be collected include, without limitation, sound waves, the predetermined resonance frequency of each instrument, reaction force or rebound energy from patient bone, location of the device with respect to imaging (e.g., fluoro, CT, ultrasound, MRI, etc.) registered bony anatomy, and/or external strain gauges on bones.

Once the data is collected, the computing device may execute one or more algorithms in real-time or near real-time to aid the surgeon in performing the surgical procedure. For example, in some embodiments, the computing device uses the collected data to derive information such as the proper final broach size (femur); when the stem is fully seated (femur side); or when the cup is seated (depth and/or orientation) for a THA. Once the information is known, it may be displayed for the surgeon's review, or it may be used to activate haptics or other feedback mechanisms to guide the surgical procedure.

Additionally, the data derived from the aforementioned algorithms may be used to drive operation of the device. For example, during insertion of a prosthetic acetabular cup with a powered impaction device, the device may automatically extend an impaction head (e.g., an end effector) moving the implant into the proper location, or turn the power off to the device once the implant is fully seated. In one embodiment, the derived information may be used to automatically adjust settings for quality of bone where the powered impaction device should use less power to mitigate femoral/acetabular/pelvic fracture or damage to surrounding tissues.

Robotic Arm

In some embodiments, the CASS 100 includes a robotic arm 105A that serves as an interface to stabilize and hold a variety of instruments used during the surgical procedure. For example, in the context of a hip surgery, these instruments may include, without limitation, retractors, a sagittal or reciprocating saw, the reamer handle, the cup impactor, the broach handle, and the stem inserter. The robotic arm 105A may have multiple degrees of freedom (like a Spider device), and have the ability to be locked in place (e.g., by a press of a button, voice activation, a surgeon removing a hand from the robotic arm, or other method).

In some embodiments, movement of the robotic arm 105A may be effectuated by use of a control panel built into the robotic arm system. For example, a display screen may include one or more input sources, such as physical buttons or a user interface having one or more icons, that direct movement of the robotic arm 105A. The surgeon or other healthcare professional may engage with the one or more input sources to position the robotic arm 105A when performing a surgical procedure.

A tool or an end effector 105B attached or integrated into a robotic arm 105A may include, without limitation, a burring device, a scalpel, a cutting device, a retractor, a joint tensioning device, or the like. In embodiments in which an end effector 105B is used, the end effector may be positioned at the end of the robotic arm 105A such that any motor control operations are performed within the robotic arm system. In embodiments in which a tool is used, the tool may be secured at a distal end of the robotic arm 105A, but motor control operation may reside within the tool itself.

The robotic arm 105A may be motorized internally to both stabilize the robotic arm, thereby preventing it from falling and hitting the patient, surgical table, surgical staff, etc., and to allow the surgeon to move the robotic arm without having to fully support its weight. While the surgeon is moving the robotic arm 105A, the robotic arm may provide some resistance to prevent the robotic arm from moving too fast or having too many degrees of freedom active at once. The position and the lock status of the robotic arm 105A may be tracked, for example, by a controller or the Surgical Computer 150.

In some embodiments, the robotic arm 105A can be moved by hand (e.g., by the surgeon) or with internal motors into its ideal position and orientation for the task being performed. In some embodiments, the robotic arm 105A may be enabled to operate in a "free" mode that allows the surgeon to position the arm into a desired position without being restricted. While in the free mode, the position and orientation of the robotic arm 105A may still be tracked as described above. In one embodiment, certain degrees of freedom can be selectively released upon input from user (e.g., surgeon) during specified portions of the surgical plan tracked by the Surgical Computer 150. Designs in which a robotic arm 105A is internally powered through hydraulics or motors or provides resistance to external manual motion through similar means can be described as powered robotic arms, while arms that are manually manipulated without power feedback, but which may be manually or automatically locked in place, may be described as passive robotic arms.

A robotic arm 105A or end effector 105B can include a trigger or other means to control the power of a saw or drill. Engagement of the trigger or other means by the surgeon can cause the robotic arm 105A or end effector 105B to transition from a motorized alignment mode to a mode where the saw or drill is engaged and powered on. Additionally, the CASS 100 can include a foot pedal (not shown) that causes the system to perform certain functions when activated. For example, the surgeon can activate the foot pedal to instruct the CASS 100 to place the robotic arm 105A or end effector 105B in an automatic mode that brings the robotic arm or end effector into the proper position with respect to the patient's anatomy in order to perform the necessary resections. The CASS 100 can also place the robotic arm 105A or end effector 105B in a collaborative mode that allows the surgeon to manually manipulate and position the robotic arm or end effector into a particular location. The collaborative mode can be configured to allow the surgeon to move the robotic arm 105A or end effector 105B medially or laterally, while restricting movement in other directions. As discussed, the robotic arm 105A or end effector 105B can include a cutting device (saw; drill, and burr) or a cutting guide or jig 105D that will guide a cutting device. In other embodiments, movement of the robotic arm 105A or robotically controlled end effector 105B can be controlled entirely by the CASS 100 without any, or with only minimal, assistance or input from a surgeon or other medical professional. In still other embodiments, the movement of the robotic arm 105A or robotically controlled end effector 105B can be controlled remotely by a surgeon or other medical professional using a control mechanism separate from the robotic arm or robotically controlled end effector device, for example using a joystick or interactive monitor or display control device.

The examples below describe uses of the robotic device in the context of a hip surgery: however, it should be understood that the robotic arm may have other applications for surgical procedures involving knees, shoulders, etc. One example of use of a robotic arm in the context of forming an anterior cruciate ligament (ACL) graft tunnel is described in U.S. Provisional Patent Application No. 62/723,898 filed Aug. 28, 2018 and entitled "Robotic Assisted Ligament Graft Placement and Tensioning," the entirety of which is incorporated herein by reference.

A robotic arm 105A may be used for holding the retractor. For example in one embodiment, the robotic arm 105A may be moved into the desired position by the surgeon. At that point, the robotic arm 105A may lock into place. In some embodiments, the robotic arm 105A is provided with data regarding the patient's position, such that if the patient moves, the robotic arm can adjust the retractor position accordingly. In some embodiments, multiple robotic arms may be used, thereby allowing multiple retractors to be held or for more than one activity to be performed simultaneously (e.g., retractor holding & reaming).

The robotic arm 105A may also be used to help stabilize the surgeon's hand while making a femoral neck cut. In this application, control of the robotic arm 105A may impose certain restrictions to prevent soft tissue damage from occurring. For example, in one embodiment, the Surgical Computer 150 tracks the position of the robotic arm 105A as it operates. If the tracked location approaches an area where tissue damage is predicted, a command may be sent to the robotic arm 105A causing it to stop. Alternatively, where the robotic arm 105A is automatically controlled by the Surgical Computer 150, the Surgical Computer may ensure that the robotic arm is not provided with any instructions that cause it to enter areas where soft tissue damage is likely to occur. The Surgical Computer 150 may impose certain restrictions on the surgeon to prevent the surgeon from reaming too far into the medial wall of the acetabulum or reaming at an incorrect angle or orientation.

In some embodiments, the robotic arm 105A may be used to hold a cup impactor at a desired angle or orientation during cup impaction. When the final position has been achieved, the robotic arm 105A may prevent any further seating to prevent damage to the pelvis.

The surgeon may use the robotic arm 105A to position the broach handle at the desired position and allow the surgeon to impact the broach into the femoral canal at the desired orientation. In some embodiments, once the Surgical Computer 150 receives feedback that the broach is fully seated, the robotic arm 105A may restrict the handle to prevent further advancement of the broach.

The robotic arm 105A may also be used for resurfacing applications. For example, the robotic arm 105A may stabilize the surgeon while using traditional instrumentation and provide certain restrictions or limitations to allow for proper placement of implant components (e.g., guide wire placement, chamfer cutter, sleeve cutter, plan cutter, etc.). Where only a burr is employed, the robotic arm 105A may stabilize the surgeon's handpiece and may impose restrictions on the handpiece to prevent the surgeon from removing unintended bone in contravention of the surgical plan.

Surgical Procedure Data Generation and Collection

The various services that are provided by medical professionals to treat a clinical condition are collectively referred to as an "episode of care." For a particular surgical intervention the episode of care can include three phases: pre-operative, intra-operative, and post-operative. During each phase, data is collected or generated that can be used to analyze the episode of care in order to understand various aspects of the procedure and identify patterns that may be used, for example, in training models to make decisions with minimal human intervention. The data collected over the episode of care may be stored at the Surgical Computer 150 or the Surgical Data Server 180 as a complete dataset. Thus, for each episode of care, a dataset exists that comprises all of the data collectively pre-operatively about the patient, all of the data collected or stored by the CASS 100 intra-operatively, and any post-operative data provided by the patient or by a healthcare professional monitoring the patient.

As explained in further detail, the data collected during the episode of care may be used to enhance performance of the surgical procedure or to provide a holistic understanding of the surgical procedure and the patient outcomes. For example, in some embodiments, the data collected over the episode of care may be used to generate a surgical plan. In one embodiment, a high-level, pre-operative plan is refined intra-operatively as data is collected during surgery. In this way, the surgical plan can be viewed as dynamically changing in real-time or near real-time as new data is collected by the components of the CASS 100. In other embodiments, pre-operative images or other input data may be used to develop a robust plan preoperatively that is simply executed during surgery. In this case, the data collected by the CASS 100 during surgery may be used to make recommendations that ensure that the surgeon stays within the pre-operative surgical plan. For example, if the surgeon is unsure how to achieve a certain prescribed cut or implant alignment, the Surgical Computer 150 can be queried for a recommendation. In still other embodiments, the pre-operative and intra-operative planning approaches can be combined such that a robust pre-operative plan can be dynamically modified, as necessary or desired, during the surgical procedure. In some embodiments, a biomechanics-based model of patient anatomy contributes simulation data to be considered by the CASS 100 in developing preoperative, intraoperative, and post-operative/rehabilitation procedures to optimize implant performance outcomes for the patient.

Aside from changing the surgical procedure itself, the data gathered during the episode of care may be used as an input to other procedures ancillary to the surgery. For example, in some embodiments, implants can be designed using episode of care data. Example data-driven techniques for designing, sizing, and fitting implants are described in U.S. patent application Ser. No. 13/814,531 filed Aug. 15, 2011 and entitled "Systems and Methods for Optimizing Parameters for Orthopaedic Procedures"; U.S. patent application Ser. No. 14/232,958 filed Jul. 20, 2012 and entitled "Systems and Methods for Optimizing Fit of an Implant to Anatomy"; and U.S. patent application Ser. No. 12/234,444 filed Sep. 19, 2008 and entitled "Operatively Tuning Implants for Increased Performance," the entire contents of each of which are hereby incorporated by reference into this patent application.

Furthermore, the data can be used for educational, training, or research purposes. For example, using the network-based approach described below in FIG. 2C, other doctors or students can remotely view surgeries in interfaces that allow them to selectively view data as it is collected from the various components of the CASS 100. After the surgical procedure, similar interfaces may be used to "playback" a surgery for training or other educational purposes, or to identify the source of any issues or complications with the procedure.

Data acquired during the pre-operative phase generally includes all information collected or generated prior to the surgery. Thus, for example, information about the patient may be acquired from a patient intake form or electronic medical record (EMR). Examples of patient information that may be collected include, without limitation, patient demographics, diagnoses, medical histories, progress notes, vital signs, medical history information, allergies, and lab results. The pre-operative data may also include images related to the anatomical area of interest. These images may be captured, for example, using Magnetic Resonance Imaging (MRI), Computed Tomography (CT), X-ray, ultrasound, or any other modality known in the art. The pre-operative data may also comprise quality of life data captured from the patient. For example, in one embodiment, pre-surgery patients use a mobile application ("app") to answer questionnaires regarding their current quality of life. In some embodiments, preoperative data used by the CASS 100 includes demographic, anthropometric, cultural, or other specific traits about a patient that can coincide with activity levels and specific patient activities to customize the surgical plan to the patient. For example, certain cultures or demographics may be more likely to use a toilet that requires squatting on a daily basis.

Figure 2A:
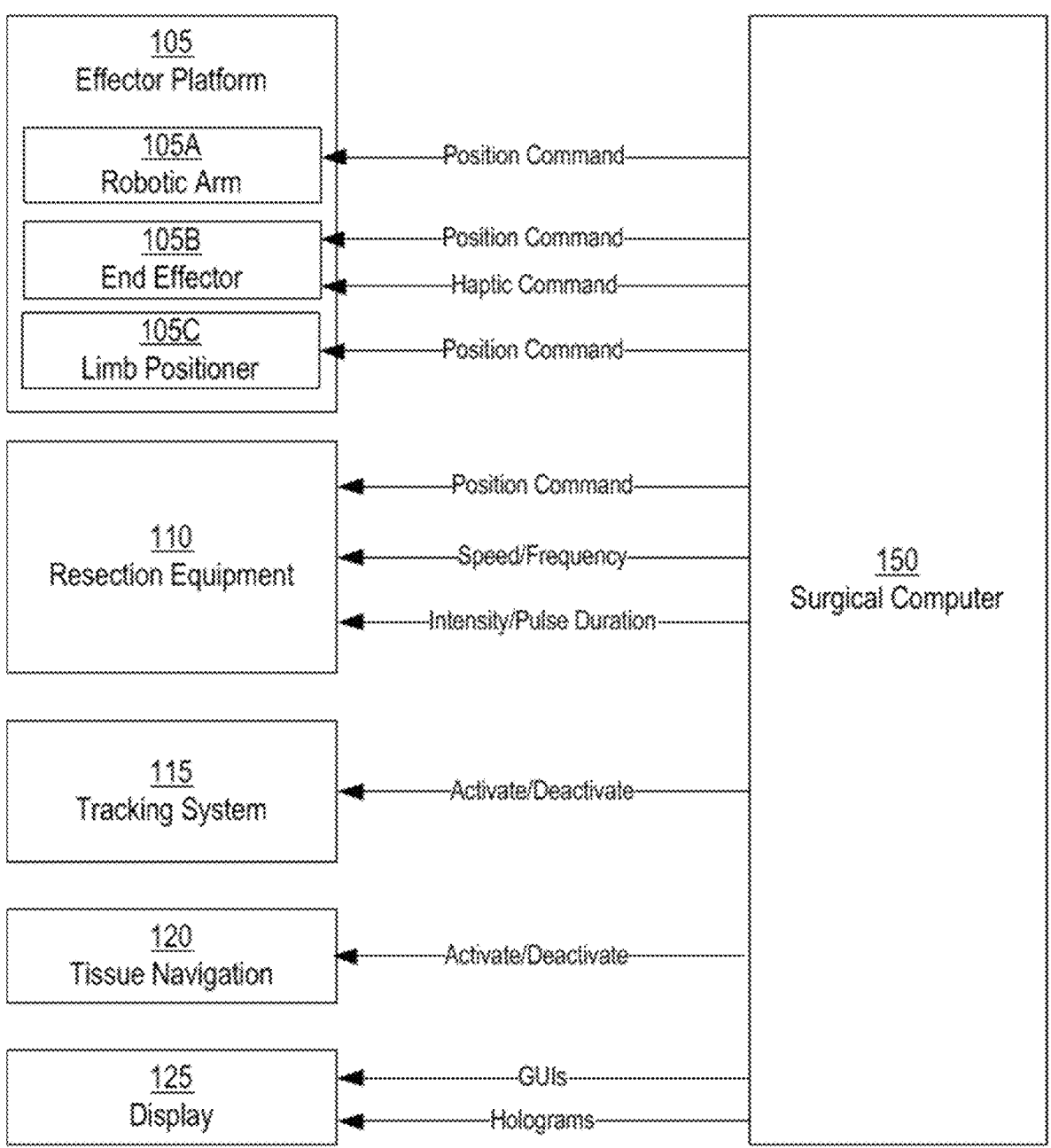
FIG. 2A depicts illustrative control instructions that a surgical computer provides to other components of a CASS in accordance with an embodiment.
Figure 2B:
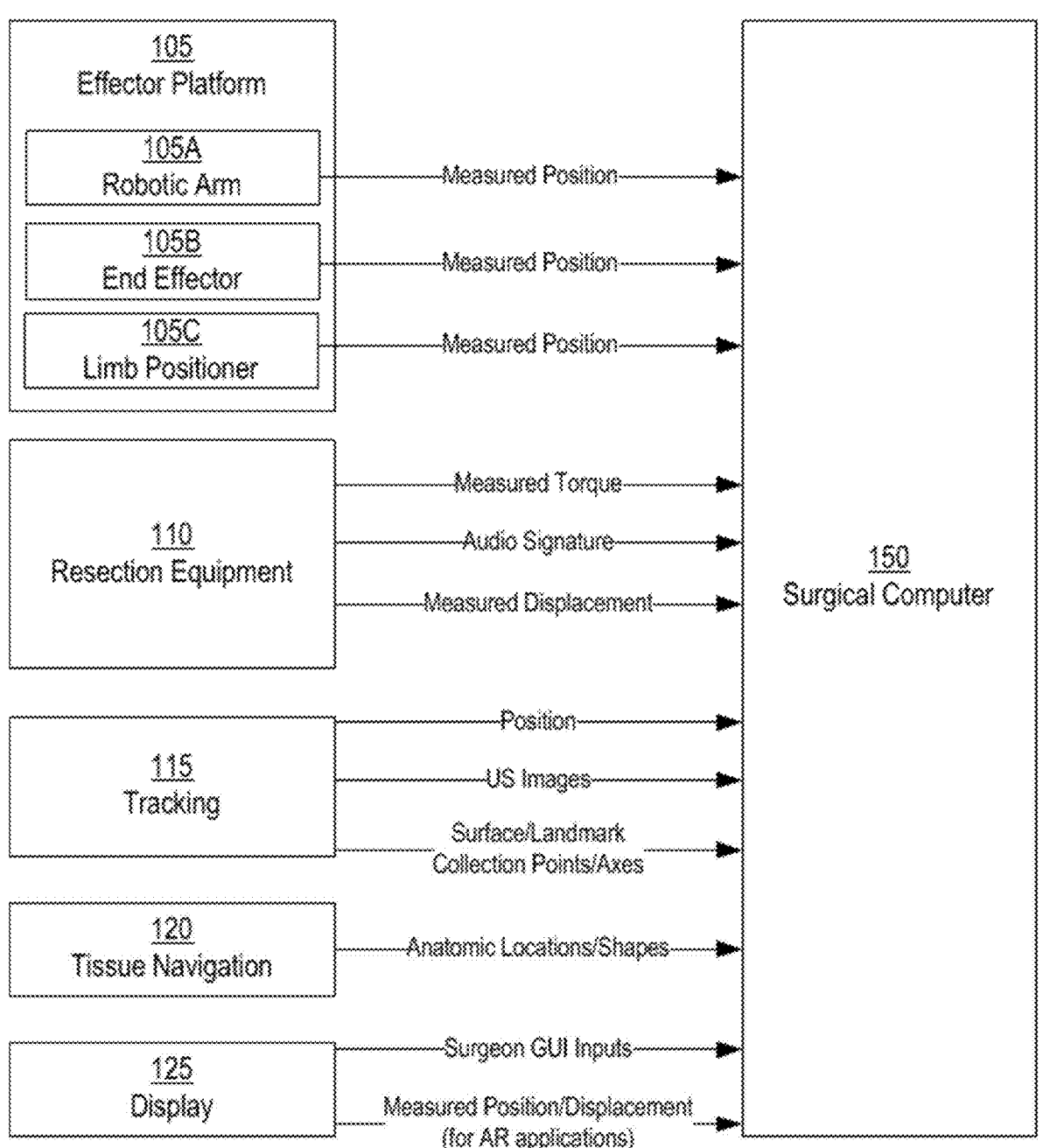
FIG. 2B depicts illustrative control instructions that components of a CASS provide to a surgical computer in accordance with an embodiment.

FIGS. 2A and 2B provide examples of data that may be acquired during the intra-operative phase of an episode of care. These examples are based on the various components of the CASS 100 described above with reference to FIG. 1; however, it should be understood that other types of data may be used based on the types of equipment used during surgery and their use.

FIG. 2A shows examples of some of the control instructions that the Surgical Computer 150 provides to other components of the CASS 100, according to some embodiments. Note that the example of FIG. 2A assumes that the components of the Effector Platform 105 are each controlled directly by the Surgical Computer 150. In embodiments where a component is manually controlled by the Surgeon 111, instructions may be provided on the Display 125 or AR HMD 155 instructing the Surgeon 111 how to move the component.

The various components included in the Effector Platform 105 are controlled by the Surgical Computer 150 providing position commands that instruct the component where to move within a coordinate system. In some embodiments, the Surgical Computer 150 provides the Effector Platform 105 with instructions defining how to react when a component of the Effector Platform 105 deviates from a surgical plan. These commands are referenced in FIG. 2A as "haptic" commands. For example, the End Effector 105B may provide a force to resist movement outside of an area where resection is planned. Other commands that may be used by the Effector Platform 105 include vibration and audio cues.

In some embodiments, the end effectors 105B of the robotic arm 105A are operatively coupled with cutting guide 105D. In response to an anatomical model of the surgical scene, the robotic arm 105A can move the end effectors 105B and the cutting guide 105D into position to match the location of the femoral or tibial cut to be performed in accordance with the surgical plan. This can reduce the likelihood of error, allowing the vision system and a processor utilizing that vision system to implement the surgical plan to place a cutting guide 105D at the precise location and orientation relative to the tibia or femur to align a cutting slot of the cutting guide with the cut to be performed according to the surgical plan. Then, a surgeon can use any suitable tool, such as an oscillating or rotating saw or drill to perform the cut (or drill a hole) with perfect placement and orientation because the tool is mechanically limited by the features of the cutting guide 105D. In some embodiments, the cutting guide 105D may include one or more pin holes that are used by a surgeon to drill and screw or pin the cutting guide into place before performing a resection of the patient tissue using the cutting guide. This can free the robotic arm 105A or ensure that the cutting guide 105D is fully affixed without moving relative to the bone to be resected. For example, this procedure can be used to make the first distal cut of the femur during a total knee arthroplasty. In some embodiments, where the arthroplasty is a hip arthroplasty, cutting guide 105D can be fixed to the femoral head or the acetabulum for the respective hip arthroplasty resection. It should be understood that any arthroplasty that utilizes precise cuts can use the robotic arm 105A and/or cutting guide 105D in this manner.

The Resection Equipment 110 is provided with a variety of commands to perform bone or tissue operations. As with the Effector Platform 105, position information may be provided to the Resection Equipment 110 to specify where it should be located when performing resection. Other commands provided to the Resection Equipment 110 may be dependent on the type of resection equipment. For example, for a mechanical or ultrasonic resection tool, the commands may specify the speed and frequency of the tool. For Radiofrequency Ablation (RFA) and other laser ablation tools, the commands may specify intensity and pulse duration.

Some components of the CASS 100 do not need to be directly controlled by the Surgical Computer 150; rather, the Surgical Computer 150 only needs to activate the component, which then executes software locally specifying the manner in which to collect data and provide it to the Surgical Computer 150. In the example of FIG. 2A, there are two components that are operated in this manner: the Tracking System 115 and the Tissue Navigation System 120.

The Surgical Computer 150 provides the Display 125 with any visualization that is needed by the Surgeon 111 during surgery. For monitors, the Surgical Computer 150 may provide instructions for displaying images. GUIs, etc.

using techniques known in the art. The display 125 can include various aspects of the workflow of a surgical plan. During the registration process, for example, the display 125 can show a preoperatively constructed 3D bone model and depict the locations of the probe as the surgeon uses the probe to collect locations of anatomical landmarks on the patient. The display 125 can include information about the surgical target area. For example, in connection with a TKA, the display 125 can depict the mechanical and anatomical axes of the femur and tibia. The display 125 can depict varus and valgus angles for the knee joint based on a surgical plan, and the CASS 100 can depict how such angles will be affected if contemplated revisions to the surgical plan are made. Accordingly, the display 125 is an interactive interface that can dynamically update and display how changes to the surgical plan would impact the procedure and the final position and orientation of implants installed on bone.

As the workflow progresses to preparation of bone cuts or resections, the display 125 can depict the planned or recommended bone cuts before any cuts are performed. The surgeon 111 can manipulate the image display to provide different anatomical perspectives of the target area and can have the option to alter or revise the planned bone cuts based on intraoperative evaluation of the patient. The display 125 can depict how the chosen implants would be installed on the bone if the planned bone cuts are performed. If the surgeon 111 choses to change the previously planned bone cuts, the display 125 can depict how the revised bone cuts would change the position and orientation of the implant when installed on the bone.

The display 125 can provide the surgeon 111 with a variety of data and information about the patient, the planned surgical intervention, and the implants. Various patient-specific information can be displayed, including real-time data concerning the patient's health such as heart rate, blood pressure, etc. The display 125 can also include information about the anatomy of the surgical target region including the location of landmarks, the current state of the anatomy (e.g., whether any resections have been made, the depth and angles of planned and executed bone cuts), and future states of the anatomy as the surgical plan progresses. The display 125 can also provide or depict additional information about the surgical target region. For a TKA, the display 125 can provide information about the gaps (e.g., gap balancing) between the femur and tibia and how such gaps will change if the planned surgical plan is carried out. For a TKA, the display 125 can provide additional relevant information about the knee joint such as data about the joint's tension (e.g., ligament laxity) and information concerning rotation and alignment of the joint. The display 125 can depict how the planned implants' locations and positions will affect the patient as the knee joint is flexed. The display 125 can depict how the use of different implants or the use of different sizes of the same implant will affect the surgical plan and preview how such implants will be positioned on the bone. The CASS 100 can provide such information for each of the planned bone resections in a TKA or THA. In a TKA, the CASS 100 can provide robotic control for one or more of the planned bone resections. For example, the CASS 100 can provide robotic control only for the initial distal femur cut, and the surgeon 111 can manually perform other resections (anterior, posterior and chamfer cuts) using conventional means, such as a 4-in-1 cutting guide or jig 105D.

The display 125 can employ different colors to inform the surgeon of the status of the surgical plan. For example, un-resected bone can be displayed in a first color, resected bone can be displayed in a second color, and planned resections can be displayed in a third color. Implants can be superimposed onto the bone in the display 125, and implant colors can change or correspond to different types or sizes of implants.

The information and options depicted on the display 125 can vary depending on the type of surgical procedure being performed. Further, the surgeon 111 can request or select a particular surgical workflow display that matches or is consistent with his or her surgical plan preferences. For example, for a surgeon 111 who typically performs the tibial cuts before the femoral cuts in a TKA, the display 125 and associated workflow can be adapted to take this preference into account. The surgeon 111 can also preselect that certain steps be included or deleted from the standard surgical workflow display. For example, if a surgeon 111 uses resection measurements to finalize an implant plan but does not analyze ligament gap balancing when finalizing the implant plan, the surgical workflow display can be organized into modules, and the surgeon can select which modules to display and the order in which the modules are provided based on the surgeon's preferences or the circumstances of a particular surgery. Modules directed to ligament and gap balancing, for example, can include pre- and post-resection ligament/gap balancing, and the surgeon 111 can select which modules to include in their default surgical plan workflow depending on whether they perform such ligament and gap balancing before or after (or both) bone resections are performed.

For more specialized display equipment, such as AR HMDs, the Surgical Computer 150 may provide images, text, etc. using the data format supported by the equipment. For example, if the Display 125 is a holography device such as the Microsoft HoloLens™ or Magic Leap One™, the Surgical Computer 150 may use the HoloLens Application Program Interface (API) to send commands specifying the position and content of holograms displayed in the field of view of the Surgeon 111.

In some embodiments, one or more surgical planning models may be incorporated into the CASS 100 and used in the development of the surgical plans provided to the surgeon 111. The term "surgical planning model" refers to software that simulates the biomechanics performance of anatomy under various scenarios to determine the optimal way to perform cutting and other surgical activities. For example, for knee replacement surgeries, the surgical planning model can measure parameters for functional activities, such as deep knee bends, gait, etc., and select cut locations on the knee to optimize implant placement. One example of a surgical planning model is the LIFEMOD™ simulation software from SMITH AND NEPHEW. INC. In some embodiments, the Surgical Computer 150 includes computing architecture that allows full execution of the surgical planning model during surgery (e.g., a GPU-based parallel processing environment). In other embodiments, the Surgical Computer 150 may be connected over a network to a remote computer that allows such execution, such as a Surgical Data Server 180 (see FIG. 2C). As an alternative to full execution of the surgical planning model, in some embodiments, a set of transfer functions are derived that simplify the mathematical operations captured by the model into one or more predictor equations. Then, rather than execute the full simulation during surgery, the predictor equations are used. Further details on the use of transfer functions are described in U.S. Provisional Patent Application No. 62/719,415 entitled "Patient Specific Surgical Method and System." the entirety of which is incorporated herein by reference.

FIG. 2B shows examples of some of the types of data that can be provided to the Surgical Computer 150 from the various components of the CASS 100. In some embodiments, the components may stream data to the Surgical Computer 150 in real-time or near real-time during surgery. In other embodiments, the components may queue data and send it to the Surgical Computer 150 at set intervals (e.g., every second). Data may be communicated using any format known in the art. Thus, in some embodiments, the components all transmit data to the Surgical Computer 150 in a common format. In other embodiments, each component may use a different data format, and the Surgical Computer 150 is configured with one or more software applications that enable translation of the data.

In general, the Surgical Computer 150 may serve as the central point where CASS data is collected. The exact content of the data will vary depending on the source. For example, each component of the Effector Platform 105 provides a measured position to the Surgical Computer 150. Thus, by comparing the measured position to a position originally specified by the Surgical Computer 150 (see FIG. 2B), the Surgical Computer can identify deviations that take place during surgery.

The Resection Equipment 110 can send various types of data to the Surgical Computer 150 depending on the type of equipment used. Example data types that may be sent include the measured torque, audio signatures, and measured displacement values. Similarly, the Tracking Technology 115 can provide different types of data depending on the tracking methodology employed. Example tracking data types include position values for tracked items (e.g., anatomy, tools, etc.), ultrasound images, and surface or landmark collection points or axes. The Tissue Navigation System 120 provides the Surgical Computer 150 with anatomic locations, shapes, etc. as the system operates.

Although the Display 125 generally is used for outputting data for presentation to the user, it may also provide data to the Surgical Computer 150. For example, for embodiments where a monitor is used as part of the Display 125, the Surgeon 111 may interact with a GUI to provide inputs which are sent to the Surgical Computer 150 for further processing. For AR applications, the measured position and displacement of the HMD may be sent to the Surgical Computer 150 so that it can update the presented view as needed.

During the post-operative phase of the episode of care, various types of data can be collected to quantify the overall improvement or deterioration in the patient's condition as a result of the surgery. The data can take the form of, for example, self-reported information reported by patients via questionnaires. For example, in the context of a knee replacement surgery, functional status can be measured with an Oxford Knee Score questionnaire, and the post-operative quality of life can be measured with a EQ5D-5L questionnaire. Other examples in the context of a hip replacement surgery may include the Oxford Hip Score, Harris Hip Score, and WOMAC (Western Ontario and McMaster Universities Osteoarthritis index). Such questionnaires can be administered, for example by a healthcare professional directly in a clinical setting or using a mobile app that allows the patient to respond to questions directly. In some embodiments, the patient may be outfitted with one or more wearable devices that collect data relevant to the surgery. For example, following a knee surgery, the patient may be outfitted with a knee brace that includes sensors that monitor knee positioning, flexibility, etc. This information can be collected and transferred to the patient's mobile device for review by the surgeon to evaluate the outcome of the surgery and address any issues. In some embodiments, one or more cameras can capture and record the motion of a patient's body segments during specified activities postoperatively. This motion capture can be compared to a biomechanics model to better understand the functionality of the patient's joints and better predict progress in recovery and identify any possible revisions that may be needed.

The post-operative stage of the episode of care can continue over the entire life of a patient. For example, in some embodiments, the Surgical Computer 150 or other components comprising the CASS 100 can continue to receive and collect data relevant to a surgical procedure after the procedure has been performed. This data may include, for example, images, answers to questions, "normal" patient data (e.g., blood type, blood pressure, conditions, medications, etc.), biometric data (e.g., gait, etc.), and objective and subjective data about specific issues (e.g., knee or hip joint pain). This data may be explicitly provided to the Surgical Computer 150 or other CASS component by the patient or the patient's physician(s). Alternatively or additionally, the Surgical Computer 150 or other CASS component can monitor the patient's EMR and retrieve relevant information as it becomes available. This longitudinal view of the patient's recovery allows the Surgical Computer 150 or other CASS component to provide a more objective analysis of the patient's outcome to measure and track success or lack of success for a given procedure. For example, a condition experienced by a patient long after the surgical procedure can be linked back to the surgery through a regression analysis of various data items collected during the episode of care. This analysis can be further enhanced by performing the analysis on groups of patients that had similar procedures and/or have similar anatomies.

In some embodiments, data is collected at a central location to provide for easier analysis and use. Data can be manually collected from various CASS components in some instances. For example, a portable storage device (e.g., USB stick) can be attached to the Surgical Computer 150 into order to retrieve data collected during surgery. The data can then be transferred, for example, via a desktop computer to the centralized storage. Alternatively, in some embodiments, the Surgical Computer 150 is connected directly to the centralized storage via a Network 175 as shown in FIG. 2C.

Figure 2C:
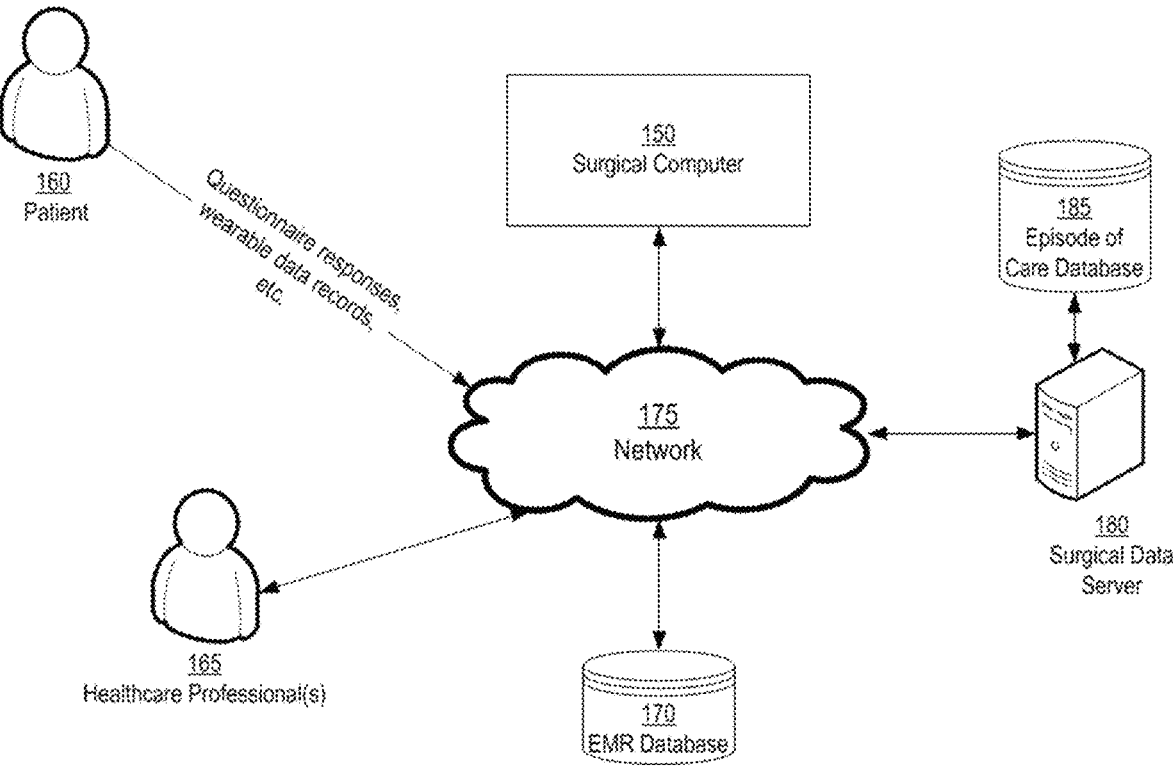
FIG. 2C depicts an illustrative implementation in which a surgical computer is connected to a surgical data server via a network in accordance with an embodiment.

FIG. 2C illustrates a "cloud-based" implementation in which the Surgical Computer 150) is connected to a Surgical Data Server 180 via a Network 175. This Network 175 may be, for example, a private intranet or the Internet. In addition to the data from the Surgical Computer 150), other sources can transfer relevant data to the Surgical Data Server 180. The example of FIG. 2C shows 3 additional data sources: the Patient 160, Healthcare Professional(s) 165, and an EMR Database 170. Thus, the Patient 160 can send pre-operative and post-operative data to the Surgical Data Server 180, for example, using a mobile app. The Healthcare Professional(s) 165 includes the surgeon and his or her staff as well as any other professionals working with Patient 160 (e.g., a personal physician, a rehabilitation specialist, etc.). It should also be noted that the EMR Database 170) may be used for both pre-operative and post-operative data. For example, assuming that the Patient 160 has given adequate permissions, the Surgical Data Server 180 may collect the EMR of the Patient pre-surgery. Then, the Surgical Data Server 180 may continue to monitor the EMR for any updates post-surgery.

At the Surgical Data Server 180, an Episode of Care Database 185 is used to store the various data collected over a patient's episode of care. The Episode of Care Database 185 may be implemented using any technique known in the art. For example, in some embodiments, a SQL-based database may be used where all of the various data items are structured in a manner that allows them to be readily incorporated in two SQL's collection of rows and columns. However, in other embodiments a No-SQL database may be employed to allow for unstructured data, while providing the ability to rapidly process and respond to queries. As is understood in the art, the term "No-SQL" is used to define a class of data stores that are non-relational in their design. Various types of No-SQL databases may generally be grouped according to their underlying data model. These groupings may include databases that use column-based data models (e.g., Cassandra), document-based data models (e.g., MongoDB), key-value based data models (e.g., Redis), and/or graph-based data models (e.g., Allego). Any type of No-SQL database may be used to implement the various embodiments described herein and, in some embodiments, the different types of databases may support the Episode of Care Database 185.

Data can be transferred between the various data sources and the Surgical Data Server 180 using any data format and transfer technique known in the art. It should be noted that the architecture shown in FIG. 2C allows transmission from the data source to the Surgical Data Server 180, as well as retrieval of data from the Surgical Data Server 180 by the data sources. For example, as explained in detail below, in some embodiments, the Surgical Computer 150 may use data from past surgeries, machine learning models, etc. to help guide the surgical procedure.

In some embodiments, the Surgical Computer 150 or the Surgical Data Server 180 may execute a de-identification process to ensure that data stored in the Episode of Care Database 185 meets Health Insurance Portability and Accountability Act (HIPAA) standards or other requirements mandated by law. HIPAA provides a list of certain identifiers that must be removed from data during de-identification. The aforementioned de-identification process can scan for these identifiers in data that is transferred to the Episode of Care Database 185 for storage. For example, in one embodiment, the Surgical Computer 150 executes the de-identification process just prior to initiating transfer of a particular data item or set of data items to the Surgical Data Server 180. In some embodiments, a unique identifier is assigned to data from a particular episode of care to allow for re-identification of the data if necessary.

Although FIGS. 2A-2C discuss data collection in the context of a single episode of care, it should be understood that the general concept can be extended to data collection from multiple episodes of care. For example, surgical data may be collected over an entire episode of care each time a surgery is performed with the CASS 100 and stored at the Surgical Computer 150 or at the Surgical Data Server 180. As explained in further detail below; a robust database of episode of care data allows the generation of optimized values, measurements, distances, or other parameters and other recommendations related to the surgical procedure. In some embodiments, the various datasets are indexed in the database or other storage medium in a manner that allows for rapid retrieval of relevant information during the surgical procedure. For example, in one embodiment, a patientcentric set of indices may be used so that data pertaining to a particular patient or a set of patients similar to a particular patient can be readily extracted. This concept can be similarly applied to surgeons, implant characteristics, CASS component versions, etc.

Further details of the management of episode of care data is described in U.S. Patent Application No. 62/783,858 filed Dec. 21, 2018 and entitled "Methods and Systems for Providing an Episode of Care," the entirety of which is incorporated herein by reference.

Open Versus Closed Digital Ecosystems

In some embodiments, the CASS 100 is designed to operate as a self-contained or "closed" digital ecosystem. Each component of the CASS 100 is specifically designed to be used in the closed ecosystem, and data is generally not accessible to devices outside of the digital ecosystem. For example, in some embodiments, each component includes software or firmware that implements proprietary protocols for activities such as communication, storage, security, etc. The concept of a closed digital ecosystem may be desirable for a company that wants to control all components of the CASS 100 to ensure that certain compatibility, security, and reliability standards are met. For example, the CASS 100 can be designed such that a new component cannot be used with the CASS unless it is certified by the company.

In other embodiments, the CASS 100 is designed to operate as an "open" digital ecosystem. In these embodiments, components may be produced by a variety of different companies according to standards for activities, such as communication, storage, and security. Thus, by using these standards, any company can freely build an independent, compliant component of the CASS platform. Data may be transferred between components using publicly available application programming interfaces (APIs) and open, shareable data formats.

To illustrate one type of recommendation that may be performed with the CASS 100, a technique for optimizing surgical parameters is disclosed below. The term "optimization" in this context means selection of parameters that are optimal based on certain specified criteria. In an extreme case, optimization can refer to selecting optimal parameter(s) based on data from the entire episode of care, including any pre-operative data, the state of CASS data at a given point in time, and post-operative goals. Moreover, optimization may be performed using historical data, such as data generated during past surgeries involving, for example, the same surgeon, past patients with physical characteristics similar to the current patient, or the like.

The optimized parameters may depend on the portion of the patient's anatomy to be operated on. For example, for knee surgeries, the surgical parameters may include positioning information for the femoral and tibial component including, without limitation, rotational alignment (e.g., varus/valgus rotation, external rotation, flexion rotation for the femoral component, posterior slope of the tibial component), resection depths (e.g., varus knee, valgus knee), and implant type, size and position. The positioning information may further include surgical parameters for the combined implant, such as overall limb alignment, combined tibiofemoral hyperextension, and combined tibiofemoral resection. Additional examples of parameters that could be optimized for a given TKA femoral implant by the CASS 100 include the following:

| Parameter | Reference | Exemplary Recommendation (s) |
|---|---|---|
| Size | Posterior | The largest sized implant that does not overhang medial/lateral bone edges or overhang the anterior femur. A size that does not result in overstuffing the patella femoral joint |
| Implant Position - Medial Lateral | Medial/lateral cortical bone edges | Center the implant evenly between the medial/lateral cortical bone edges |
| Resection Depth - Varus Knee | Distal and posterior lateral | 6 mm of bone |
| Resection Depth - Valgus Knee | Distal and posterior medial | 7 mm of bone |
| Rotation - Varus/Valgus | Mechanical Axis | 1° varus |
| Rotation - External | Transepicondylar Axis | 1° external from the transepicondylar axis |
| Rotation - Flexion | Mechanical Axis | 3° flexed |

Additional examples of parameters that could be optimized for a given TKA tibial implant by the CASS 100 include the following:

| Parameter | Reference | Exemplary Recommendation (s) |
|---|---|---|
| Size | Posterior | The largest sized implant that does not overhang the medial, lateral, anterior, and posterior tibial edges |
| Implant Position | Medial/lateral and anterior/posterior cortical bone edges | Center the implant evenly between the medial/lateral and anterior/posterior cortical bone edges |
| Resection Depth - Varus Knee | Lateral/Medial | 4 mm of bone |
| Resection Depth - Valgus Knee | Lateral/Medial | 5 mm of bone |
| Rotation - Varus/Valgus | Mechanical Axis | 1° valgus |
| Rotation - External | Tibial Anterior Posterior Axis | 1° external from the tibial anterior paxis |
| Posterior Slope | Mechanical Axis | 3° posterior slope |

For hip surgeries, the surgical parameters may comprise femoral neck resection location and angle, cup inclination angle, cup anteversion angle, cup depth, femoral stem design, femoral stem size, fit of the femoral stem within the canal, femoral offset, leg length, and femoral version of the implant.

Shoulder parameters may include, without limitation, humeral resection depth/angle, humeral stem version, humeral offset, glenoid version and inclination, as well as reverse shoulder parameters such as humeral resection depth/angle, humeral stem version, Glenoid tilt/version, glenosphere orientation, glenosphere offset and offset direction.

Various conventional techniques exist for optimizing surgical parameters. However, these techniques are typically computationally intensive and, thus, parameters often need to be determined pre-operatively. As a result, the surgeon is limited in his or her ability to make modifications to optimized parameters based on issues that may arise during surgery. Moreover, conventional optimization techniques typically operate in a "black box" manner with little or no explanation regarding recommended parameter values. Thus, if the surgeon decides to deviate from a recommended parameter value, the surgeon typically does so without a full understanding of the effect of that deviation on the rest of the surgical workflow, or the impact of the deviation on the patient's post-surgery quality of life.

Operative Patient Care System

Figure 3:
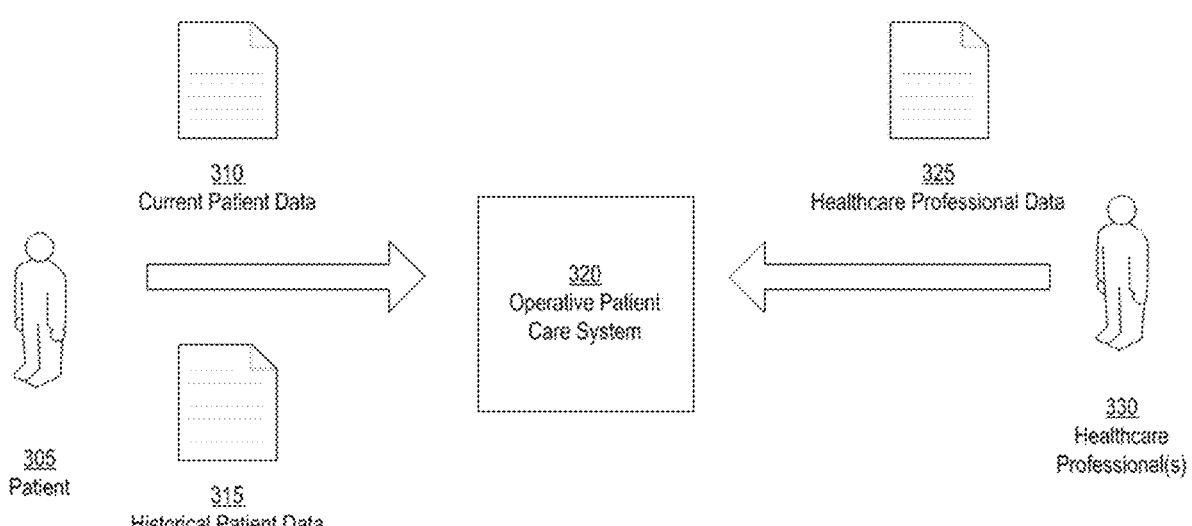
FIG. 3 depicts an operative patient care system and illustrative data sources in accordance with an embodiment.

The general concepts of optimization may be extended to the entire episode of care using an Operative Patient Care System 320 that uses the surgical data, and other data from the Patient 305 and Healthcare Professionals 330 to optimize outcomes and patient satisfaction as depicted in FIG. 3.

Conventionally, pre-operative diagnosis, pre-operative surgical planning, intra-operative execution of a prescribed plan, and post-operative management of total joint arthroplasty are based on individual experience, published literature, and training knowledge bases of surgeons (ultimately, tribal knowledge of individual surgeons and their 'network' of peers and journal publications) and their native ability to make accurate intra-operative tactile discernment of "balance" and accurate manual execution of planar resections using guides and visual cues. This existing knowledge base and execution is limited with respect to the outcomes optimization offered to patients needing care. For example, limits exist with respect to accurately diagnosing a patient to the proper, least-invasive prescribed care: aligning dynamic patient, healthcare economic, and surgeon preferences with patient-desired outcomes: executing a surgical plan resulting in proper bone alignment and balance, etc.; and receiving data from disconnected sources having different biases that are difficult to reconcile into a holistic patient framework. Accordingly, a data-driven tool that more accurately models anatomical response and guides the surgical plan can improve the existing approach.

The Operative Patient Care System 320 is designed to utilize patient specific data, surgeon data, healthcare facility data, and historical outcome data to develop an algorithm that suggests or recommends an optimal overall treatment plan for the patient's entire episode of care (preoperative, operative, and postoperative) based on a desired clinical outcome. For example, in one embodiment, the Operative Patient Care System 320 tracks adherence to the suggested or recommended plan, and adapts the plan based on patient/ care provider performance. Once the surgical treatment plan is complete, collected data is logged by the Operative Patient Care System 320 in a historical database. This database is accessible for future patients and the development of future treatment plans. In addition to utilizing statistical and mathematical models, simulation tools (e.g., LIFEMOD®) can be used to simulate outcomes, alignment, kinematics, etc. based on a preliminary or proposed surgical plan, and reconfigure the preliminary or proposed plan to achieve desired or optimal results according to a patient's profile or a surgeon's preferences. The Operative Patient Care System 320 ensures that each patient is receiving personalized surgical and rehabilitative care, thereby improving the chance of successful clinical outcomes and lessening the economic burden on the facility associated with near-term revision.

In some embodiments, the Operative Patient Care System 320 employs a data collecting and management method to provide a detailed surgical case plan with distinct steps that are monitored and/or executed using a CASS 100. The performance of the user(s) is calculated at the completion of each step and can be used to suggest changes to the subsequent steps of the case plan. Case plan generation relies on a series of input data that is stored on a local or cloud-storage database. Input data can be related to both the current patient undergoing treatment and historical data from patients who have received similar treatment(s).

A Patient 305 provides inputs such as Current Patient Data 310 and Historical Patient Data 315 to the Operative Patient Care System 320. Various methods generally known in the art may be used to gather such inputs from the Patient 305. For example, in some embodiments, the Patient 305 fills out a paper or digital survey that is parsed by the Operative Patient Care System 320 to extract patient data. In other embodiments, the Operative Patient Care System 320 may extract patient data from existing information sources, such as electronic medical records (EMRs), health history files, and payer/provider historical files. In still other embodiments, the Operative Patient Care System 320) may provide an application program interface (API) that allows the external data source to push data to the Operative Patient Care System. For example, the Patient 305 may have a mobile phone, wearable device, or other mobile device that collects data (e.g., heart rate, pain or discomfort levels, exercise or activity levels, or patient-submitted responses to the patient's adherence with any number of pre-operative plan criteria or conditions) and provides that data to the Operative Patient Care System 320. Similarly, the Patient 305 may have a digital application on his or her mobile or wearable device that enables data to be collected and transmitted to the Operative Patient Care System 320.

Current Patient Data 310 can include, but is not limited to, activity level, preexisting conditions, comorbidities, prehab performance, health and fitness level, pre-operative expectation level (relating to hospital, surgery, and recovery), a Metropolitan Statistical Area (MSA) driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels of pain or discomfort, care infrastructure information (payer coverage type, home health care infrastructure level, etc.), and an indication of the expected ideal outcome of the procedure.

Historical Patient Data 315 can include, but is not limited to, activity level, preexisting conditions, comorbidities, prehab performance, health and fitness level, pre-operative expectation level (relating to hospital, surgery, and recovery), a MSA driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels or pain or discomfort, care infrastructure information (payer coverage type, home health care infrastructure level, etc.), expected ideal outcome of the procedure, actual outcome of the procedure (patient reported outcomes [PROs], survivorship of implants, pain levels, activity levels, etc.), sizes of implants used, position/orientation/alignment of implants used, soft-tissue balance achieved, etc.

Healthcare Professional(s) 330) conducting the procedure or treatment may provide various types of data 325 to the Operative Patient Care System 320. This Healthcare Professional Data 325 may include, for example, a description of a known or preferred surgical technique (e.g., Cruciate Retaining (CR) vs Posterior Stabilized (PS), up-vs downsizing, tourniquet vs tourniquet-less, femoral stem style, preferred approach for THA, etc.), the level of training of the Healthcare Professional(s) 330 (e.g., years in practice, fellowship trained, where they trained, whose techniques they emulate), previous success level including historical data (outcomes, patient satisfaction), and the expected ideal outcome with respect to range of motion, days of recovery, and survivorship of the device. The Healthcare Professional Data 325 can be captured, for example, with paper or digital surveys provided to the Healthcare Professional 330, via inputs to a mobile application by the Healthcare Professional, or by extracting relevant data from EMRs. In addition, the CASS 100 may provide data such as profile data (e.g., a Patient Specific Knee Instrument Profile) or historical logs describing use of the CASS during surgery.

Information pertaining to the facility where the procedure or treatment will be conducted may be included in the input data. This data can include, without limitation, the following: Ambulatory Surgery Center (ASC) vs hospital, facility trauma level, Comprehensive Care for Joint Replacement Program (CJR) or bundle candidacy, a MSA driven score, community vs metro, academic vs non-academic, postoperative network access (Skilled Nursing Facility [SNF] only, Home Health, etc.), availability of medical professionals, implant availability, and availability of surgical equipment.

These facility inputs can be captured by, for example and without limitation, Surveys (Paper/Digital), Surgery Scheduling Tools (e.g., apps, Websites, Electronic Medical Records [EMRs], etc.), Databases of Hospital Information (on the Internet), etc. Input data relating to the associated healthcare economy including, but not limited to, the socioeconomic profile of the patient, the expected level of reimbursement the patient will receive, and if the treatment is patient specific may also be captured.

These healthcare economic inputs can be captured by, for example and without limitation, Surveys (Paper/Digital), Direct Payer Information, Databases of Socioeconomic status (on the Internet with zip code), etc. Finally, data derived from simulation of the procedure is captured. Simulation inputs include implant size, position, and orientation. Simulation can be conducted with custom or commercially available anatomical modeling software programs (e.g., LIFE-MOD®, Any Body, or OpenSIM). It is noted that the data inputs described above may not be available for every patient, and the treatment plan will be generated using the data that is available.

Prior to surgery, the Patient Data 310, 315 and Healthcare Professional Data 325 may be captured and stored in a cloud-based or online database (e.g., the Surgical Data Server 180 shown in FIG. 2C). Information relevant to the procedure is supplied to a computing system via wireless data transfer or manually with the use of portable media storage. The computing system is configured to generate a case plan for use with a CASS 100. Case plan generation will be described hereinafter. It is noted that the system has access to historical data from previous patients undergoing treatment, including implant size, placement, and orientation as generated by a computer-assisted, patient-specific knee instrument (PSKI) selection system, or automatically by the CASS 100 itself. To achieve this, case log data is uploaded to the historical database by a surgical sales rep or case engineer using an online portal. In some embodiments, data transfer to the online database is wireless and automated.

Historical data sets from the online database are used as inputs to a machine learning model such as, for example, a recurrent neural network (RNN) or other form of artificial neural network. As is generally understood in the art, an artificial neural network functions similar to a biologic neural network and is comprised of a series of nodes and connections. The machine learning model is trained to predict one or more values based on the input data. For the sections that follow, it is assumed that the machine learning model is trained to generate predictor equations. These predictor equations may be optimized to determine the optimal size, position, and orientation of the implants to achieve the best outcome or satisfaction level.

Once the procedure is complete, all patient data and available outcome data, including the implant size, position and orientation determined by the CASS 100, are collected and stored in the historical database. Any subsequent calculation of the target equation via the RNN will include the data from the previous patient in this manner, allowing for continuous improvement of the system.

In addition to, or as an alternative to determining implant positioning, in some embodiments, the predictor equation and associated optimization can be used to generate the resection planes for use with a PSKI system. When used with a PSKI system, the predictor equation computation and optimization are completed prior to surgery. Patient anatomy is estimated using medical image data (x-ray. CT. MRI). Global optimization of the predictor equation can provide an ideal size and position of the implant components. Boolean intersection of the implant components and patient anatomy is defined as the resection volume. PSKI can be produced to remove the optimized resection envelope. In this embodiment, the surgeon cannot alter the surgical plan intraoperatively.

The surgeon may choose to alter the surgical case plan at any time prior to or during the procedure. If the surgeon elects to deviate from the surgical case plan, the altered size, position, and/or orientation of the component(s) is locked, and the global optimization is refreshed based on the new size, position, and/or orientation of the component(s) (using the techniques previously described) to find the new ideal position of the other component(s) and the corresponding resections needed to be performed to achieve the newly optimized size, position and/or orientation of the component(s). For example, if the surgeon determines that the size, position and/or orientation of the femoral implant in a TKA needs to be updated or modified intraoperatively, the femoral implant position is locked relative to the anatomy, and the new optimal position of the tibia will be calculated (via global optimization) considering the surgeon's changes to the femoral implant size, position and/or orientation. Furthermore, if the surgical system used to implement the case plan is robotically assisted (e.g., as with NAVIO®; or the MAKO Rio), bone removal and bone morphology during the surgery can be monitored in real time. If the resections made during the procedure deviate from the surgical plan, the subsequent placement of additional components may be optimized by the processor taking into account the actual resections that have already been made.

Figure 4A:
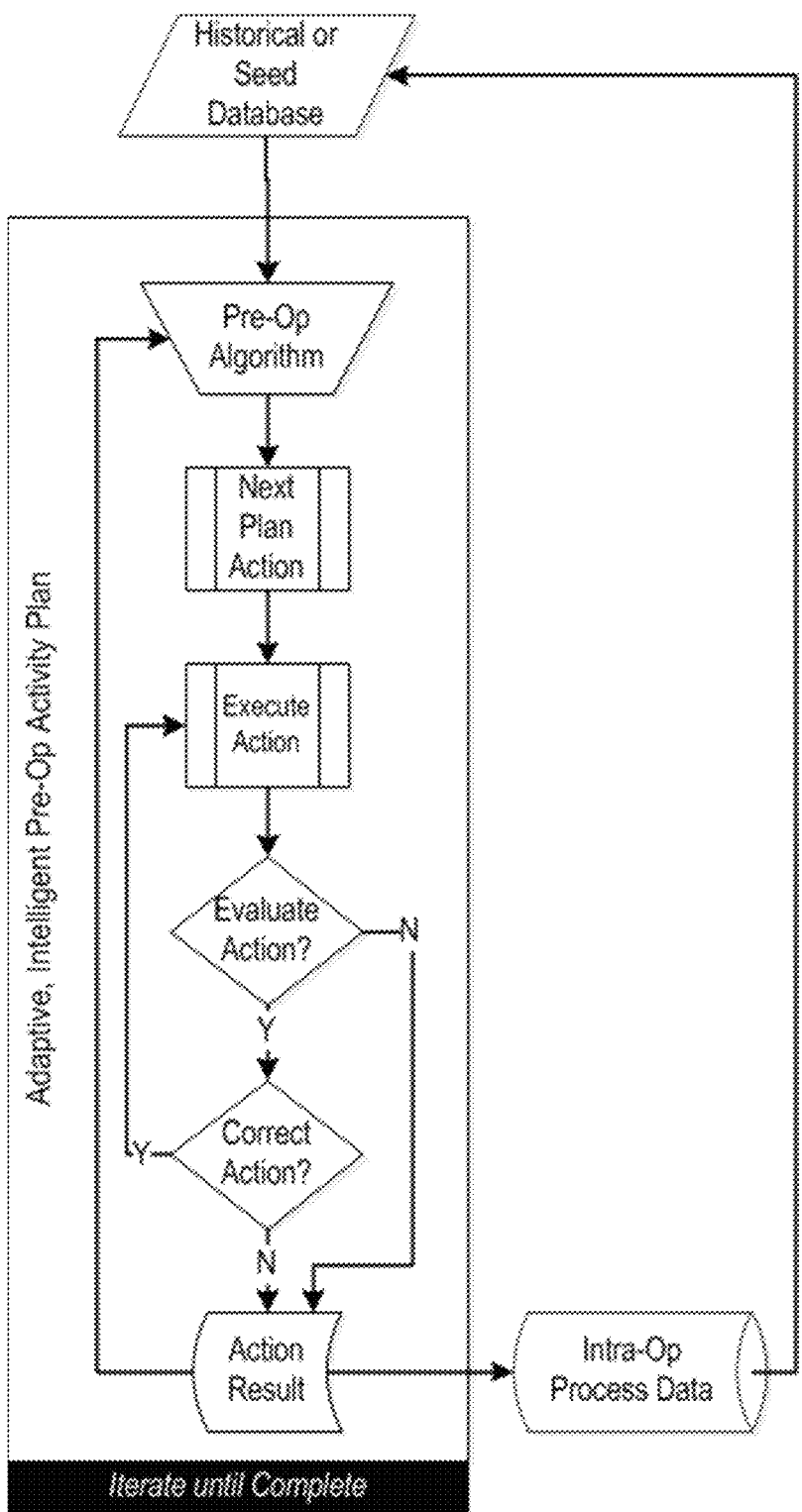
FIG. 4A depicts an illustrative flow diagram for determining a pre-operative surgical plan in accordance with an embodiment.
Figure 4B:
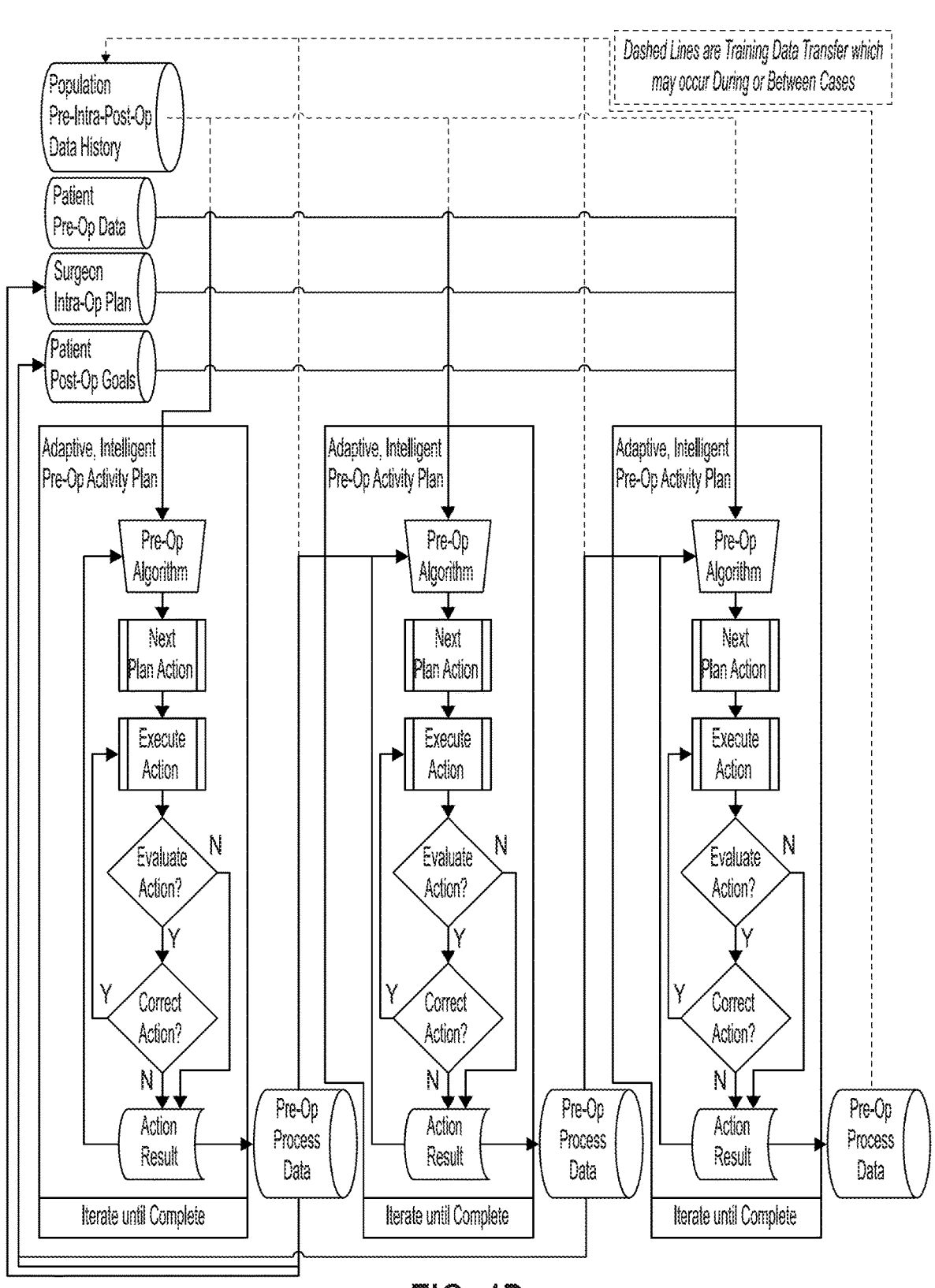
FIG. 4B depicts an illustrative flow diagram for determining an episode of care including pre-operative, intraoperative, and post-operative actions in accordance with an embodiment.

FIG. 4A illustrates how the Operative Patient Care System 320 may be adapted for performing case plan matching services. In this example, data is captured relating to the current patient 310 and is compared to all or portions of a historical database of patient data and associated outcomes 315. For example, the surgeon may elect to compare the plan for the current patient against a subset of the historical database. Data in the historical database can be filtered to include, for example, only data sets with favorable outcomes, data sets corresponding to historical surgeries of patients with profiles that are the same or similar to the current patient profile, data sets corresponding to a particular surgeon, data sets corresponding to a particular aspect of the surgical plan (e.g., only surgeries where a particular ligament is retained), or any other criteria selected by the surgeon or medical professional. If, for example, the current patient data matches or is correlated with that of a previous patient who experienced a good outcome, the case plan from the previous patient can be accessed and adapted or adopted for use with the current patient. The predictor equation may be used in conjunction with an intra-operative algorithm that identifies or determines the actions associated with the case plan. Based on the relevant and/or preselected information from the historical database, the intra-operative algorithm determines a series of recommended actions for the surgeon to perform. Each execution of the algorithm produces the next action in the case plan. If the surgeon performs the action, the results are evaluated. The results of the surgeon's performing the action are used to refine and update inputs to the intra-operative algorithm for generating the next step in the case plan. Once the case plan has been fully executed all data associated with the case plan, including any deviations performed from the recommended actions by the surgeon, are stored in the database of historical data. In some embodiments, the system utilizes preoperative, intraoperative, or postoperative modules in a piecewise fashion, as opposed to the entire continuum of care. In other words, caregivers can prescribe any permutation or combination of treatment modules including the use of a single module. These concepts are illustrated in FIG. 4B and can be applied to any type of surgery utilizing the CASS 100.

Surgery Process Display

As noted above with respect to FIGS. 1-2C, the various components of the CASS 100 generate detailed data records during surgery. The CASS 100 can track and record various actions and activities of the surgeon during each step of the surgery and compare actual activity to the pre-operative or intraoperative surgical plan. In some embodiments, a software tool may be employed to process this data into a format where the surgery can be effectively "played-back." For example, in one embodiment, one or more GUIs may be used that depict all of the information presented on the Display 125 during surgery. This can be supplemented with graphs and images that depict the data collected by different tools. For example, a GUI that provides a visual depiction of the knee during tissue resection may provide the measured torque and displacement of the resection equipment adjacent to the visual depiction to better provide an understanding of any deviations that occurred from the planned resection area. The ability to review a play back of the surgical plan or toggle between different aspects of the actual surgery vs. the surgical plan could provide benefits to the surgeon and/or surgical staff, allowing such persons to identify any deficiencies or challenging aspects of a surgery so that they can be modified in future surgeries. Similarly, in academic settings, the aforementioned GUIs can be used as a teaching tool for training future surgeons and/or surgical staff. Additionally, because the data set effectively records many aspects of the surgeon's activity, it may also be used for other reasons (e.g., legal or compliance reasons) as evidence of correct or incorrect performance of a particular surgical procedure.

Over time, as more and more surgical data is collected, a rich library of data may be acquired that describes surgical procedures performed for various types of anatomy (knee, shoulder, hip, etc.) by different surgeons for different patients. Moreover, aspects such as implant type and dimension, patient demographics, etc. can further be used to enhance the overall dataset. Once the dataset has been established, it may be used to train a machine learning model (e.g., RNN) to make predictions of how surgery will proceed based on the current state of the CASS 100.

Training of the machine learning model can be performed as follows. The overall state of the CASS 100 can be sampled over a plurality of time periods for the duration of the surgery. The machine learning model can then be trained to translate a current state at a first time period to a future state at a different time period. By analyzing the entire state of the CASS 100 rather than the individual data items, any causal effects of interactions between different components of the CASS 100 can be captured. In some embodiments, a plurality of machine learning models may be used rather than a single model. In some embodiments, the machine learning model may be trained not only with the state of the CASS 100, but also with patient data (e.g., captured from an EMR) and an identification of members of the surgical staff. This allows the model to make predictions with even greater specificity. Moreover, it allows surgeons to selectively make predictions based only on their own surgical experiences if desired.

Figure 4C:
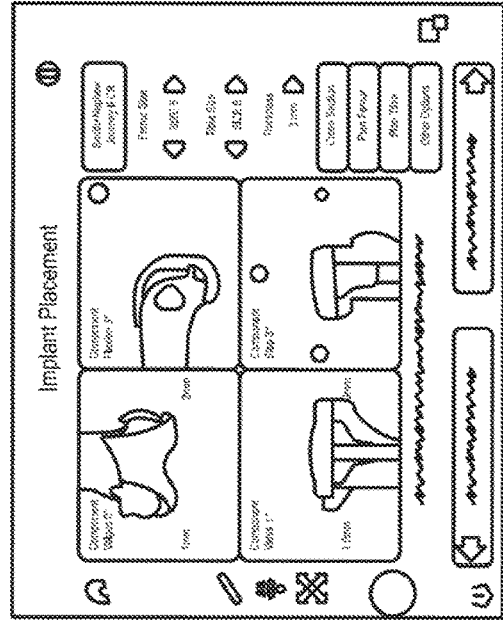
FIG. 4C depicts illustrative graphical user interfaces including images depicting an implant placement in accordance with an embodiment.
Figure 4C:
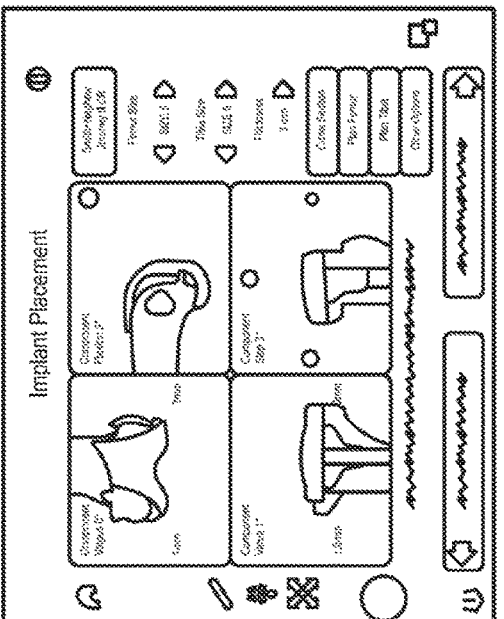

In some embodiments, predictions or recommendations made by the aforementioned machine learning models can be directly integrated into the surgical workflow. For example, in some embodiments, the Surgical Computer 150 may execute the machine learning model in the background making predictions or recommendations for upcoming actions or surgical conditions. A plurality of states can thus be predicted or recommended for each period. For example, the Surgical Computer 150) may predict or recommend the state for the next 5 minutes in 30 second increments. Using this information, the surgeon can utilize a "process display" view of the surgery that allows visualization of the future state. For example. FIG. 4C depicts a series of images that may be displayed to the surgeon depicting the implant placement interface. The surgeon can cycle through these images, for example, by entering a particular time into the display 125 of the CASS 100 or instructing the system to advance or rewind the display in a specific time increment using a tactile, oral, or other instruction. In one embodiment, the process display can be presented in the upper portion of the surgeon's field of view in the AR HMD. In some embodiments, the process display can be updated in real-time. For example, as the surgeon moves resection tools around the planned resection area, the process display can be updated so that the surgeon can see how his or her actions are affecting the other aspects of the surgery.

In some embodiments, rather than simply using the current state of the CASS 100 as an input to the machine learning model, the inputs to the model may include a planned future state. For example, the surgeon may indicate that he or she is planning to make a particular bone resection of the knee joint. This indication may be entered manually into the Surgical Computer 150 or the surgeon may verbally provide the indication. The Surgical Computer 150 can then produce a film strip showing the predicted effect of the cut on the surgery. Such a film strip can depict over specific time increments how the surgery will be affected, including, for example, changes in the patient's anatomy, changes to implant position and orientation, and changes regarding surgical intervention and instrumentation, if the contemplated course of action were to be performed. A surgeon or medical professional can invoke or request this type of film strip at any point in the surgery to preview how a contemplated course of action would affect the surgical plan if the contemplated action were to be carried out.

It should be further noted that, with a sufficiently trained machine learning model and robotic CASS, various aspects of the surgery can be automated such that the surgeon only needs to be minimally involved, for example, by only providing approval for various steps of the surgery. For example, robotic control using arms or other means can be gradually integrated into the surgical workflow over time with the surgeon slowly becoming less and less involved with manual interaction versus robot operation. The machine learning model in this case can learn what robotic commands are required to achieve certain states of the CASS-implemented plan. Eventually, the machine learning model may be used to produce a film strip or similar view or display that predicts and can preview the entire surgery from an initial state. For example, an initial state may be defined that includes the patient information, the surgical plan, implant characteristics, and surgeon preferences. Based on this information, the surgeon could preview an entire surgery to confirm that the CASS-recommended plan meets the surgeon's expectations and/or requirements. Moreover, because the output of the machine learning model is the state of the CASS 100 itself, commands can be derived to control the components of the CASS to achieve each predicted state. In the extreme case, the entire surgery could thus be automated based on just the initial state information.

Using the Point Probe to Acquire High-Resolution of Key Areas during Hip Surgeries Use of the point probe is described in U.S. patent application Ser. No. 14/955,742 entitled "Systems and Methods for Planning and Performing Image Free Implant Revision Surgery," the entirety of which is incorporated herein by reference. Briefly, an optically tracked point probe may be used to map the actual surface of the target bone that needs a new implant. Mapping is performed after removal of the defective or worn-out implant, as well as after removal of any diseased or otherwise unwanted bone. A plurality of points is collected on the bone surfaces by brushing or scraping the entirety of the remaining bone with the tip of the point probe. This is referred to as tracing or "painting" the bone. The collected points are used to create a three-dimensional model or surface map of the bone surfaces in the computerized planning system. The created 3D model of the remaining bone is then used as the basis for planning the procedure and necessary implant sizes. An alternative technique that uses X-rays to determine a 3D model is described in U.S. Provisional Patent Application No. 62/658,988, filed Apr. 17, 2018 and entitled "Three Dimensional Guide with Selective Bone Matching," the entirety of which is incorporated herein by reference.

For hip applications, the point probe painting can be used to acquire high resolution data in key areas such as the acetabular rim and acetabular fossa. This can allow a surgeon to obtain a detailed view before beginning to ream. For example, in one embodiment, the point probe may be used to identify the floor (fossa) of the acetabulum. As is well understood in the art, in hip surgeries, it is important to ensure that the floor of the acetabulum is not compromised during reaming so as to avoid destruction of the medial wall. If the medial wall were inadvertently destroyed, the surgery would require the additional step of bone grafting. With this in mind, the information from the point probe can be used to provide operating guidelines to the acetabular reamer during surgical procedures. For example, the acetabular reamer may be configured to provide haptic feedback to the surgeon when he or she reaches the floor or otherwise deviates from the surgical plan. Alternatively, the CASS 100 may automatically stop the reamer when the floor is reached or when the reamer is within a threshold distance.

As an additional safeguard, the thickness of the area between the acetabulum and the medial wall could be estimated. For example, once the acetabular rim and acetabular fossa has been painted and registered to the pre-operative 3D model, the thickness can readily be estimated by comparing the location of the surface of the acetabulum to the location of the medial wall. Using this knowledge, the CASS 100 may provide alerts or other responses in the event that any surgical activity is predicted to protrude through the acetabular wall while reaming.

The point probe may also be used to collect high resolution data of common reference points used in orienting the 3D model to the patient. For example, for pelvic plane landmarks like the ASIS and the pubic symphysis, the surgeon may use the point probe to paint the bone to represent a true pelvic plane. Given a more complete view of these landmarks, the registration software has more information to orient the 3D model.

The point probe may also be used to collect high-resolution data describing the proximal femoral reference point that could be used to increase the accuracy of implant placement. For example, the relationship between the tip of the Greater Trochanter (GT) and the center of the femoral head is commonly used as reference point to align the femoral component during hip arthroplasty. The alignment is highly dependent on proper location of the GT: thus, in some embodiments, the point probe is used to paint the GT to provide a high resolution view of the area. Similarly, in some embodiments, it may be useful to have a high-resolution view of the Lesser Trochanter (LT). For example, during hip arthroplasty, the Dorr Classification helps to select a stem that will maximize the ability of achieving a press-fit during surgery to prevent micromotion of femoral components post-surgery and ensure optimal bony ingrowth. As is generated understood in the art, the Dorr Classification measures the ratio between the canal width at the LT and the canal width 10 cm below the LT. The accuracy of the classification is highly dependent on the correct location of the relevant anatomy. Thus, it may be advantageous to paint the LT to provide a high-resolution view of the area.

In some embodiments, the point probe is used to paint the femoral neck to provide high-resolution data that allows the surgeon to better understand where to make the neck cut. The navigation system can then guide the surgeon as they perform the neck cut. For example, as understood in the art, the femoral neck angle is measured by placing one line down the center of the femoral shaft and a second line down the center of the femoral neck. Thus, a high-resolution view of the femoral neck (and possibly the femoral shaft as well) would provide a more accurate calculation of the femoral neck angle.

High-resolution femoral head neck data could also be used for a navigated resurfacing procedure where the software/hardware aids the surgeon in preparing the proximal femur and placing the femoral component. As is generally understood in the art, during hip resurfacing, the femoral head and neck are not removed: rather, the head is trimmed and capped with a smooth metal covering. In this case, it would be advantageous for the surgeon to paint the femoral head and cap so that an accurate assessment of their respective geometries can be understood and used to guide trimming and placement of the femoral component.

Registration of Pre-operative Data to Patient Anatomy using the Point Probe

As noted above, in some embodiments, a 3D model is developed during the pre-operative stage based on 2D or 3D images of the anatomical area of interest. In such embodiments, registration between the 3D model and the surgical site is performed prior to the surgical procedure. The registered 3D model may be used to track and measure the patient's anatomy and surgical tools intraoperatively.

During the surgical procedure, landmarks are acquired to facilitate registration of this pre-operative 3D model to the patient's anatomy. For knee procedures, these points could comprise the femoral head center, distal femoral axis point, medial and lateral epicondyles, medial and lateral malleolus, proximal tibial mechanical axis point, and tibial A/P direction. For hip procedures these points could comprise the anterior superior iliac spine (ASIS), the pubic symphysis, points along the acetabular rim and within the hemisphere, the greater trochanter (GT), and the lesser trochanter (LT).

In a revision surgery, the surgeon may paint certain areas that contain anatomical defects to allow for better visualization and navigation of implant insertion. These defects can be identified based on analysis of the pre-operative images. For example, in one embodiment, each pre-operative image is compared to a library of images showing "healthy" anatomy (i.e., without defects). Any significant deviations between the patient's images and the healthy images can be flagged as a potential defect. Then, during surgery, the surgeon can be warned of the possible defect via a visual alert on the display 125 of the CASS 100. The surgeon can then paint the area to provide further detail regarding the potential defect to the Surgical Computer 150.

In some embodiments, the surgeon may use a non-contact method for registration of bony anatomy intra-incision. For example, in one embodiment, laser scanning is employed for registration. A laser stripe is projected over the anatomical area of interest and the height variations of the area are detected as changes in the line. Other non-contact optical methods, such as white light inferometry or ultrasound, may alternatively be used for surface height measurement or to register the anatomy. For example, ultrasound technology may be beneficial where there is soft tissue between the registration point and the bone being registered (e.g., ASIS, pubic symphysis in hip surgeries), thereby providing for a more accurate definition of anatomic planes.

The present disclosure describes force-indicating devices and methods of using the same. By intraoperatively using the device, such as during the performance of a TKA, a measure of the amount of force applied to the knee joint during a joint laxity assessment may be quantified. Furthermore, a surgeon or other medical professional conducting the joint laxity assessment during surgery may be able to apply a consistent amount of force to the joint in one or more directions of motion.

Figure 5A:
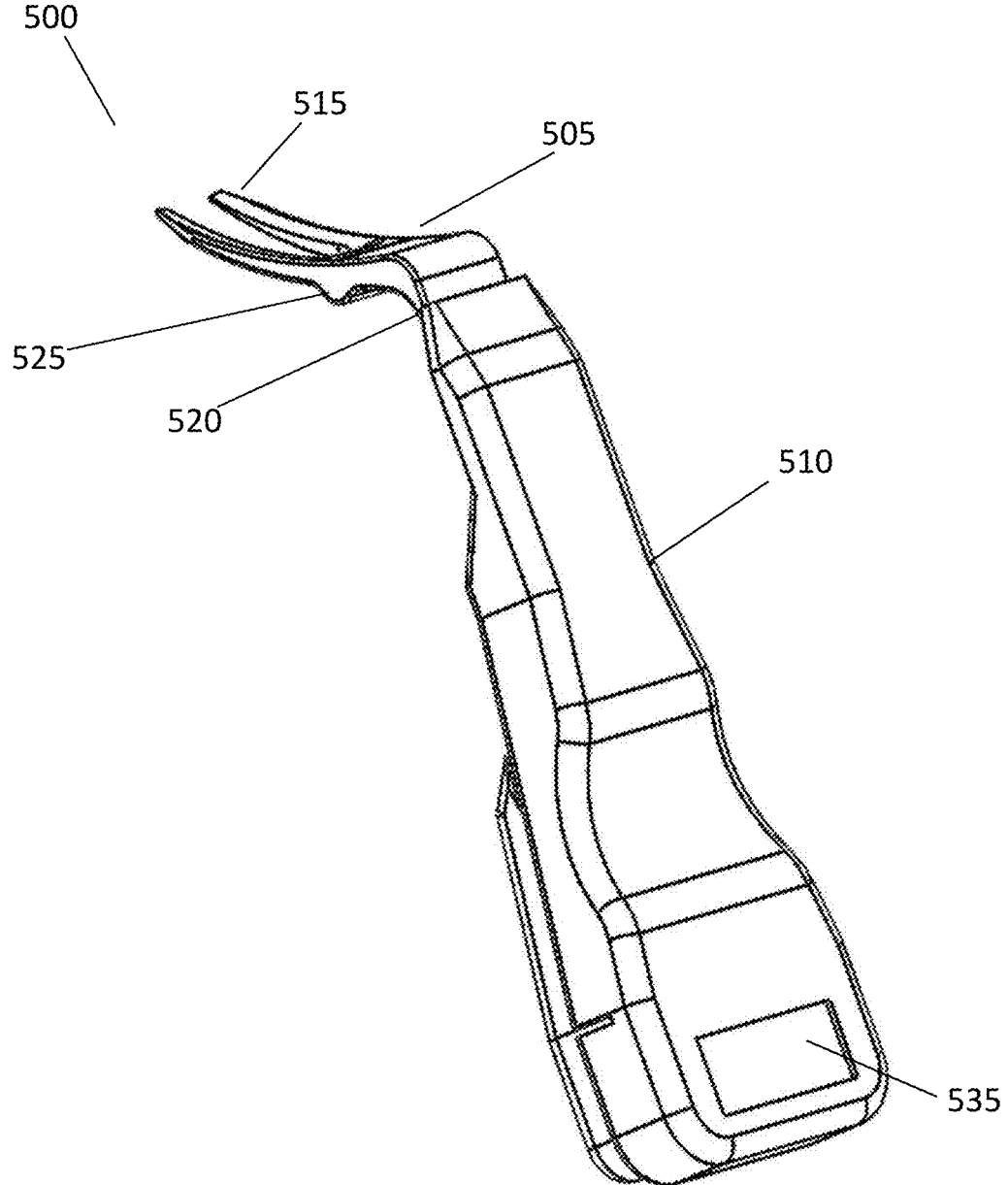
FIG. 5A depicts a perspective view of a device in accordance with an embodiment.

FIG. 5A depicts an illustrative device in accordance with an embodiment. As shown in FIG. 5A, the device 500 may include tissue retractor 505, a handle 510, and one or more force indicators 530) (in FIG. 5B). The tissue retractor may include an insertion end 515 and a base end 520. In an embodiment, the tissue retractor 505 may be bent so that the insertion end 515 and the base end 520 may be positioned at an angle relative to each other. In an embodiment, the angle may be an acute angle. In an embodiment, the angle may be an obtuse angle. In an embodiment, the angle may be a right angle. In an embodiment, the tissue retractor 505 may be straight so that the insertion end 515 and the base end 520 may be aligned along the same spatial plane. In an embodiment, the insertion end 515 of the tissue retractor 505 may be configured to be inserted between a condyle of a femur and a corresponding condyle of a tibia of a knee. In an alternative embodiment, the insertion end 515 of the tissue retractor 505 may be configured to be inserted between both condyles of a femur and both corresponding condyles of a tibia of a knee.

Figure 5B:
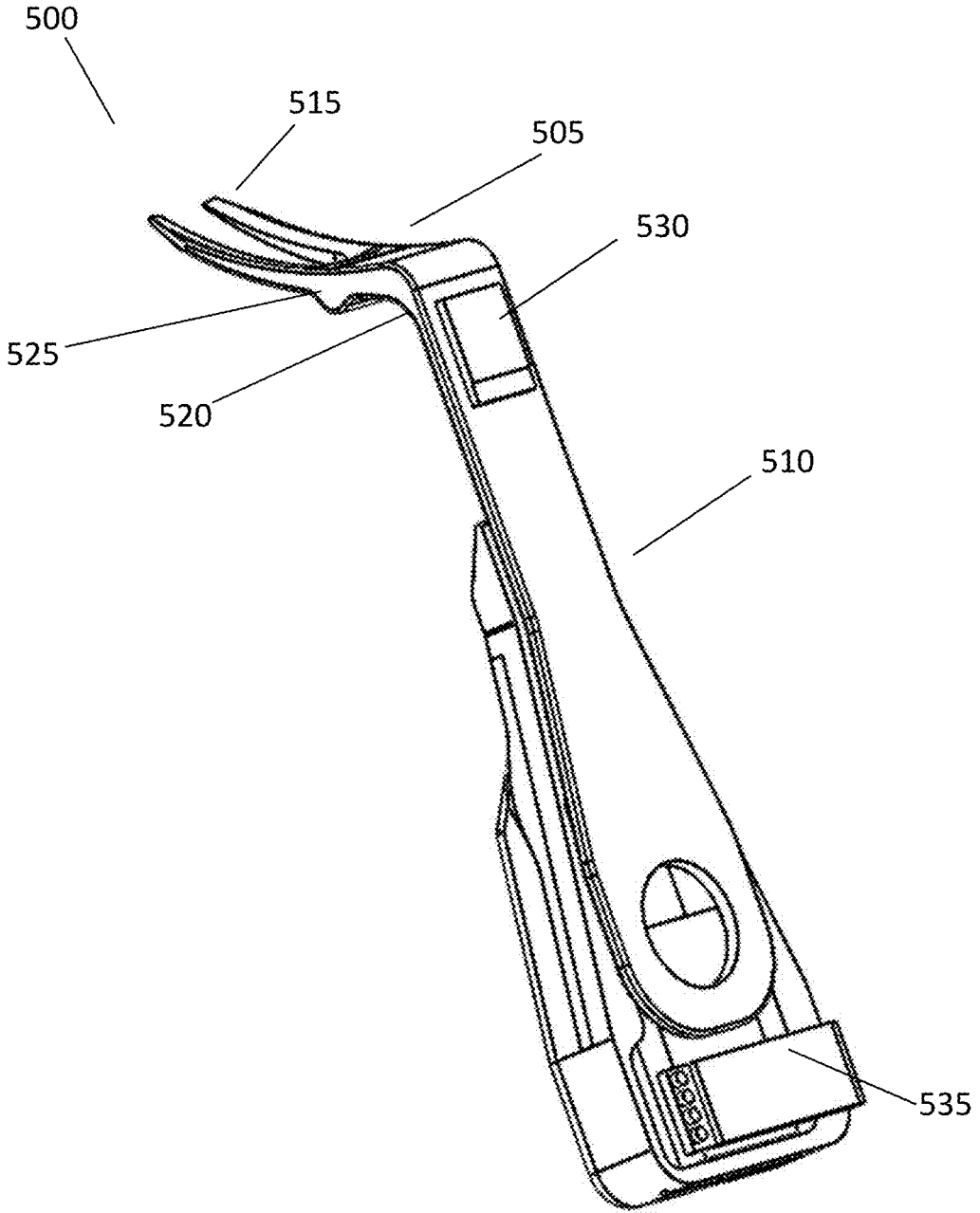
FIG. 5B depicts a perspective view of an alternative device in accordance with an embodiment.

FIG. 5B depicts an internal view of the illustrative device depicted in FIG. 5A. As illustrated in FIG. 5B, in an embodiment the one or more force indicators 530 may be located adjacent to the base end 520 of the tissue retractor 505. In an embodiment, the one or more force indicators 530 may be one or more strain gauges. In an embodiment, the one or more strain gauges may have a Wheatstone bridge configuration. In some embodiments, one or more pressure sensors or force indicators 530 may be located on the insertion end 515, the pivot feature 525, and/or the base end 520. In some embodiments, the device 500 may include an array of sensors or force indicators 530 to measure force values. In such embodiments, the force values measured by the sensors 530 may be averaged to provide a more accurate reading. Other sensors and/or other locations for such sensors will be apparent to those of ordinary skill in the relevant art.

In an embodiment, the tissue retractor 505 may further include a pivot feature 525 configured to concentrate stress forces at an existing bend in the tissue retractor 505. In an embodiment, the tissue retractor 505 may further include a pivot feature 525 configured to concentrate stress forces at a predetermined location on the tissue retractor 505. The base end 520 of the tissue retractor 505 may be connected to the handle 510. In an embodiment, the handle 510) may envelop a portion of the base end 520 of the tissue retractor 505. In an embodiment, the handle 510 may envelop the portion of the base end 520 on which the one or more force indicators 530 is located. In an embodiment the device 500 may include a converter (not shown) configured to convert analog force measurements into digital data. In an embodiment, the converter may include a signal amplifier (not shown).

Figure 5C:
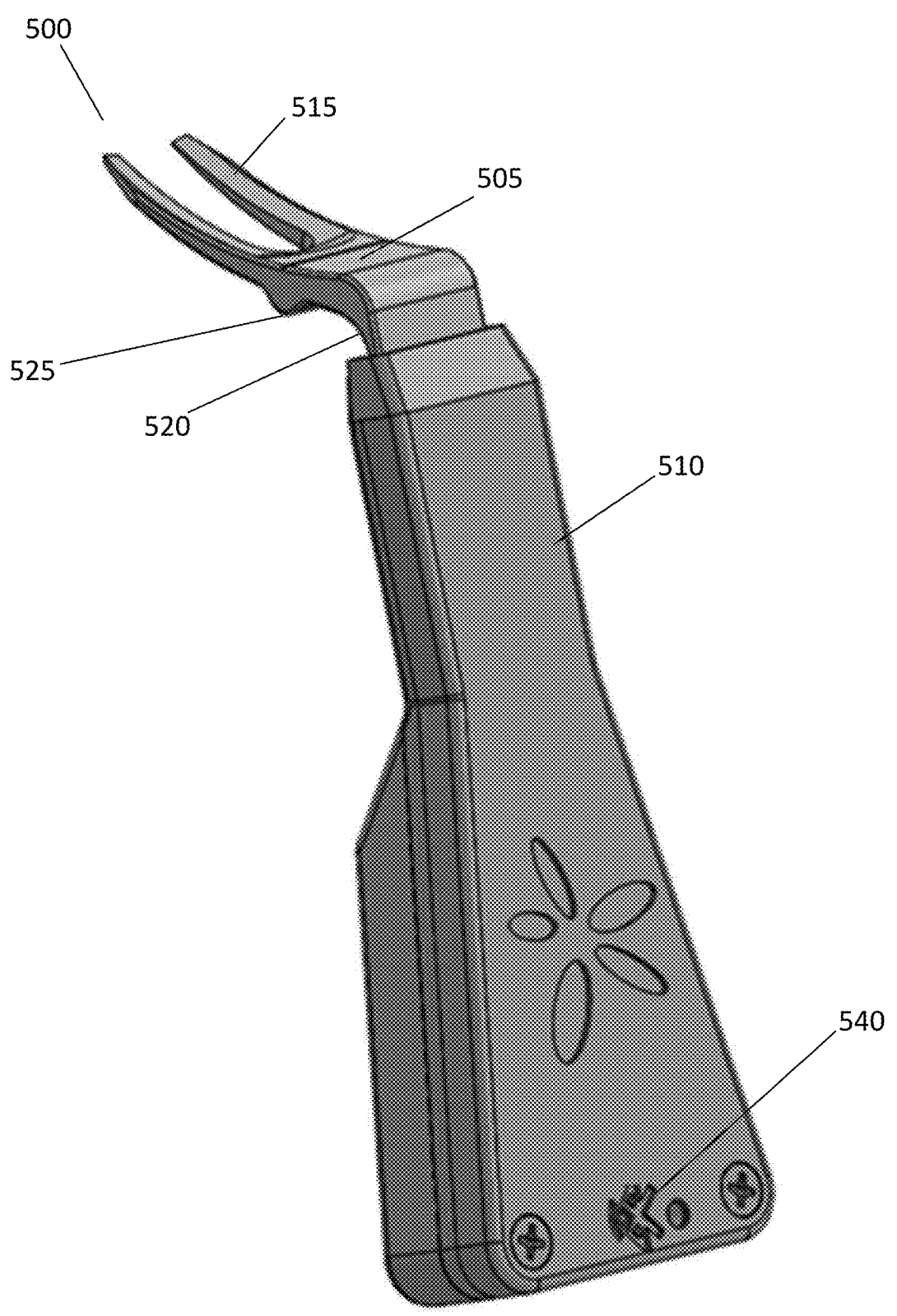
FIG. 5C depicts a perspective view of an alternative device in accordance with an embodiment.
Figure 5D:
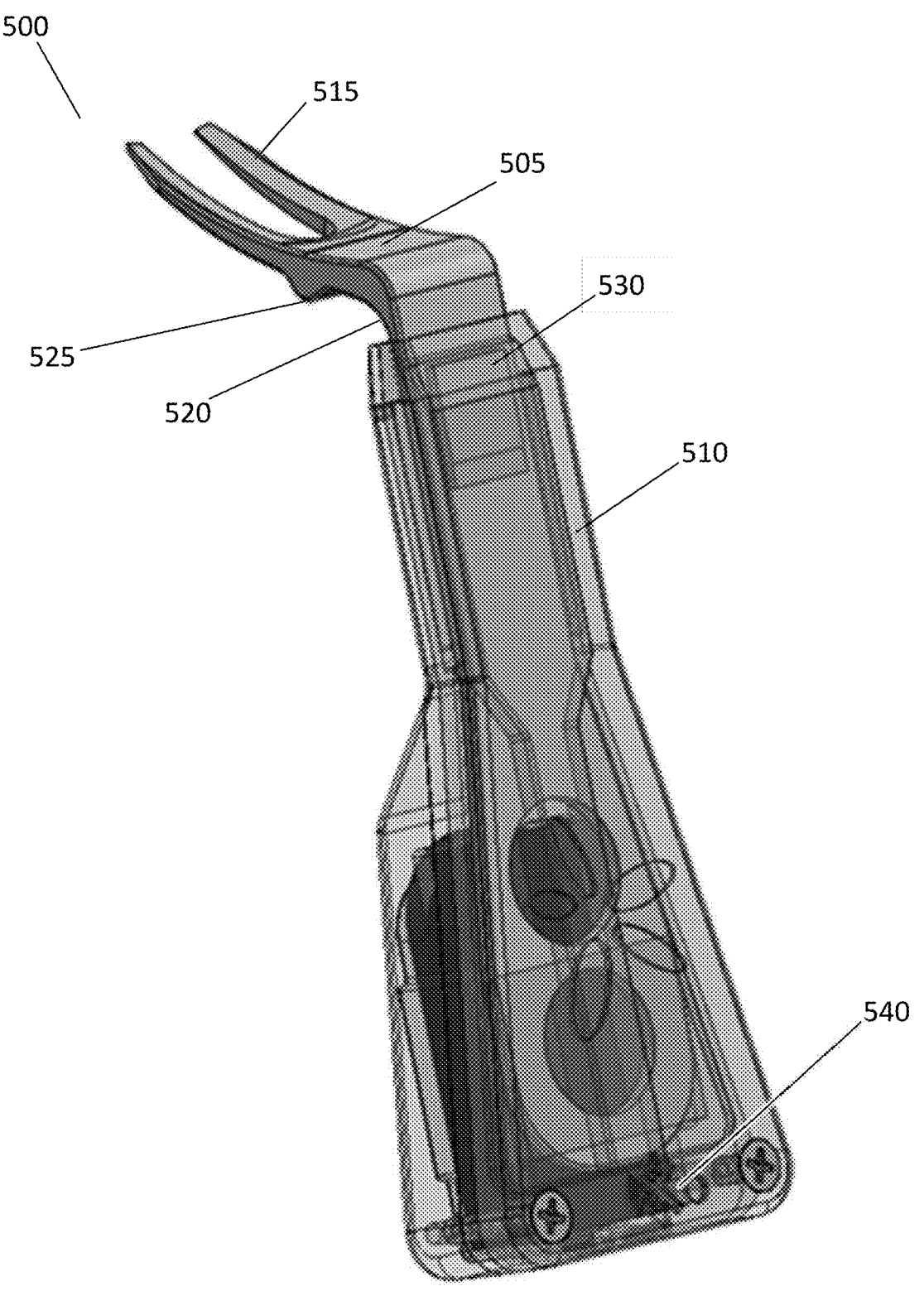
FIG. 5D depicts a transparent perspective view of the alternative device of FIG. 5C in accordance with an embodiment.
Figure 5E:
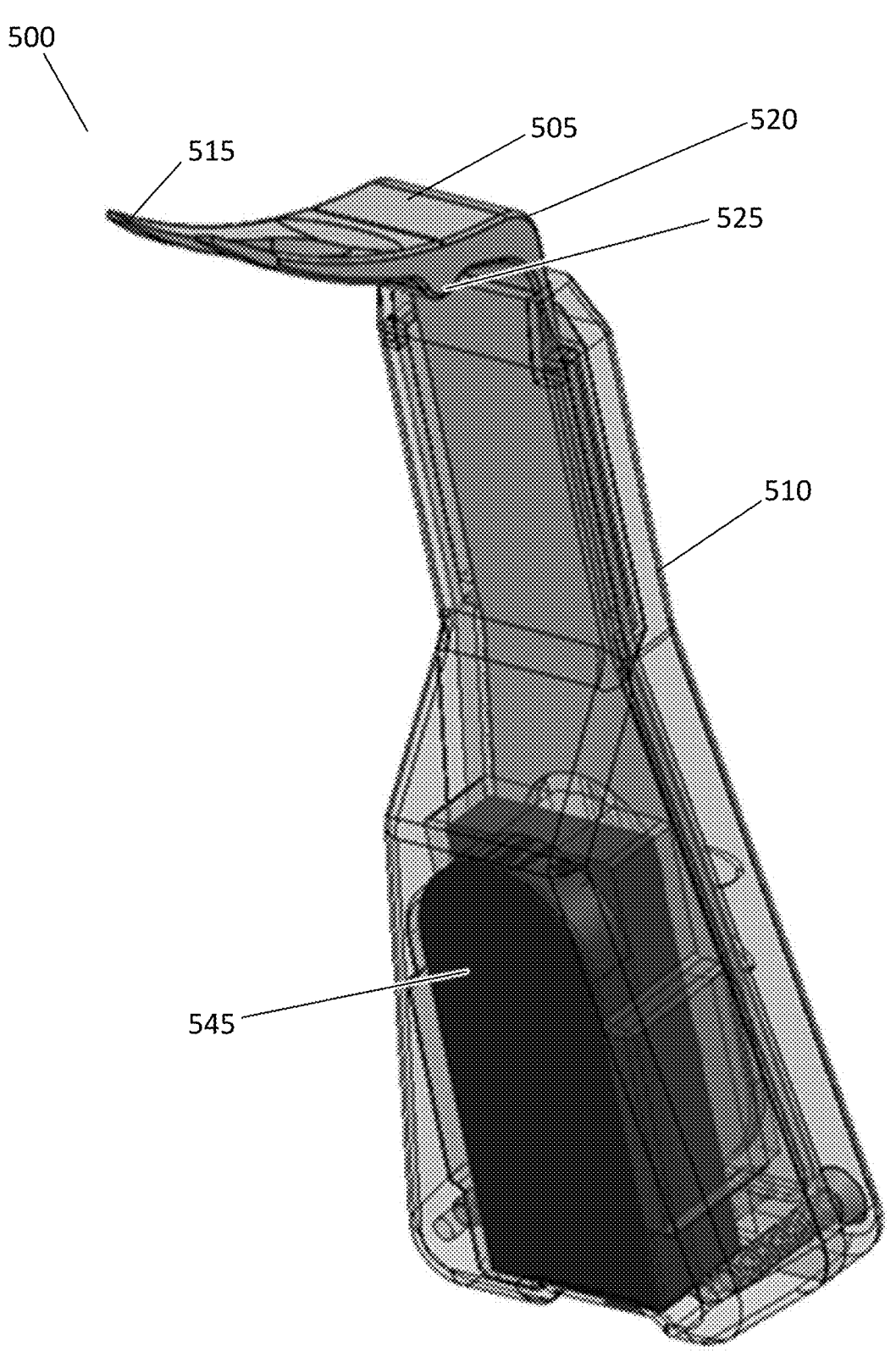
FIG. 5E depicts a second transparent perspective view of the alternative device of FIG. 5C in accordance with an embodiment.

As illustrated in FIGS. 5C. 5D, and 5E, in an additional or alternative embodiment, the device 500) may have wireless communication abilities. Accordingly, as shown in FIG. 5C, instead of a display 535, the device 500 may be marked 540) to indicate wireless connectivity. In a further embodiment, the device 500 may wirelessly communicate with one or more surgical navigation systems, such as the NAVIO® surgical navigation system. The direct transmission of the measured tension helps to reduce or eliminate potential user error, and removes the need for subjective ligament tensioning. In some embodiments, and as shown, the device 500 may still include the one or more force indicators 530, which may be located adjacent to the base end 520 of the tissue retractor 505.

Accordingly, in some embodiments, the handle 510 of the device 500 may house various components 545, such as, for example, a radio frequency (RF) module, an on board signal amplifier, a power supply, a microcontroller unit (MCU), an integrated circuit, and/or the like. Accordingly, as further discussed herein, the tensioning measured by the device 500, which may include, but is not limited to, a max force, a min force, an average force, the force over a period of time, a force angle, a force vector, etc. may be directly transmitted to a CASS to improve a surgical plan or on going surgical operation.

As illustrated in FIGS. 5A and 5B, the device 500 may include a display 535. In an embodiment, the display 535 may be in electronic communication with the one or more force indicators 530. The display 535 may display, for example, information pertaining to the force applied to the device 500. In an embodiment, the display 535 may be a digital display. In an embodiment, the force indicator 530 may be a digital force indicator with a display 535. In some embodiments, a digital force indicator 530 may be configured to record one or more measurements and provide at least one of such measurements to the display 535. For example, a digital force indicator 530 may be configured to record one or more of a minimum force measurement and a maximum force measurement. The minimum force measurement may be indicative of a minimum amount of force applied to the device 500 as the joint laxity is being tested. Similarly, the maximum force measurement may be indicative of a maximum amount of force applied to the device 500 as the joint laxity is being tested. Additional and/or alternate measurements may be recorded by a digital force indicator 530 within the scope of this disclosure. In any of these embodiments, the force indicator 530 may be configured to electronically record an amount of force applied to the portion of the body and transmit the recording of the amount of force to a computer.

In an embodiment, the device 500 may further include a power source (not shown). In an embodiment, the power source may be a power cord. In an alternative embodiment, the power source may be a wireless power source, including a fixed battery, a removable battery, a fluctuating magnetic field, a photovoltaic array, or any combination thereof.

In an embodiment, the device 500 may further include one or more location tracking devices (not shown). In an embodiment, the one or more location tracking devices may be optical tracking arrays. In an embodiment, the one or more location tracking devices may be fixedly attached to the device 500. In an embodiment, the one or more location tracking devices may be removably attached to the device 500. In an embodiment, the device 500 may include one or more attachment features configured to receive the one or more location tracking devices in a fixed manner. In an embodiment, the device 500 may include one or more attachment features configured to receive the one or more location tracking devices in a removable manner.

In some embodiments, the one or more location tracking devices may be configured to record one or more location data points indicating one or more of the location, orientation, and motion of the device 500 and provide at least one of these data points to a computer. In an embodiment, the one or more location tracking devices may be configured to record one or more location data points as the device 500 is moved that may be indicative of a linear motion of the device or one or more components thereof. In an embodiment, the one or more location tracking devices may be configured to record one or more location data points as the device 500 is moved in a manner that may be indicative of a rotational motion of the device or one or more components thereof. In an embodiment, the one or more location tracking devices may be configured to record one or more location data points as the device 500 is moved that may be indicative of a twisting of the device or one or more components thereof.

In an embodiment, the one or more location tracking devices may be configured to record one or more location data points as the device 500 is moved that may be indicative of a bending of the device or one or more components thereof. In some embodiments, the one or more tracking devices may comprise a displacement sensor, such as a reflective sensor, a LED position sensor, a piezo effect sensor, a Hall effect sensor, an inductive sensor, a microelectromechanical systems (MEMS) sensor, a piezo-resistive sensor, a load sensor, an ultrasonic resonator in conjunction with a compressible propagation structure, a capacitive sensor, a temperature sensor, or the like.

Figure 5F:
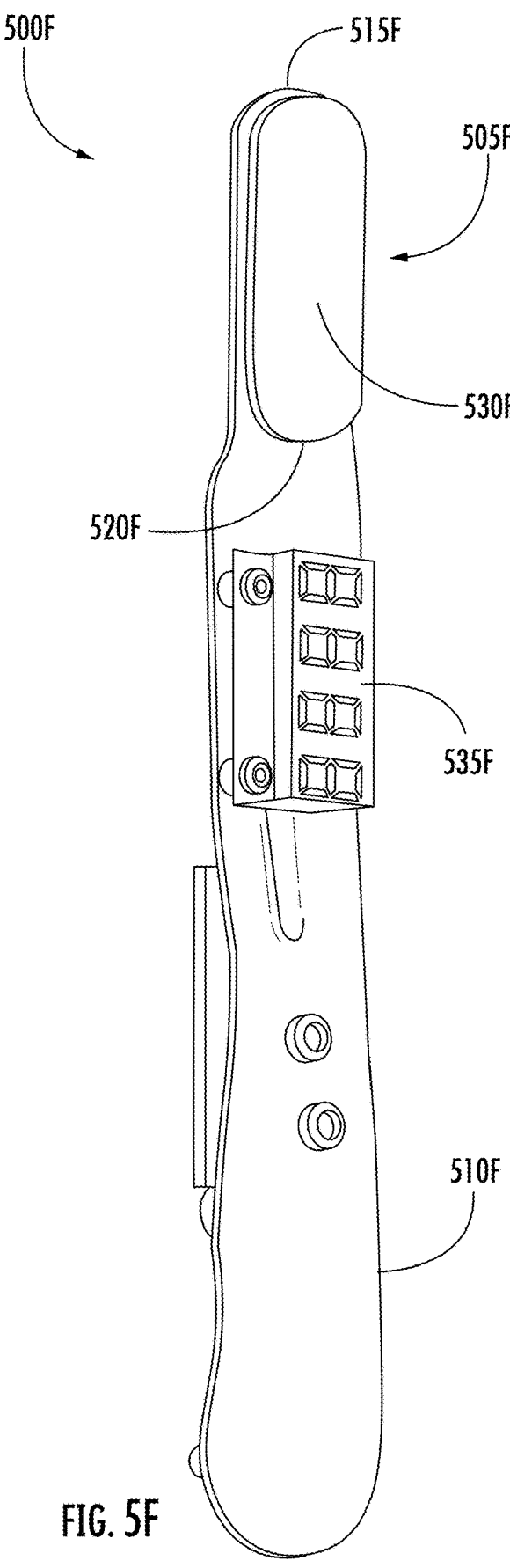
FIG. 5F depicts a top view of an alternative device in accordance with an embodiment.

FIG. 5F depicts an illustrative device in accordance with an alternate embodiment. As illustrated in FIG. 5F, the device 500F may include a tissue retractor 505F, a handle 510F, and one or more force indicators 530F. The tissue retractor may include an insertion end 515F and a base end 520F. In an embodiment, the device 500F may have one or more force indicators 530F located on the insertion end 515F of the tissue retractor 505F. In an embodiment, the one or more force indicators 530F may include a pressure sensor, such as a piezo effect sensor. Other pressure sensors will be apparent to those of ordinary skill in the relevant art. In an embodiment, the device 500F may have a display 535F. In an embodiment, the insertion end 515F of the tissue retractor 505F may include a paddle sized and shaped to be inserted between a condyle of a femur and a corresponding condyle of a tibia of a knee. In an alternative embodiment, the insertion end 515F of the tissue retractor 505F may include a plurality of paddles sized and shaped to be inserted between the condyles of a femur and the corresponding condyles of a tibia of a knee. In some embodiments, the device 500F may include an array of force indicators 530F. In such embodiments, the force values measured by the force indicators may be averaged to provide a more accurate reading.

FIGS. 6A, 6B, 6C, and 6D depict an illustrative device in accordance with another alternate embodiment. As illustrated in FIGS. 6A, 6B, 6C, and 6D, the device 600) may include a tissue retractor 605 with a first prong 615 having an insertion end 620 and a base end 625, a second prong 630 having an insertion end 635 and a base end 640, at least two handles 645 and 650, and one or more force indicators arranged around a rotational joint 660. A rotational spring is wrapped around the rotational joint 660. In an embodiment, the rotational spring may be a torsion spring. The first prong 615 and second prong 630 of the tissue retractor 605, the at least two handles 645 and 650, and the rotational spring are configured so that the first prong 615 and the second prong 630 of the tissue retractor 605 may pivot around the rotational joint 660 when a force is applied to the at least two handles 645 and 650.

In an embodiment, the one or more force indicators are configured to trigger when the at least two handles 645 and 650 reach a displacement point relative to each other at which a predetermined torque is achieved. In an embodiment, the one or more force indicators are one or more electrical or magnetic sensors, such as a piezo effect sensor, a Hall effect sensor, an inductive sensor, or any combination thereof. In some embodiments, the one or more force indicators include one or more of the following sensors: a microelectromechanical systems (MEMS) sensor, a piezo-resistive sensor, a load sensor, an ultrasonic resonator in conjunction with a compressible propagation structure, a capacitive sensor, and/or a temperature sensor. Other pressure sensors will be apparent to those of ordinary skill in the relevant art. In some embodiments, the device 600 may include an array of force indicators. In such embodiments, the forces measured by the force indicators may be averaged to provide a more accurate reading of an applied force.

Figure 6A:
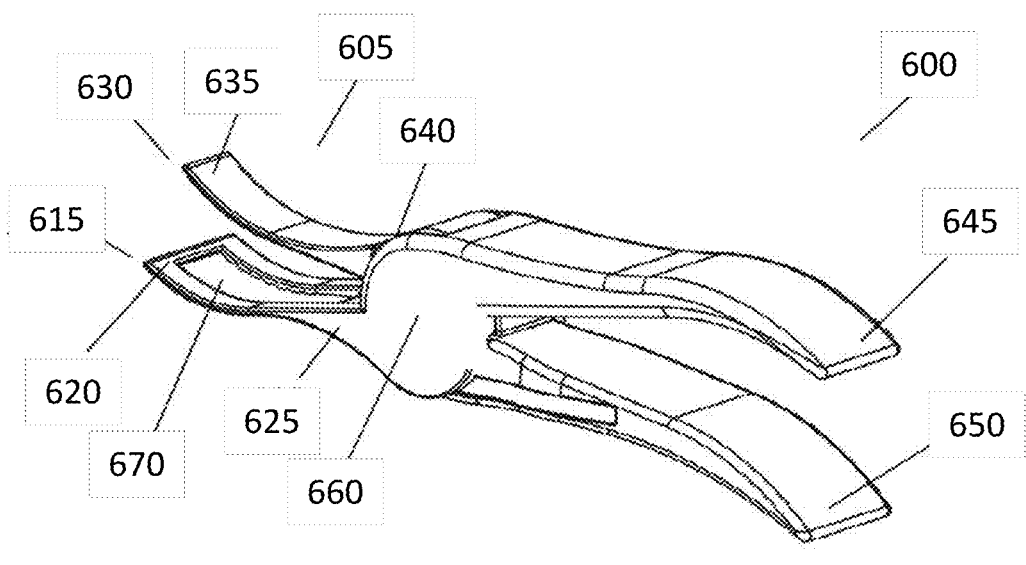
FIG. 6A depicts a perspective view of an alternative device in accordance with an embodiment.
Figure 6B:
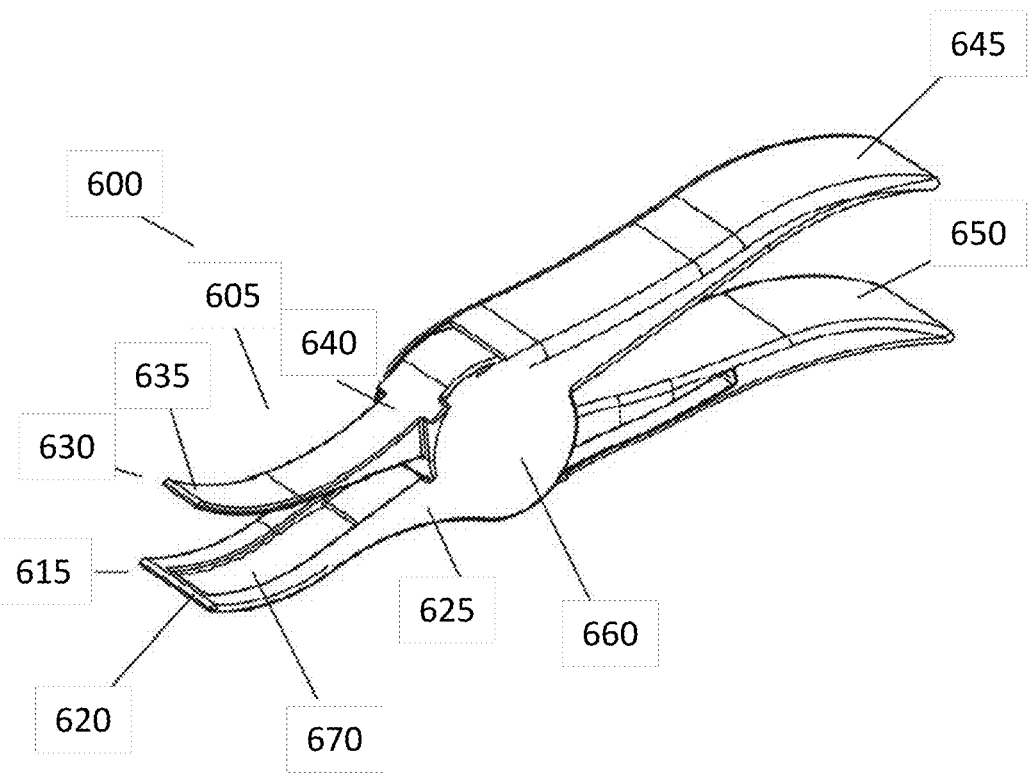
FIG. 6B depicts another perspective view of an alternative device in accordance with an embodiment.
Figure 6C:
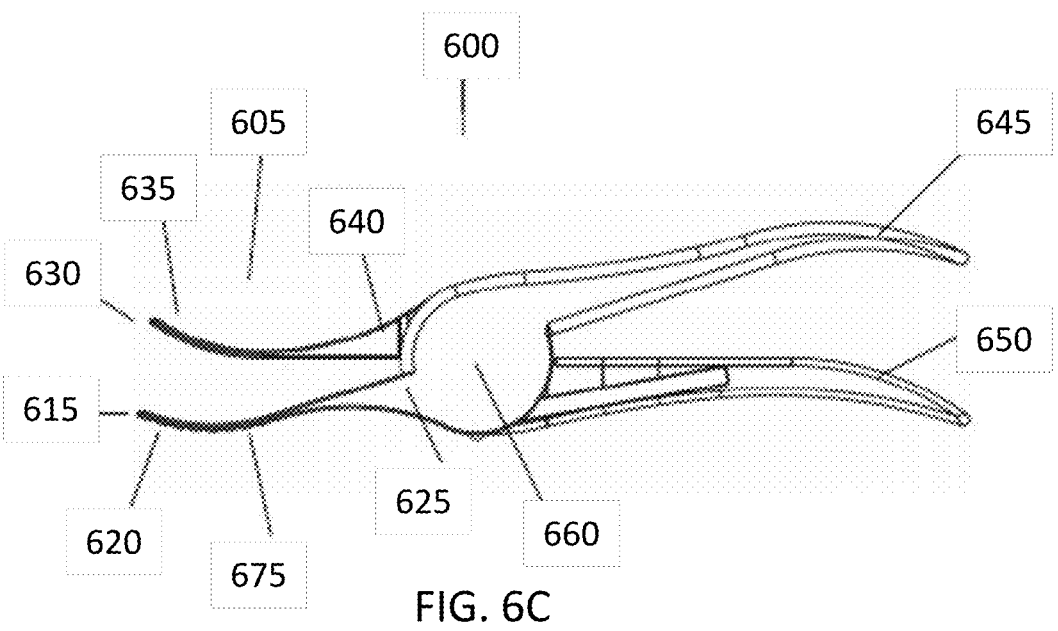
FIG. 6C depicts a side view of an alternative device in accordance with an embodiment.

As shown in FIGS. 6A, 6B, and 6C, in an embodiment, the first prong 615 and second prong 630 of the tissue retractor 605 are separated in an open position when the rotational spring is in its neutral position and fit together in a closed position when a force is applied to the at least two handles 645 and 650. In an alternative embodiment, the first prong 615 and the second prong 630 of the tissue retractor 605 fit together in a closed position when the rotational spring is in a neutral positon and separate to an open position when a force is applied to the at least two handles 645 and 650. In an embodiment, the first prong 615 and the second prong 630 of the tissue retractor 605 are sized and shaped to rest against each other when in a closed position.

In an embodiment, one or more of the insertion end 620 of the first prong 615 and the insertion end 635 of the second prong 630 of the tissue retractor 605 may include one paddle sized and shaped to be inserted between a condyle of a femur and a corresponding condyle of a tibia in a knee.

In an alternative embodiment, one or more of the insertion end 620 of the first prong 615 and the insertion end 635 of the second prong 630 of the tissue retractor 605 may include a plurality of paddles sized and shapes to be inserted between the condyles of a femur and the corresponding condyles of a tibia in a knee. In an embodiment, as shown in FIGS. 6A and 6B, the first prong 615 may further include a cavity 670 having a size and shape corresponding to the size and shape of at least a portion of the second prong 630, such that the portion of the second prong sits within the first prong when the first prong and the second prong are in a closed position.

Figure 6D:
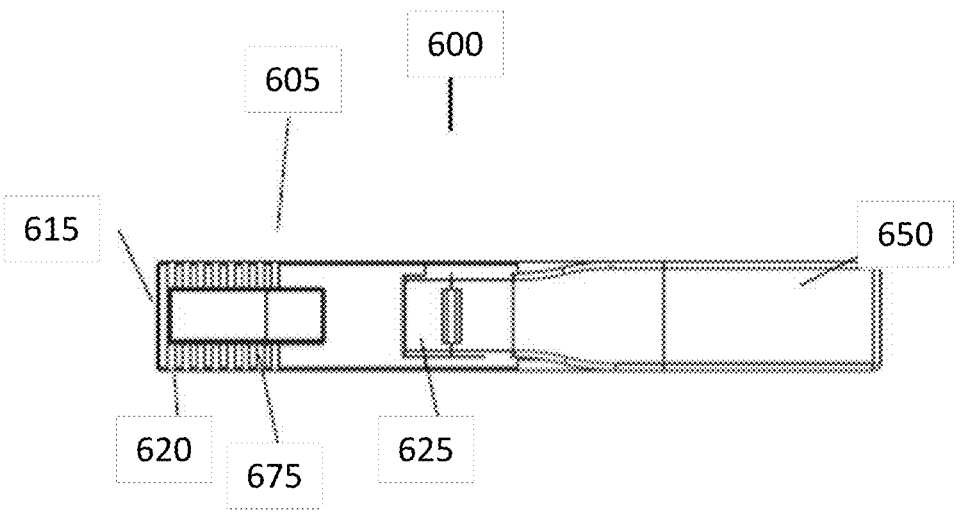
FIG. 6D depicts a top view of an alternative device in accordance with an embodiment.

In an embodiment, one or more of the insertion end 620 of the first prong 615 and the insertion end 635 of the second prong 630 of the tissue retractor 605 include an articular-facing surface configured to engage with the articular surfaces of a joint when the insertion end of the first prong and the insertion end of the second prong are inserted in the joint. In an embodiment, one or more of the articular-facing surfaces of the insertion end 620 of the first prong 615 and the insertion end 635 of the second prong 630 further include one or more engagement features 675 configured to engage the articular surfaces of the joint. In an embodiment, as shown in FIGS. 6C and 6D, only the articular-facing surface of the insertion end 620 of the first prong 615 may include the one or more engagement features 675.

Figure 7A:
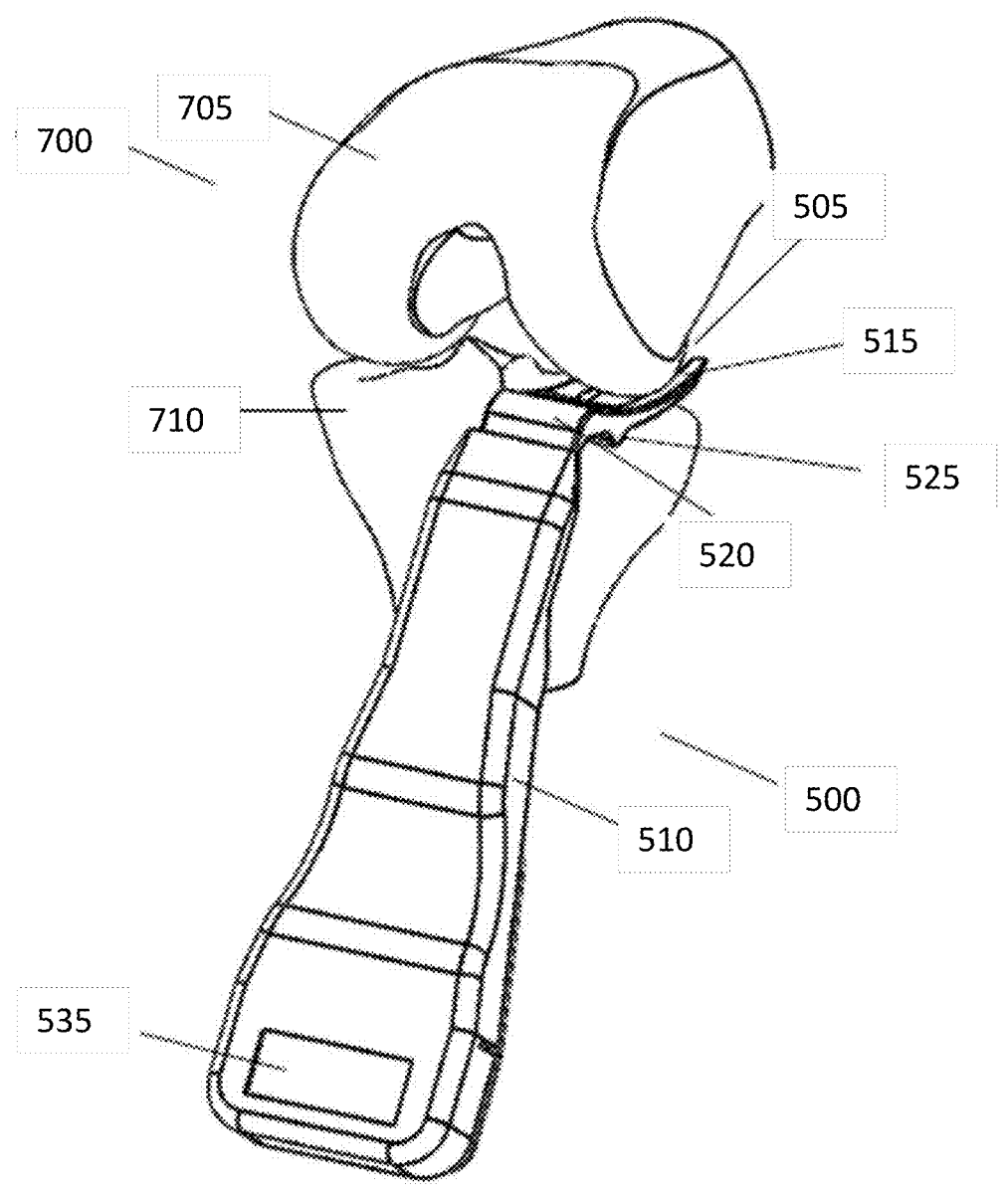
FIG. 7A depicts a perspective view of a device inserted into a patient knee in accordance with an embodiment.
Figure 7B:
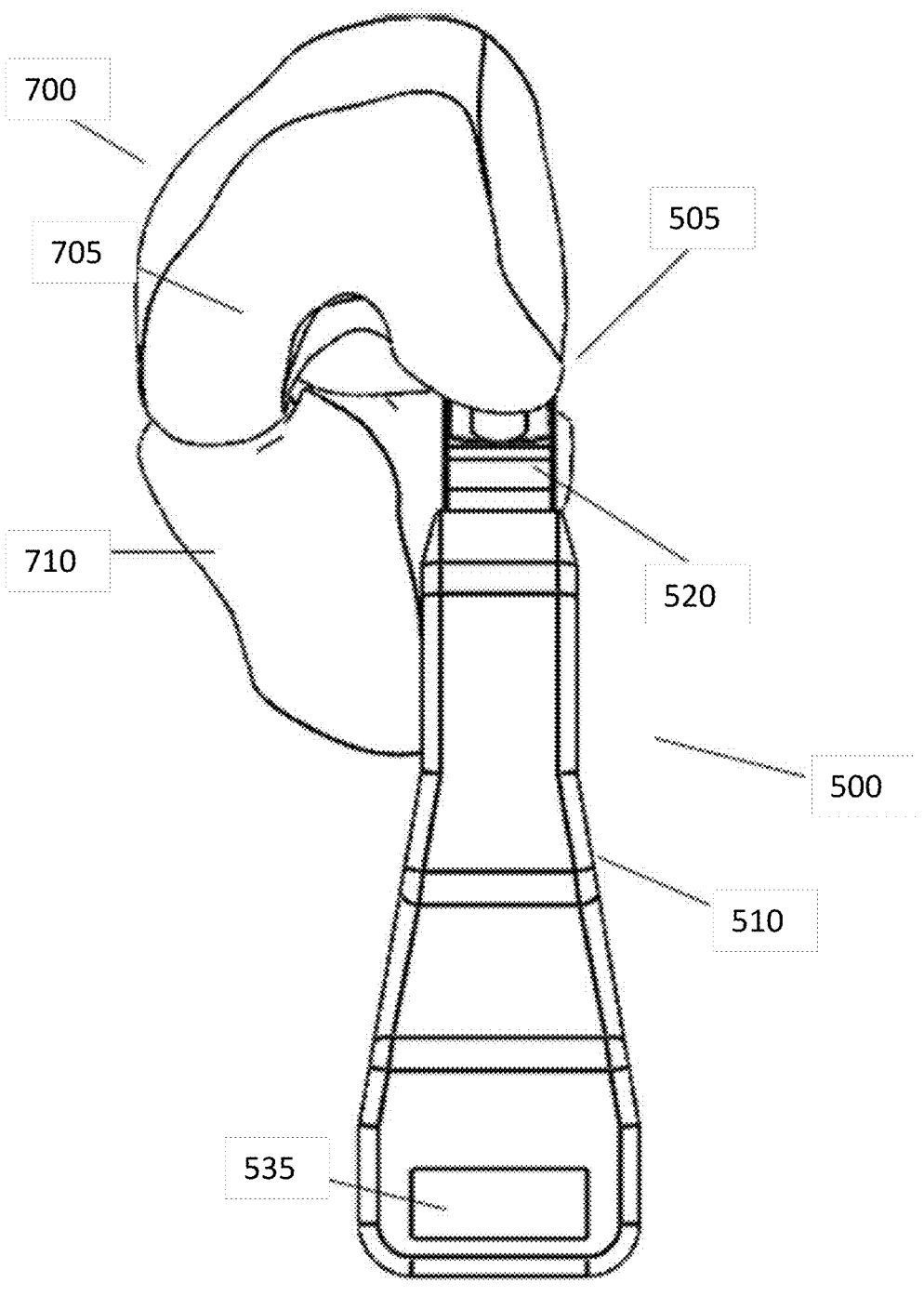
FIG. 7B depicts a front view of a device inserted into a patient knee in accordance with an embodiment.

FIGS. 7A and 7B depict the illustrative device of FIGS. 5A and 5B inserted in a knee joint in accordance with an embodiment. In an embodiment, the force applied to the handle 510 of the device 500 distal from the insertion point may cause an existing bend in the tissue retractor 505 to further bend. In an embodiment, the force applied to the handle 510 of the device 500 distal from the insertion point may be concentrated in a predetermined location by the pivot feature 525. As shown in FIGS. 7A and 7B, the insertion end 515 of the tissue retractor 505 may be sized and shaped to be inserted between one condyle of a femur and one corresponding condyle of a tibia of a knee. In an embodiment, an insertion end 515 of the tissue retractor 505 of the device 500 may be inserted between the medial condyle of the femur 705 and the medial condyle of the tibia 710 of a patient's knee 700. In an alternative embodiment, the insertion end 515 of the tissue retractor 505 may include a plurality of paddles sized and shaped to be inserted between both condyles of a femur and both corresponding condyles of a tibia of a knee.

Figure 8A:
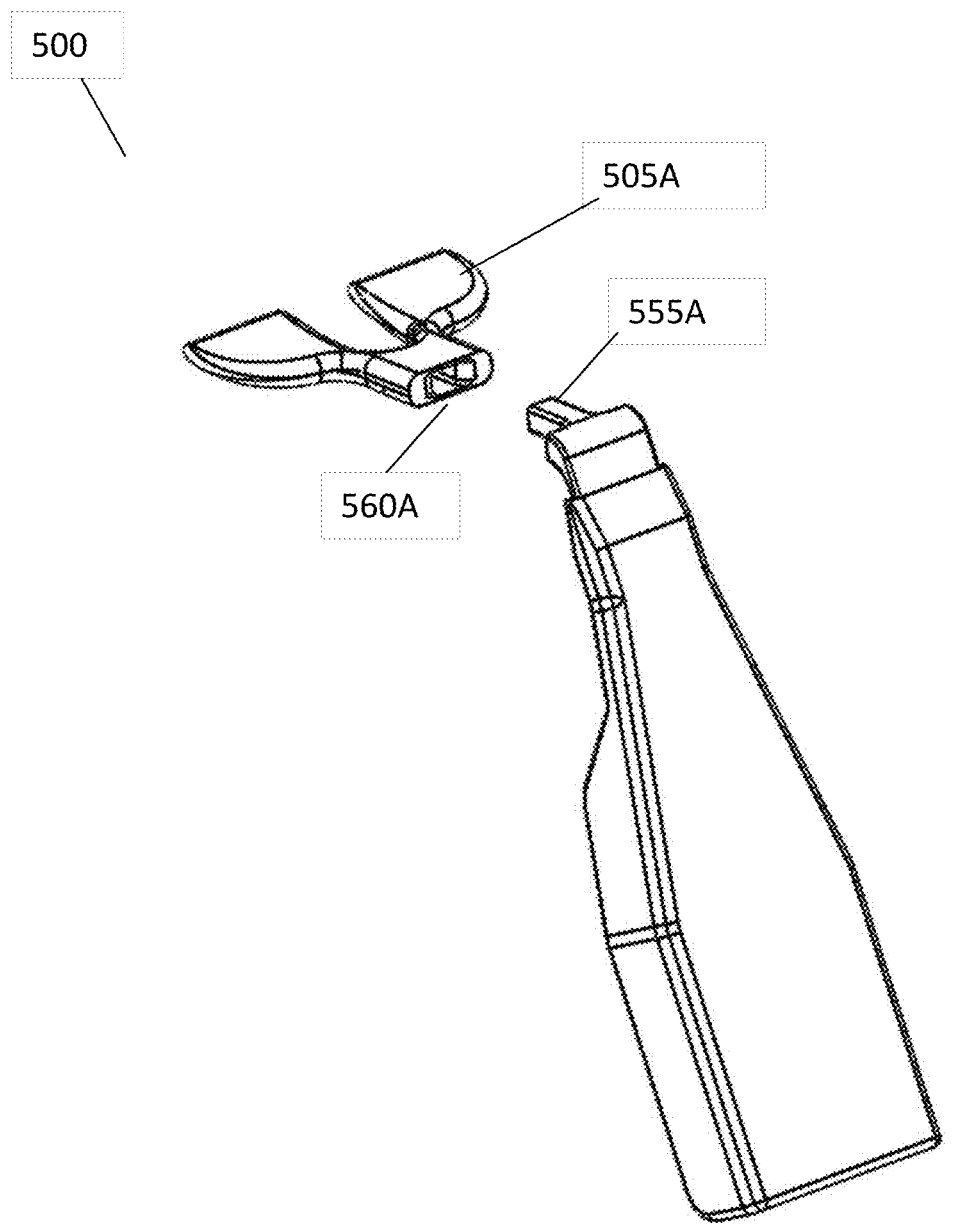
FIG. 8A depicts a perspective view of a device with modifiable tip in accordance with an embodiment.
Figure 8B:
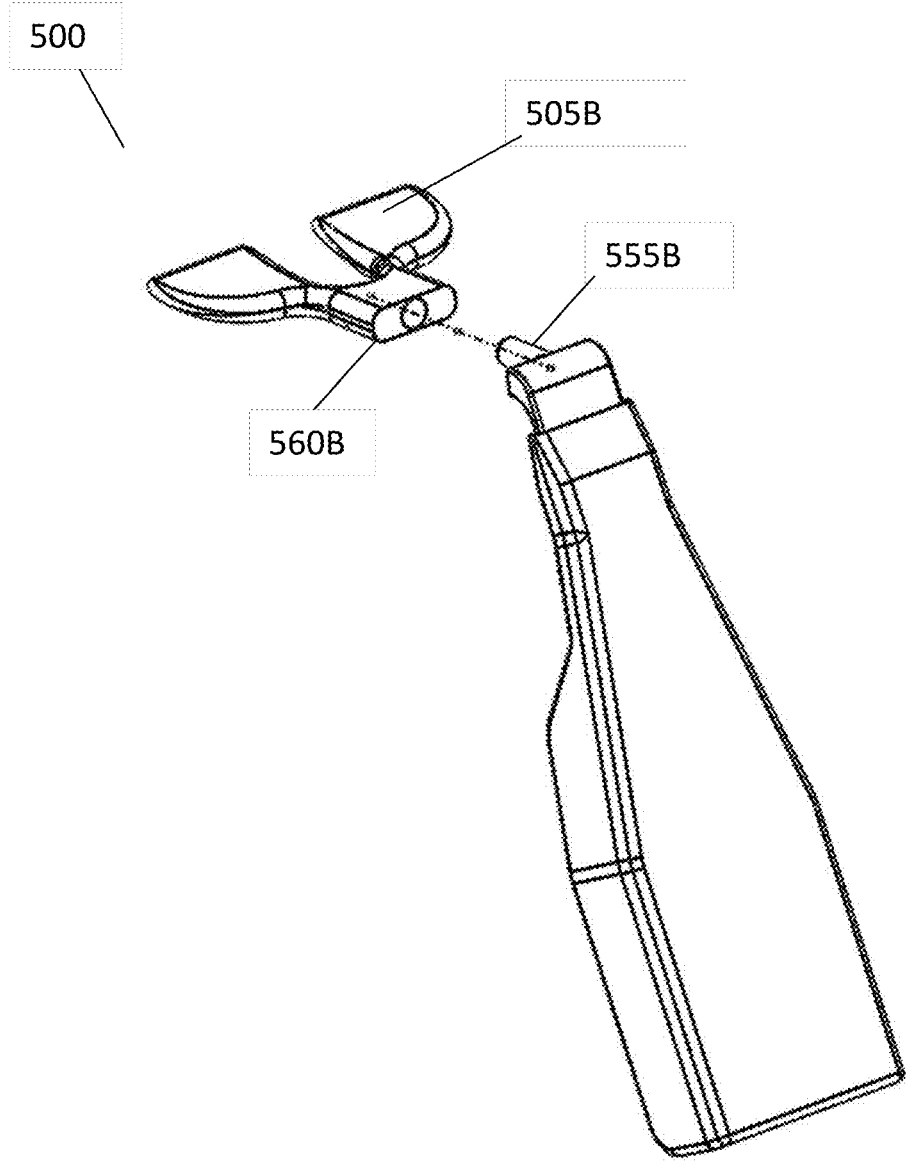
FIG. 8B depicts a perspective view of an alternative device with modifiable tip in accordance with an embodiment.
Figure 8C:
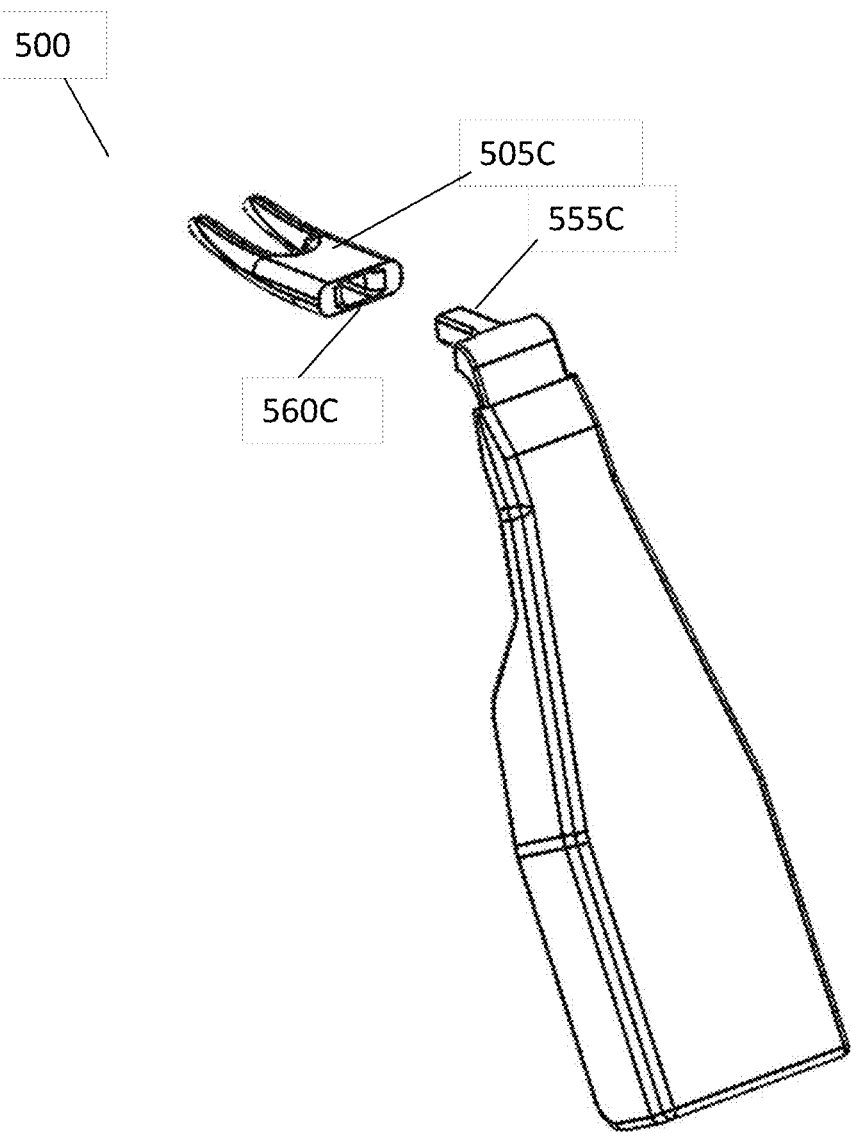
FIG. 8C depicts a perspective view of an alternative device with modifiable tip in accordance with an embodiment.

Referring now to FIGS. 8A-8C, further embodiments may exist in which the original tissue retractor (FIG. 5, 505) is removable and replaceable. As shown in FIG. 8A, the device 500 may have an alternate tissue retractor 505A. In some embodiments, the device 500 may have a protrusion 555A that is complementary to one or more a recesses 560A within the new tissue retractor 505A. It should be understood that the coupling mechanism between the device 500 and the alternate tissue retractor 505A may be by any means capable of securing the alternative tissue retractor in place (e.g., mechanical coupling, magnetic coupling, electromagnetic coupling, etc.). In an additional or alternative embodiment, the protrusion 555A, 555B, 555C and recess 560A, 560B, 560C may have one of a variety of complementary shapes, such as, for example, 555A versus 555B, in which the protrusion and recess have rounded corners. Moreover, it should be understood that various other shapes may be utilized, such as an octagon, star, etc.

In a further embodiment, the tissue retractor 505A, 505B, 505C may be of various shapes, sizes, orientations, etc. based on the need of the tensioning device. For example, the tissue retractor may be utilized for any type of tensioning requirement related, but not limited to, knee surgery, hip surgery, spinal surgery, etc.

Figure 9:
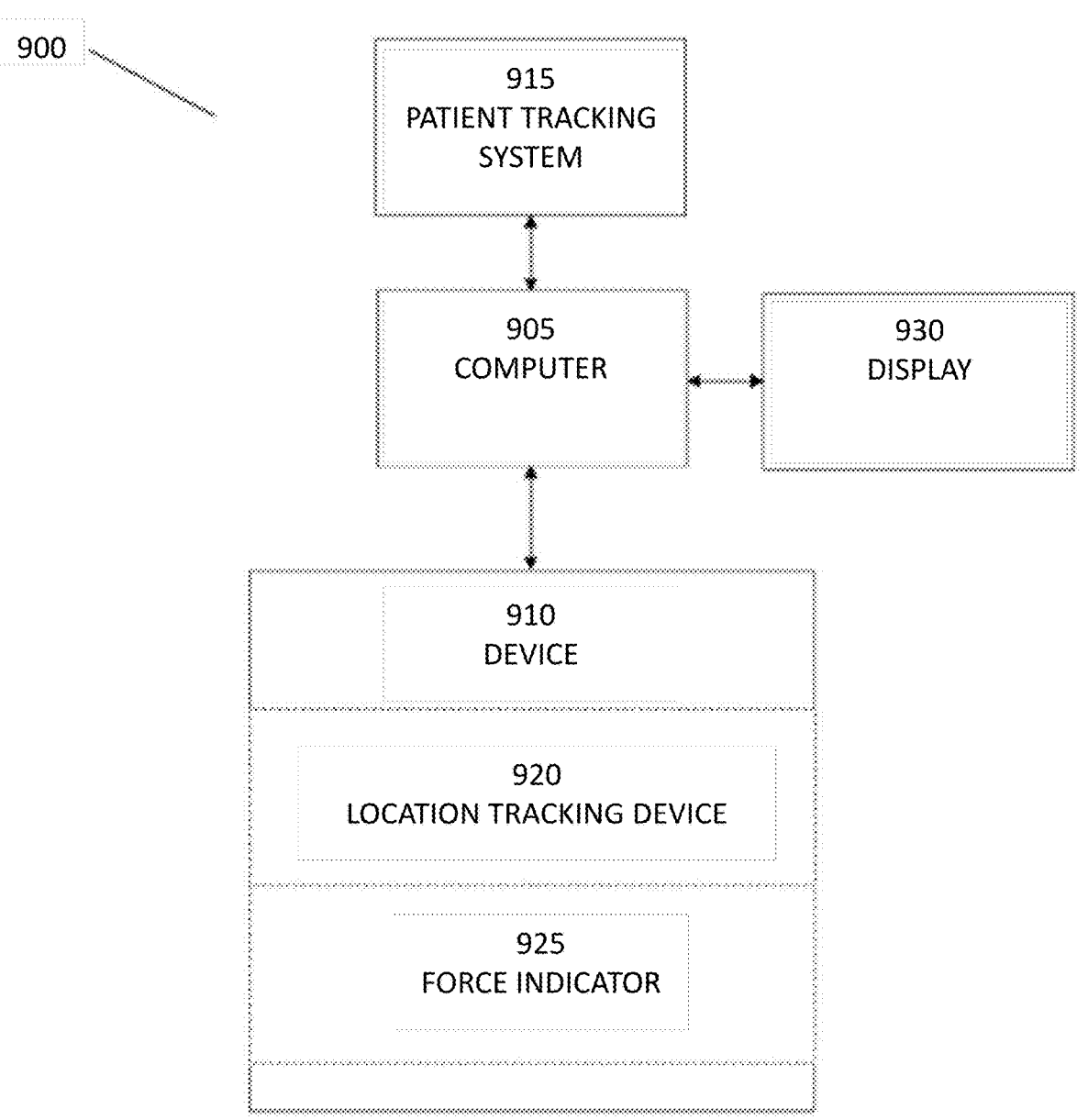
FIG. 9 depicts an illustrative flow diagram for measuring a force applied to a joint during a surgical procedure in accordance with an embodiment.

FIG. 9 depicts a block diagram of an illustrative system for measuring a force applied to a joint during a surgical procedure in accordance with an embodiment. As shown in FIG. 9, the system 900 may include a computer 905, a device 910, and a patient tracking system 915. The device 910 may include one or more location tracking devices 920. The one or more location tracking devices 920 may be optical tracking arrays. The device 910 may further include one or more force indicators 925. The system 900 may include more or fewer components in certain examples. For example, the system 900 may not include a patient tracking system 915 or a location tracking device 920 in some embodiments.

In an embodiment, the computer 905 is in electronic communication with device 910. In an embodiment, the computer 905 is a robotic surgical system. In an embodiment, the computer 905 is a surgical system. In an embodiment, the computer 905 is in electronic communication with the one or more location tracking devices 920. In an embodiment, the computer 905 is in electronic communication with the one or more force indicators 925. In an embodiment, the electronic communication may be wired. In an embodiment, the electronic communication may be performed using a wireless transmission system. The wireless transmission system may receive information from the one or more location tracking devices 920 and convert the information into digital information that may be wirelessly transmitted to the computer 905. The wireless transmission system may further receive information from the one or more force indicators 925 and convert the information into digital information that may be wirelessly transmitted to the computer 905.

In an embodiment, the robotic surgical system 900 is additionally in electronic communication with a patient tracking system 915. In an embodiment, the electronic communication may be wired. In an embodiment, the electronic communication may be performed using a wireless transmission system. The wireless transmission system may receive information from the patient tracking system 915 and convert the information into digital information that may be wirelessly transmitted to the computer 905. In an embodiment, the patient tracking system 915 is configured to be attached to one or more portions of the patient's anatomy into which the device 910 is inserted to improve the accuracy of the measurements obtained using the device.

In an embodiment, the patient tracking system 915 includes one or more trackers 930. In an embodiment, the one or more trackers 930 may be optical tracking arrays. In an embodiment, the one or more trackers 930 are configured to record one or more location data points indicating one or more of the location, orientation, and motion of the device and provide at least one of these data points to the computer 905. The one or more trackers 930 can be attached to one or more of the patient's tibia and femur. In an embodiment, the one or more trackers 930 may be attached to each of the patient's tibia and femur and may be configured to record one or more location data points that may be indicative of the relative orientation of the tibia and femur as the device 910 is inserted between the patient's tibia and femur and moved, for example as a force is applied to the handle of the device. In an embodiment, the relative orientation of the tibia and femur is the location of the tibia and femur. In an embodiment, the relative orientation of the tibia and femur is the distance between the tibia and femur. In an embodiment, the relative orientation of the tibia and femur is the angle between the tibia and femur relative to one or more of the distal-proximal axis, the anterior-posterior axis, and the medial-lateral axis. In an embodiment, the relative orientation of the tibia and femur is a flexion angle of the tibia and femur.

In an embodiment, the computer 905 is configured to receive data from the device 910, or one or more of its components, the one or more location tracking devices 920 and the one or more force indicators 925. In an embodiment, the computer 905 is configured to receive data from the patient tracking system 915.

Figure 10A:
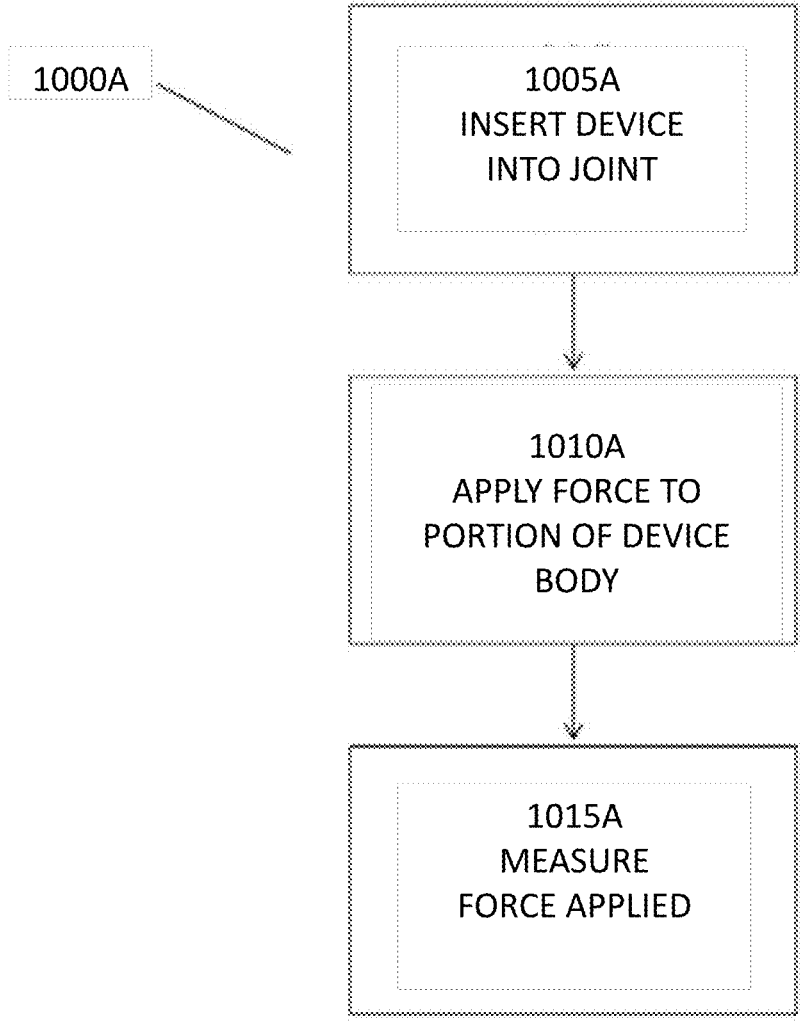
FIG. 10A depicts another illustrative flow diagram for measuring a force applied to a joint during a surgical procedure in accordance with an embodiment.

FIG. 10A depicts a flow diagram 1000A of an illustrative method of measuring a force applied to a joint during a surgical procedure in accordance with an embodiment. As shown in FIG. 10A, a device may be inserted 1005A into a portion of a joint, a force may be applied to the device 1010A, and the applied force may be measured 1015A. In some embodiments, the joint may be a knee. However, the device may be inserted 1005A into other joints, such as a shoulder, an elbow; an ankle, a hip, or the like, within the scope of this disclosure. The device to be inserted may include a tissue retractor having an insertion end and a base end, a handle, and one or more force indicators, such as the devices described further herein.

In an embodiment, the force may be applied 1010A to the handle of the device that is distal from the joint. Applying the force in this manner may cause displacement of the insertion end of the tissue retractor relative to the base end, as described further herein. In an embodiment, the applied force may be measured 1015A by the one or more force indicators. In an embodiment, the one or more force indicators may be configured to record an amount of force applied to the portion of the joint electronically. In an embodiment, the one or more force indicators may be configured to electronically record an amount of force applied to the portion of the body and transmit the recording of the amount of force to a computer, including a robotic surgical system or a surgical system.

In an alternative embodiment, applying the force 1010A to the handle of the device may cause displacement of the insertion end against the portion of the joint into which it was inserted, generating a pressure against the insertion end of the device, as described further herein. The one or more force indicators may be configured to record the amount of pressure applied to the insertion end of the device. In an embodiment, the one or more force indicators may be configured to electronically record an amount of force applied 1015A to the portion of the body and transmit the recording of the amount of force to a computer, including a robotic surgical system or a surgical system.

In an alternative embodiment, the device to be inserted may further include a tissue retractor with a first prong with an insertion end and a base end and a second prong with an insertion end and a base end, at least two handles, and one or more force indicators arranged around a rotational joint. A rotational spring is wrapped round the rotational joint. Applying the force 1010A to the handles of the device may generate a torque that applies a force against the portion of the joint into which the insertion end of the tissue retractor is inserted. When the handle reaches a displacement point at which a predetermined torque is achieved, the one or more force indicators may be configured to electronically record an amount of force applied to the portion of the body and transmit the recording of the amount of force to a computer, including a robotic surgical system or a surgical system.

In a further embodiment, the device may further include one or more location tracking devices configured to record one or more location, orientation, and motion data points as the device is moved that may be indicative of the motion the device or one or more components thereof, such as the devices described further herein. The one or more location, orientation, and motion data points may be received by a computer, including a robotic surgical system or a surgical system, and used to account for the motion of the device when the force was applied 1010A in order to facilitate more accurate measurement of the applied force.

In a further embodiment, a patient tracking system may be attached to the portion of the joint before the application of force 1010A. The patient tracking system may include one or more location trackers configured to record one or more location, orientation, and motion data points as the device is moved that may be indicative of the portion of the joint, such as the devices described further herein. The one or more location, orientation, and motion data points may be received by a computer, including a robotic surgical system or a surgical system, and used to account for the motion of the portion of the joint when the force was applied 1010A, in order to facilitate more accurate measurement of the applied force.

Figure 10B:
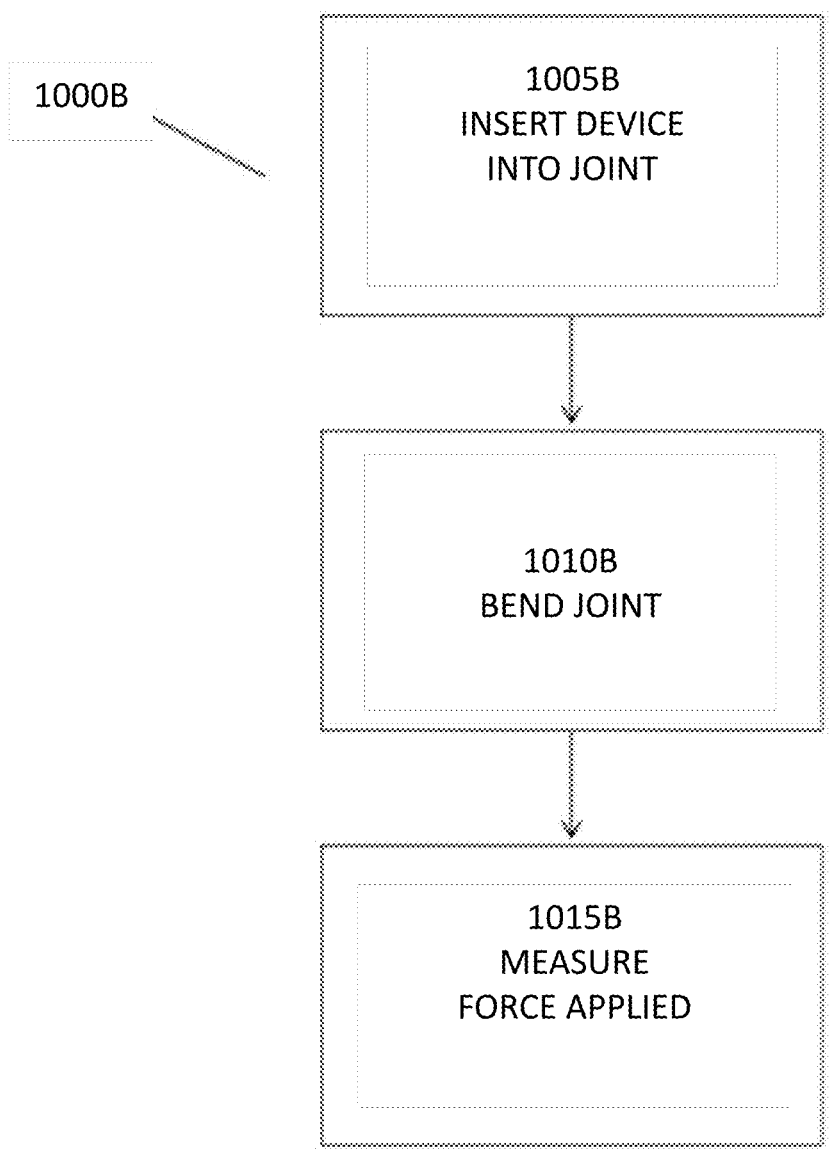
FIG. 10B depicts another illustrative flow diagram for measuring a force applied to a joint during a surgical procedure in accordance with an embodiment.

FIG. 10B depicts a flow diagram 1000B of an illustrative method of measuring an intra-articular force in a joint during a surgical procedure in accordance with an embodiment. As shown in FIG. 10B, a device may be inserted 1005B into a portion of a joint. In some embodiments, the joint may be a knee. However, the device may be inserted in other joints, such as a shoulder, an elbow; an ankle, a hip, or the like, within the scope of this disclosure. The device to be inserted may include a tissue retractor having an insertion end and a base end, a handle, and one or more force indicators, such as the devices described further herein.

In an embodiment, the joint may be bent 1010B while the device is moved so that the location and orientation of the device relative to at least one portion of the joint may be maintained. Bending the joint in this manner while maintaining the location and orientation of the device relative to the joint may cause displacement of the insertion end of the tissue retractor relative to the base end, as described further herein. In an embodiment, the force applied may be measured 1015B by the one or more force indicators that may be configured to electronically record an amount of force resulting from the bending of the joint. In an embodiment, the one or more force indicators may be configured to electronically record an amount of force applied to the portion of the body and transmit the recording of the amount of force to a computer, including a robotic surgical system or a surgical system.

In an alternative embodiment, the joint may be bent 1010B causing the articular surfaces of the joint to apply a pressure against the insertion end of the device. The one or more force indicators may be configured to record the amount of pressure applied to the insertion end of the device, as described further herein. In an embodiment, the one or more force indicators may be configured to electronically record an amount of force applied 1015B to the portion of the body and transmit the recording of the amount of force to a computer, including a robotic surgical system or a surgical system.

In an alternative embodiment, the device to be inserted may further include a tissue retractor with a first prong with an insertion end and a base end and a second prong with an insertion end and a base end, at least two handles, and one or more force indicators arranged around a rotational joint. A rotational spring is wrapped round the rotational joint. Bending the joint 1010B may cause the articular surfaces of the joint to apply a pressure against the insertion ends of the first prong and the second prong of the device, causing displacement of the handles relative to each other. When the handle reaches a displacement point at which a predetermined torque is achieved, the one or more force indicators may be configured to electronically record an amount of force applied to the portion of the body and transmit the recording of the amount of force to a computer, including a robotic surgical system or a surgical system.

In a further embodiment, the device may further include one or more location tracking devices configured to record one or more location, orientation, and motion data points as the device is moved that may be indicative of the motion the device or one or more components thereof, such as the devices described further herein. The one or more location, orientation, and motion data points may be received by a computer, including a robotic surgical system or a surgical system, and used to account for the motion of the device when the force was applied 1010B in order to facilitate more accurate measurement of the applied force.

In a further embodiment, a patient tracking system may be attached to the portion of the joint before the application of force 1010B. The patient tracking system may include one or more location trackers configured to record one or more location, orientation, and motion data points as the device is moved that may be indicative of the portion of the joint, such as the devices described further herein. The one or more location, orientation, and motion data points may be received by a computer, including a robotic surgical system or a surgical system, and used to account for the motion of the portion of the joint when the force was applied 1010B in order to facilitate more accurate measurement of the applied force.

Figure 11:
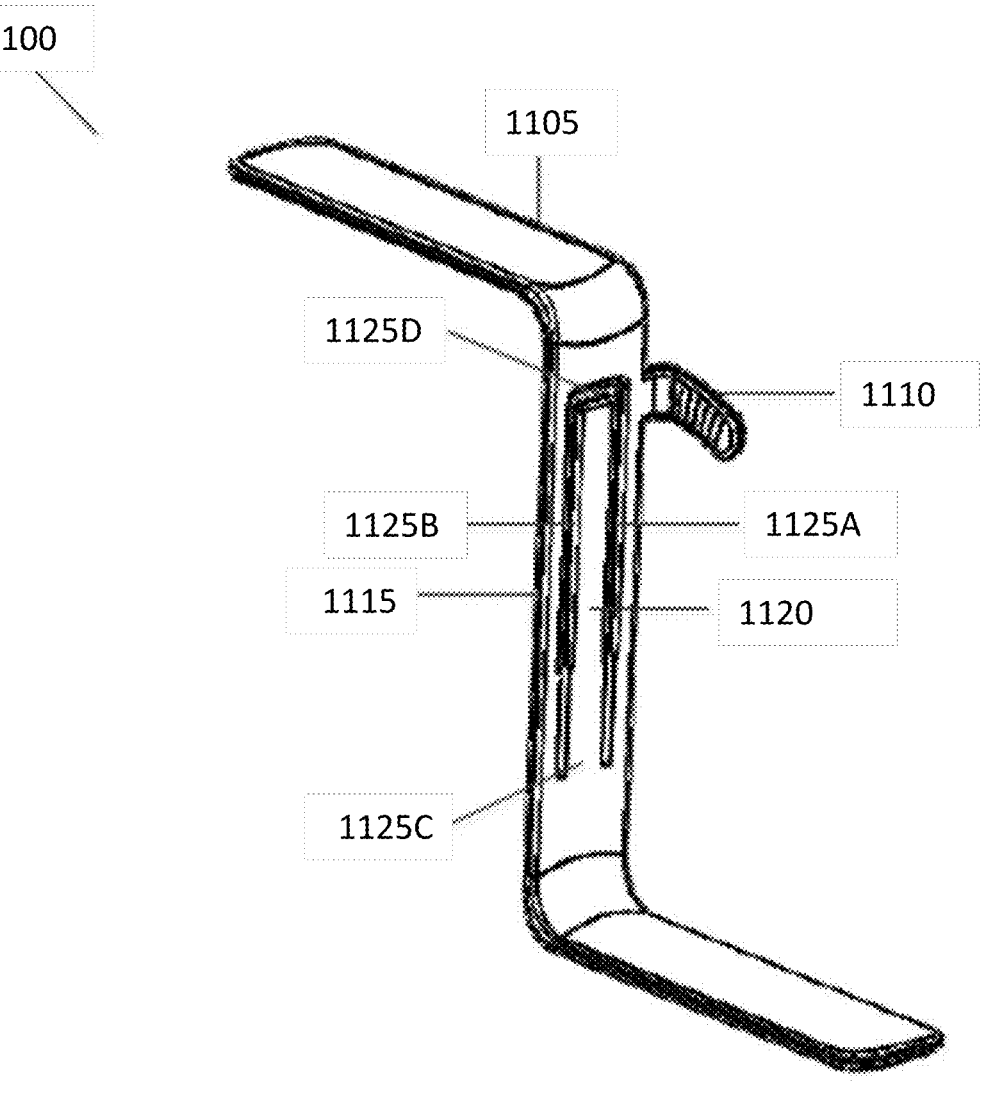
FIG. 11 depicts a perspective view of another device in accordance with an embodiment.

FIG. 11 depicts an illustrative device in accordance with an embodiment. As shown in FIG. 11, the device 1100 may include a tissue retractor 1105 and a force indicator 1110. The tissue retractor 1105 may be substantially z-shaped and may include a body 1115 and a tongue component 1120 contained within the confines of the body. The tongue component 1120 may include a first long side 1125A, a second long side 1125B, a first short side 1125C, and a second short side 1125D. The tongue component 1120 is only connected to the body 1115 along the first short side 1125C. In other words, the first long side 1125A, the second long side 1125B, and the second short side 1125D may not be directly attached to any other portion of the body 1115.

The force indicator 1110 may be connected to the body 1115. In an embodiment, the force indicator 1110 may be connected to the body 1115 at a position in proximity to the second short side 1125D. In an embodiment, the force indicator 1110 may be an analog gauge that includes at least one marker corresponding to at least one force measurement. In such an embodiment, the tongue component 1120 may be configured to act as a needle of the analog gauge when a force is applied to a portion of the body 1115.

Figure 12:
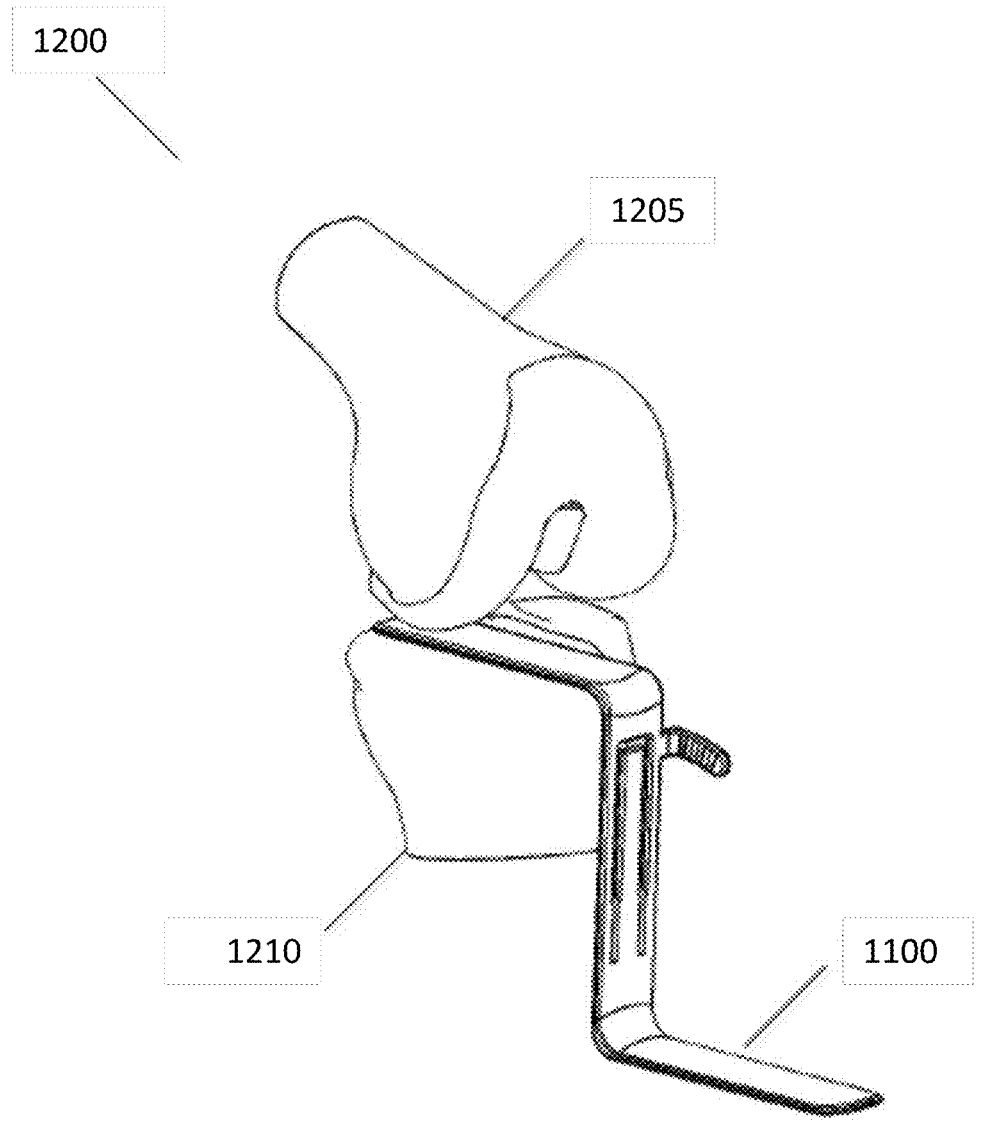
FIG. 12 depicts a perspective view of the device of FIG. 11 inserted into a patient knee in accordance with an embodiment.

FIG. 12 depicts the device of FIG. 11 inserted in a knee joint in accordance with an embodiment. As shown in FIG.

Figure 13:
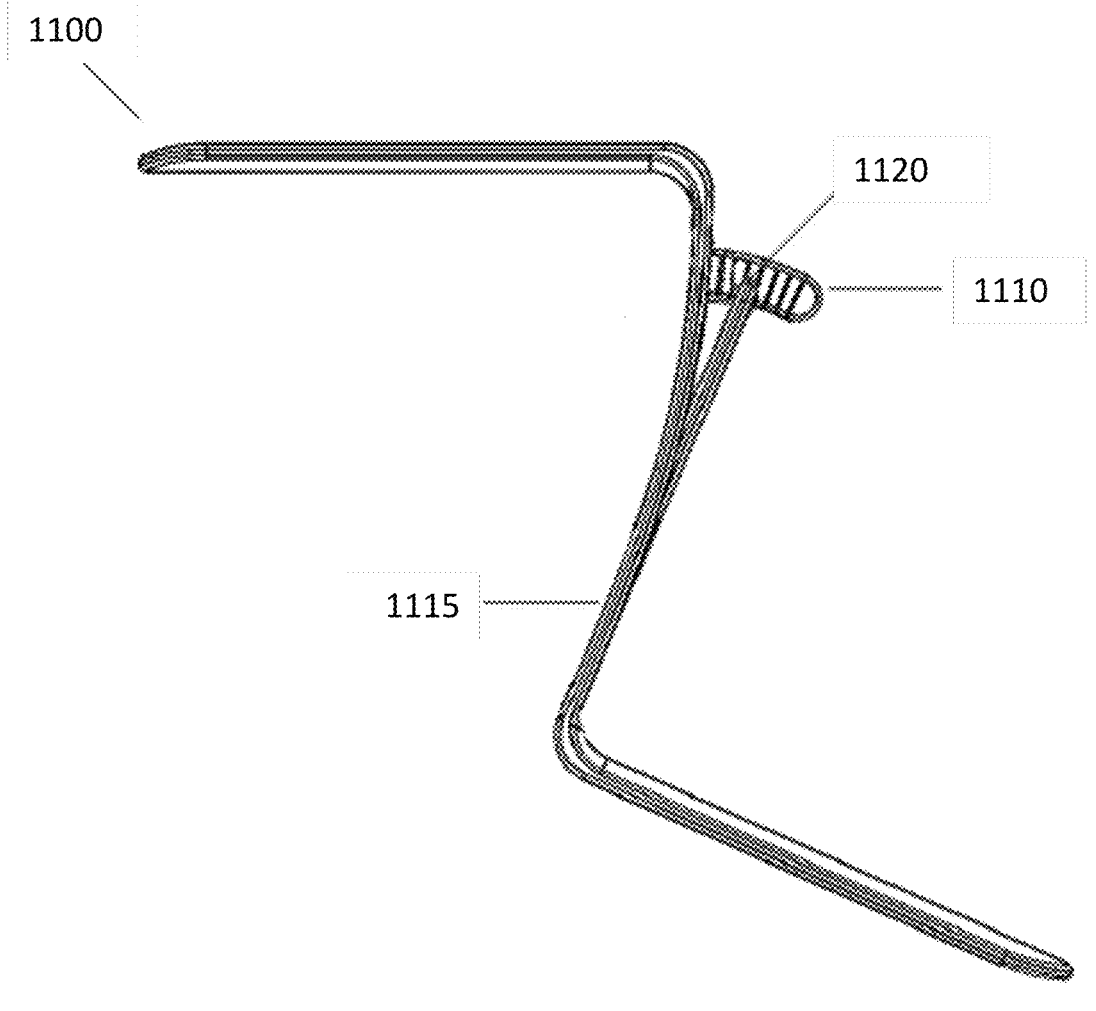
FIG. 13 depicts a side view of the device of FIG. 11 in accordance with an embodiment.

12, the device 1100 may be inserted between the femur 1205 and the tibia 1210 of a patient's knee 1200. In an embodiment, an amount of force may be applied to a portion of the device 1100 distal from the insertion point, which may cause a deflection angle to form between the body 1115 and the tongue component 1120. An example of a device in a deflected state is depicted in FIG. 13 and discussed in further detail below.

Referring back to FIG. 11, the tongue component 1120 may be configured to be parallel to the portion of the body 1115 surrounding the tongue component when no force is applied to the body. In an embodiment, the tongue component 1120 may be configured to be displaced from the portion of the body 1115 surrounding the tongue component when an amount of force is applied to at least a portion of the body. In an embodiment, an angle of displacement between the body 1115 and the tongue component 1120 may be proportional to the force applied to the portion of the body. For example, the angle of displacement between the body 1115 and the tongue component 1120 may be directly or linearly proportional to the applied force. Alternately, the angle of displacement between the body 1115 and the tongue component 1120 may be logarithmically proportional to the applied force. Other relationships between the displacement angle and the applied force may also occur depending upon the precise nature and construction of the tongue component 1120 and the body 1115 as will be apparent to those of ordinary skill in the relevant art.

Figure 14:
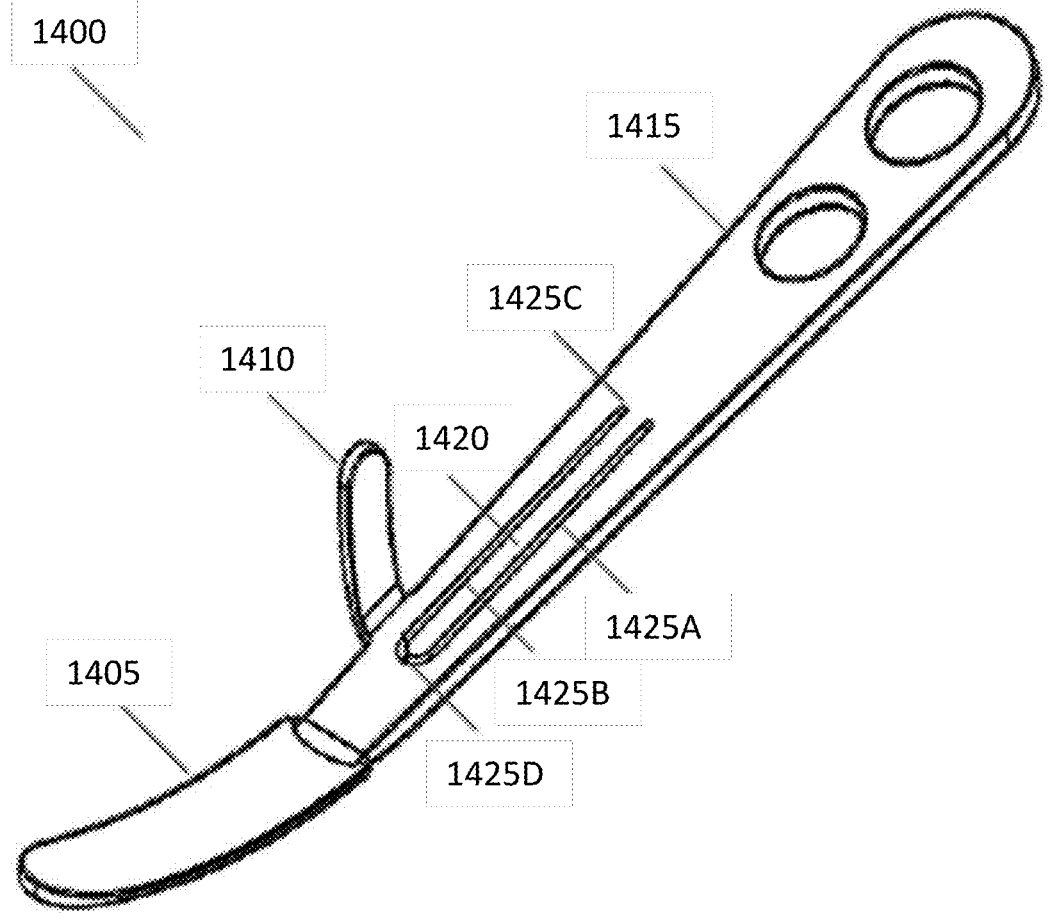
FIG. 14 depicts a perspective view of another device in accordance with an embodiment.

FIG. 14 depicts an illustrative device in accordance with an alternate embodiment. As shown in FIG. 14, the device 1400 may include a tissue retractor 1405 and a force indicator 1410. The tissue retractor 1405 may be a Hohmann-type retractor and may include a body 1415 and a tongue component 1420 contained within the confines of the body. The tongue component 1420 may include a first long side 1425A, a second long side 1425B, a first short side 1425C, and a second short side 1425D. The tongue component 1420 is only connected to the body 1415 along the first short side 1425C. In other words, the first long side 1425A, the second long side 1425B, and the second short side 1425D may not be directly attached to any other portion of the body 1415.

The force indicator 1410 may be connected to the body 1415. In an embodiment, the force indicator 1410 may be connected to the body 1415 at a position in proximity to the second short side 1425D. In an embodiment, the force indicator 1410 may be an analog gauge that includes at least one marker corresponding to at least one force measurement. In such an embodiment, the tongue component 1420 may be configured to act as a needle of the analog gauge when a force is applied to a portion of the body 1415.

In an embodiment, the tongue component 1420 may be configured to be parallel to the body 1415 when no force is applied to the body. In an embodiment, the tongue component 1420 may be configured to be displaced from the body 1415 when an amount of force is applied to at least a portion of the body. In an embodiment, an angle of displacement between the body 1415 and the tongue component 1420 may be proportional to the force applied to the portion of the body. For example, the angle of displacement between the body 1415 and the tongue component 1420 may be directly proportional to the applied force. Alternately, the angle of displacement between the body 1415 and the tongue component 1420 may be logarithmically proportional to the applied force. Other relationships between the displacement angle and the applied force may also occur depending upon the precise nature and construction of the tongue component

1420 and the body 1415 as will be apparent to those of ordinary skill in the relevant art.

Figure 15:
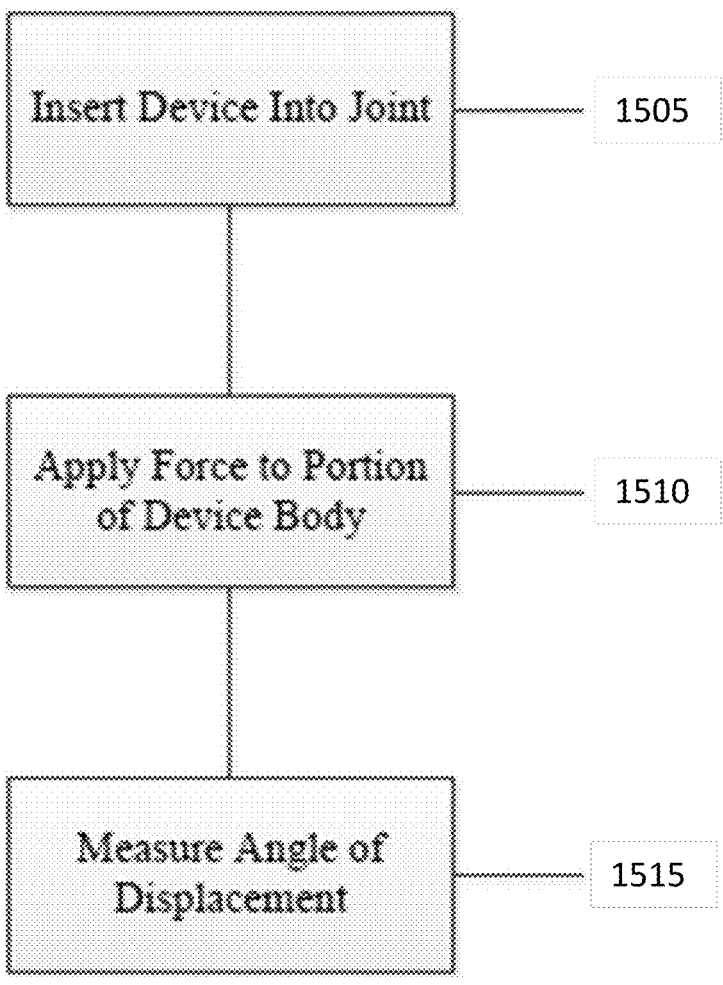
FIG. 15 depicts an illustrative flow diagram for measuring a force applied to a joint during a surgical procedure in accordance with an embodiment.

FIG. 15 depicts a flow diagram of an illustrative method of measuring a force applied to a joint during a surgical procedure in accordance with an embodiment. As shown in FIG. 15, a device may be inserted 1505 into a portion of a joint. In some embodiments, the joint may be a knee. However, the device may be inserted 1505 into other joints, such as a shoulder, an elbow, an ankle, a hip, or the like, within the scope of this disclosure. The device to be inserted may include a tissue retractor having a body and a tongue component and a force indicator that is connected to the body, such as the devices described further herein.

A force may be applied 1510 onto a portion of the body. In an embodiment, the force may be applied 1510 to the portion of the body of the device that is distal from the joint. Applying the force in this manner may cause the tongue component to be displaced from the portion of the body surrounding the tongue component by an angle. This displacement angle may be used to measure 1515 the amount of force applied to the body using the force indicator. For example, the angle by which the tongue component is displaced from the body may indicate an amount of force in comparison with the force indicator. Alternately, the force indicator may be configured to record an amount of force applied to the portion of the body electronically. In an embodiment, the force indicator may be configured to electronically record an amount of force applied to the portion of the body and transmit the recording of the amount of force to a robotic surgical system.

The methods and systems disclosed herein are described with reference to the LifeModeler KneeSIM Lab offered by LIFEMODELER, INC. of San Clemente, CA, which is a subsidiary of SMITH & NEPHEW, INC. of Memphis, TN. However, persons of ordinary skill in the art will recognize that the methods described herein may be carried out using a variety of additional and/or alternate multi-body muscu-loskeletal analysis applications including OpenSim, Any Body (Any Body Technology Inc. of Salem, MA) or Adams (MSC Software Corp. of Newport Beach, CA).

Figure 16A:
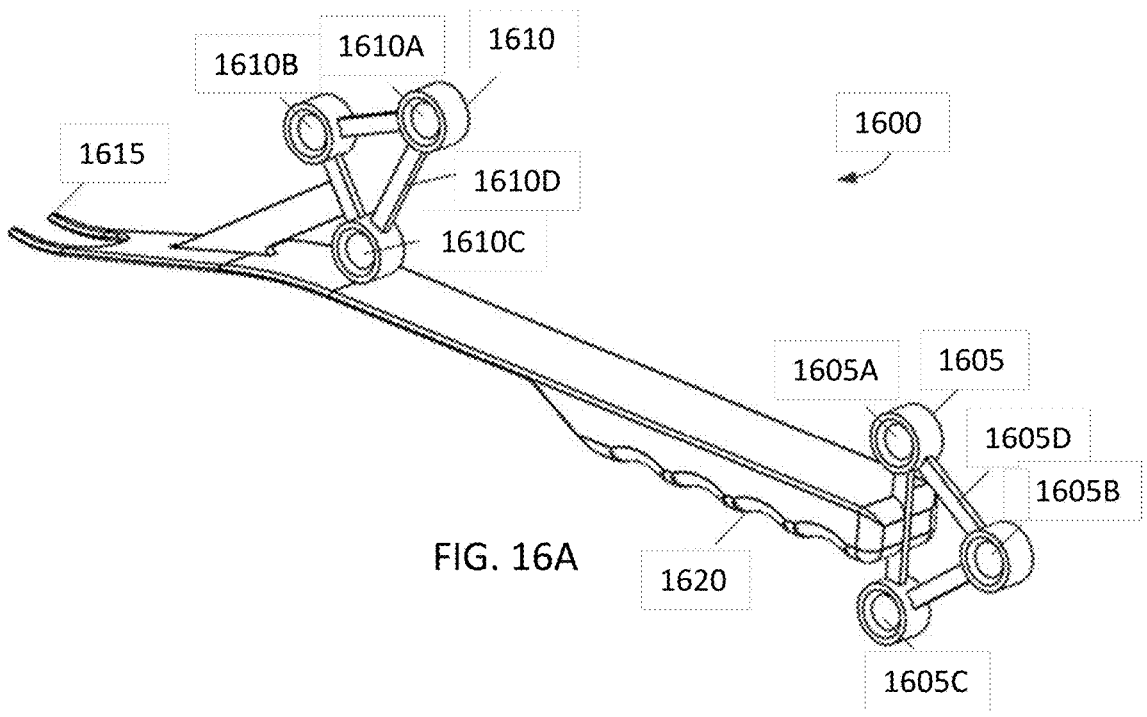
FIG. 16A depicts an illustrative perspective view of a tool used to apply a force to a joint during a surgical procedure in accordance with an embodiment.
Figure 16B:
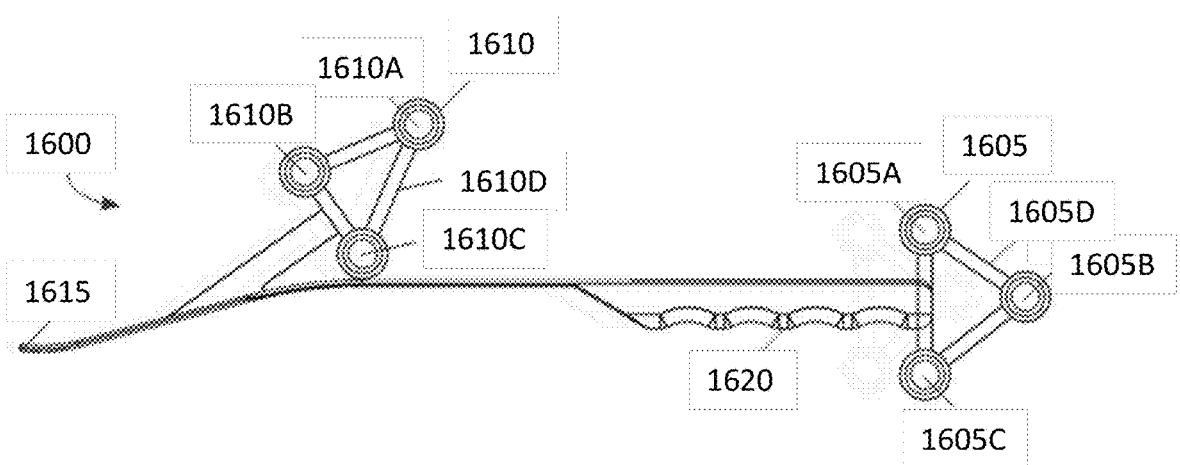
FIG. 16B depicts an illustrative side view of a tool used to apply a force to a joint during a surgical procedure in accordance with an embodiment.

FIGS. 16A and 16B depict a perspective view and a side view, respectively, of an illustrative tool used to apply a force to a joint during a surgical procedure in accordance with an embodiment. As shown in FIGS. 16A and 16B, the tool, such as a retractor 1600, may include a plurality of fixed tracking arrays, such as a first tracking array 1605 and a second tracking array 1610, and an insertion end 1615. In some embodiments, each tracking array 1605, 1610 may be an active tracking array. In some embodiments, each tracking array 1605, 1610 may be a passive tracking array. For the purposes of this disclosure, the first and second tracking arrays 1605, 1610 may be optical in nature, although this is non-limiting. In some embodiments, each tracking array 1605, 1610 may include one or more of an optical tracker, an electromagnetic tracker, an infrared tracker, a stereo camera tracker, an active LED tracker, a retroreflective marker tracker, a video tracker, or the like.

The first optical tracking array 1605 may be located at a proximal end of the retractor 1600, and the second optical tracking array 1610 may be located distally from the first optical tracking array towards the insertion end 1615. Each optical tracking array 1605 and 1610 may include a plurality of elements, such as 1605A-C and 1610A-C, and a frame 1605D and 1610D affixing such elements in relation to each other. In an optical tracking system, the elements 1605A-C and 1610A-C may be reflective at a wavelength or plurality of wavelengths detectable by a position tracker (such as 115 in FIG. 1).

In some embodiments, the retractor 1600 may further include a handle 1620. In some embodiments, the portion of the retractor 1600 including the handle 1620 may be substantially thicker than the remainder of the retractor. As such, the portion of the retractor 1600 including the handle 1620 may be more resistant to flexure when a force is applied than the portion of the retractor distal from the handle.

In some embodiments, using a plurality of reflective elements 1605A-C, 1610A-C for each tracking array 1605, 1610 may enable more complete information regarding the position of the tracking arrays with respect to each other. For example, the reflective elements 1605A-C and 1610A-C of the tracking arrays 1605, 1610 may be positioned in a first orientation with respect to each other prior to a force being applied to the retractor 1600. When a force is applied, the orientation of the reflective elements 1605A-C, 1610A-C may differ from the original orientation because the second tracking array 1610 may be deflected from its original position as a result of flexure of the distal portion of the retractor 1600. The position tracker 115 may be able to measure a change in the respective orientations of the tracking arrays 1605 and 1610, which may correspond to an amount of deflection in the retractor 1600. Knowing the geometry and material properties of the tool, the tool deflection may be used to directly calculate the applied force via a beam bending formula that is known to those of ordinary skill in the art. An illustrative force equation for cantilevered beams is provided herein for the tool shown in FIGS. 16A and 16B. However, those of ordinary skill in the art will be aware that different formulas may apply for other tools depending upon the construction, geometry and material properties of the particular tool.

Figure 16C:
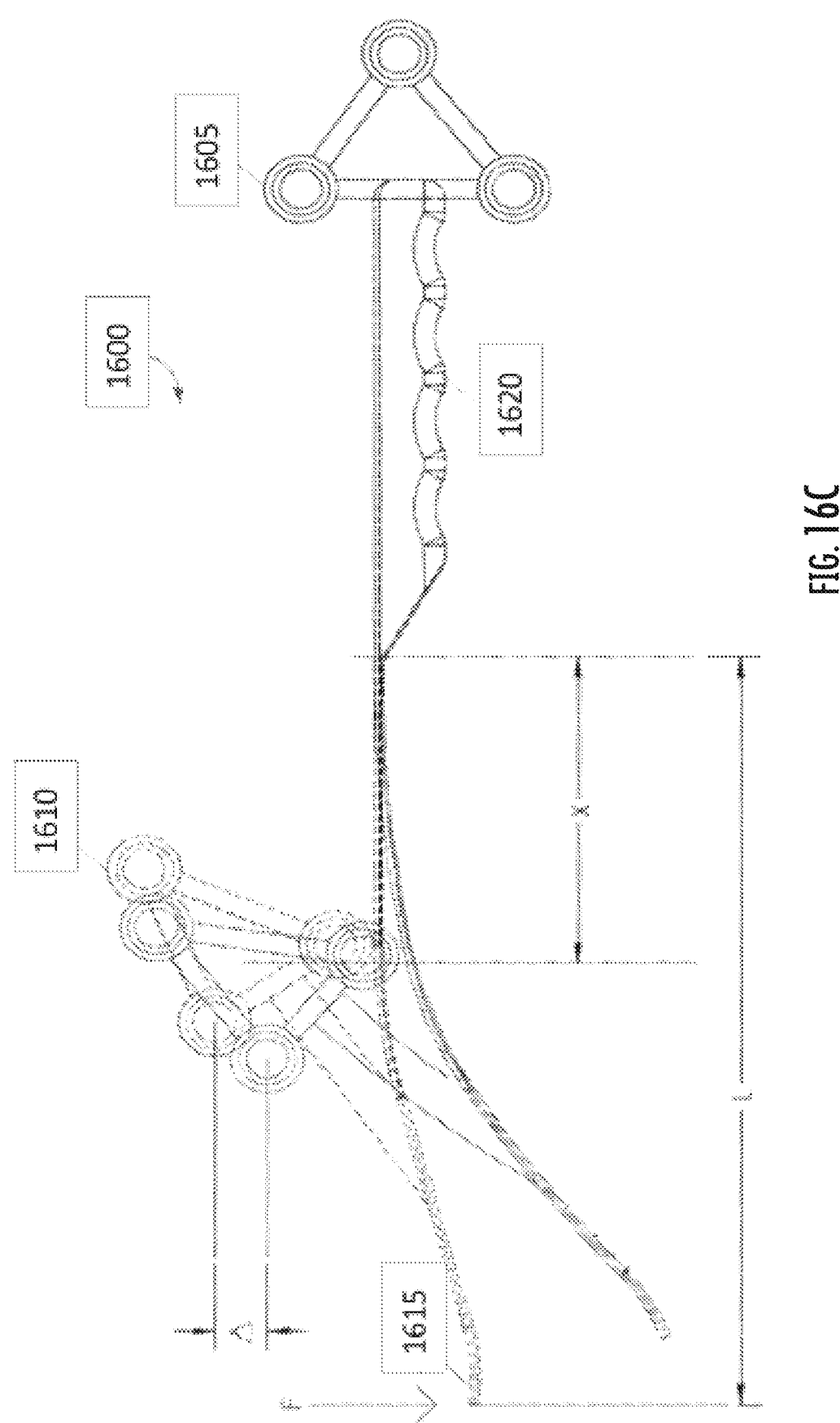
FIG. 16C depicts another illustrative side view of a tool used to apply a force to a joint during a surgical procedure in accordance with an embodiment.

FIG. 16C depicts the illustrative device of FIG. 16A under displacement (solid lines) and prior to applying a force (dashed lines) in accordance with an embodiment. As shown in FIG. 16, the tool 1600 may include a distal portion between the insertion end 1615 and the handle 1620 having length L. The distal portion may be flexible as compared to the rigid handle 1620 of the tool 1600. The distal portion of the tool 1600 may have a modulus of elasticity (referred to as E) determined by the material used for the distal portion. In addition, the distal portion of the tool 1600 may have a moment of inertia (referred to as I) defined by the geometry of the tool. The second tracking array 1610 is placed at a known distance (referred to as x) away from the handle 1620, and a force (referred to as F) is applied at the insertion end 1615 of the tool 1600. Because the tool 1600 is constructed as a cantilevered beam, the tool deflection (referred to as A) can be determined using formula (1):

$$\Delta = \frac{Fx^2}{6EI}(3L - x) \tag{1}$$

Formula (1) may be rewritten to solve for the magnitude of the force F based on the other identified characteristics of the tool as follows:

$$F = \frac{\Delta 6EI}{x^2(3L - x)} \tag{2}$$

Figure 16D:
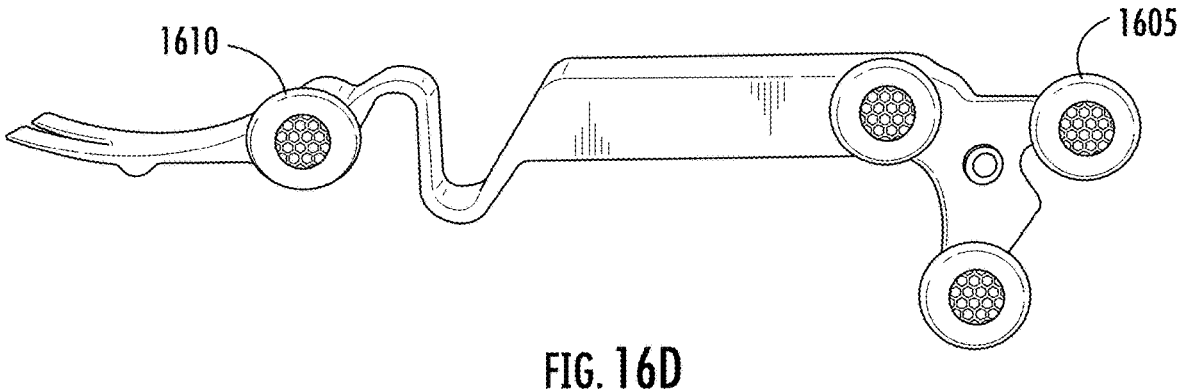
FIG. 16D depicts a illustrative side view of another tool used to apply a force to a joint during a surgical procedure in accordance with an embodiment.
Figure 16E:
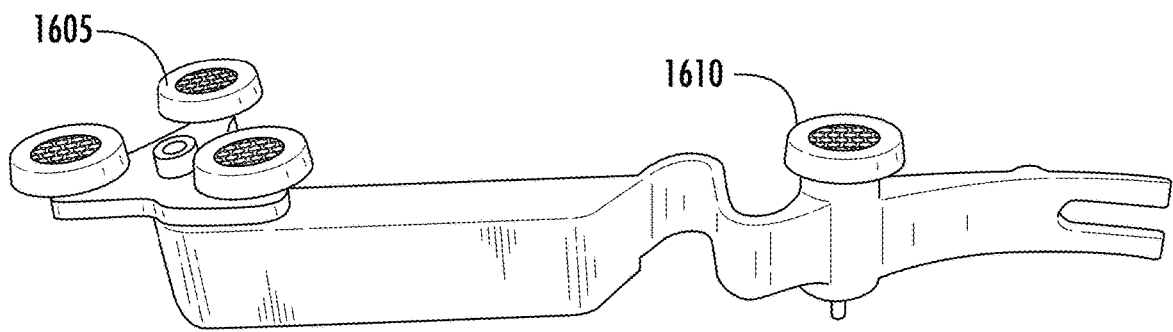
FIG. 16E depicts an illustrative perspective view of a tool used to apply a force to a joint during a surgical procedure in accordance with an embodiment.

Various additional embodiments of the tool 1600 are shown in FIGS. 16D and 16E. As shown, and described herein, the tool 1600, may have various tracking arrays 1605 and 1610, which may be a passive tracking array. For the purposes of this disclosure, the first and second tracking arrays 1605, 1610 may be optical in nature, although this is non-limiting. In some embodiments, each tracking array 1605, 1610 may include one or more of an optical tracker, an electromagnetic tracker, an infrared tracker, a stereo camera tracker, an active LED tracker, a retroreflective marker tracker, a video tracker, or the like.

Figure 17:
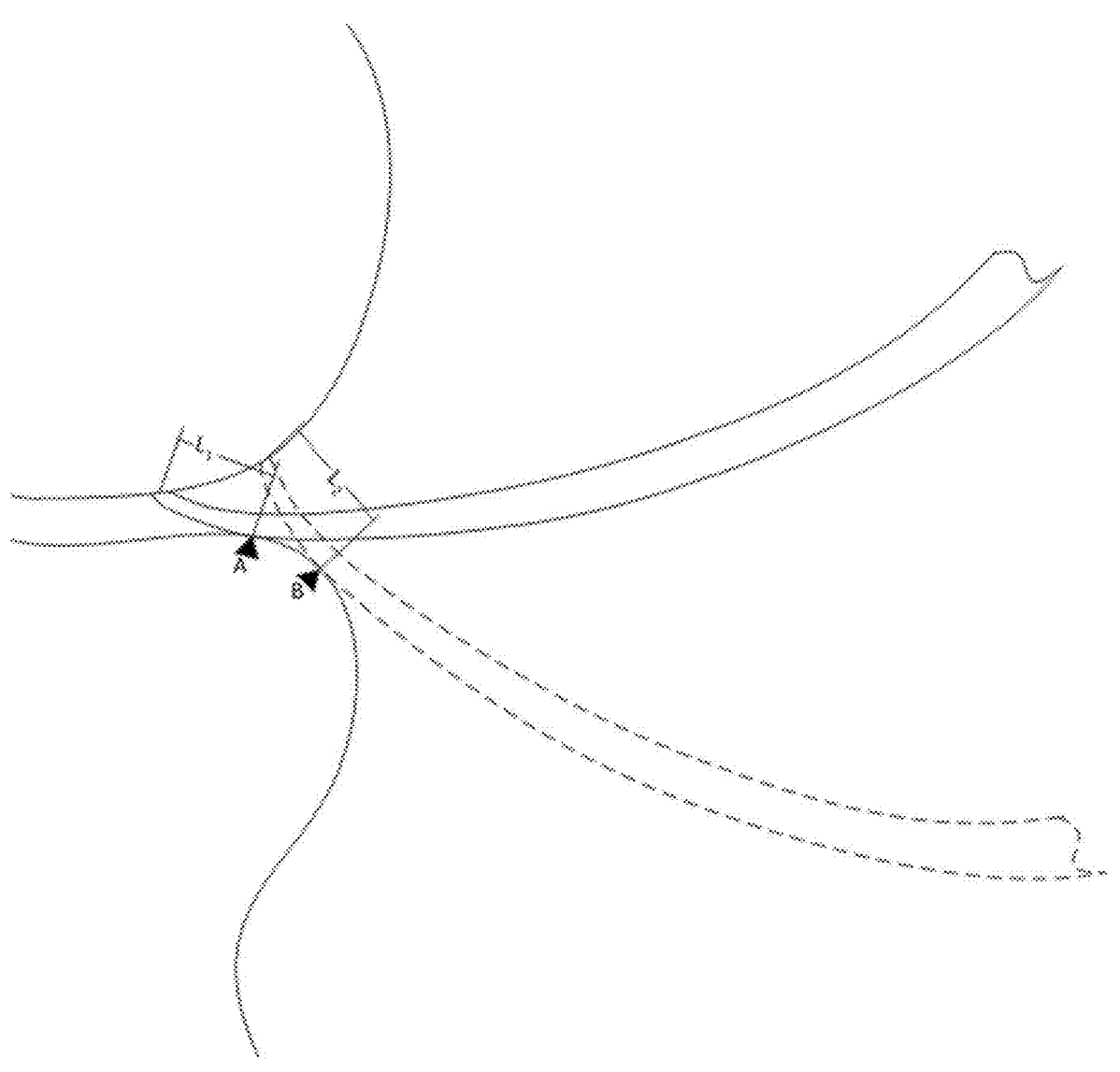
FIG. 17 depicts an illustrative view of a distal end of a device prior to applying a force (solid lines) and under displacement (dashed lines) in accordance with an embodiment

FIG. 16C depicts a distal end of an illustrative device prior to applying a force (solid lines) and under displacement (dashed lines) in accordance with an embodiment. In some embodiments, such as is shown in FIG. 17, the fulcrum point of the tool may be at a point proximal from the distal end of the tool. For example, if a tool is inserted between the tibia and the femur, the position of the fulcrum point may depend in part upon the shape and position of the tibia and/or the femur.

In some embodiments, the determination of the force vector may further depend on the geometry of the bony anatomy, the distal tip of the tool, and/or other anatomical information or locations on the tool. For example, an acting point distal from the fulcrum point may also be used to determine the force vector. The acting point may be a location at which the tool contacts one of the bones of the patient when inserted into the joint. In some embodiments, as is shown in FIG. 17, the acting point may be the distal tip of the tool. In some embodiments, the acting point may be a location proximal from the distal tip but distal from the fulcrum point.

In some embodiments, the shape and position of the tibia and femur (or other bones in a patient's anatomy) may be determined pre-operatively using images and/or determined and updated intraoperatively, such as with a mapping tool equipped with a tracking array. Such information may be used to assist in determining the locations of the fulcrum point of the tool, the acting point of the tool, or other points on the tool. Such locations may be used to determine the magnitude and direction of the applied force based on the deflection of the tool.

In some embodiments, if locations of ligament insertion points are known, such as by estimation from a statistical model or by direct palpation or measurement, a kinematic model including ligament information may be constructed. Ligament forces may be deduced using such a model. Kinematic models which may be used to assist in determining such forces may be known to those of ordinary skill in the art. Such models may receive anatomical geometries and values for the stiffness of various elements of the patient's anatomy.

Figure 18:
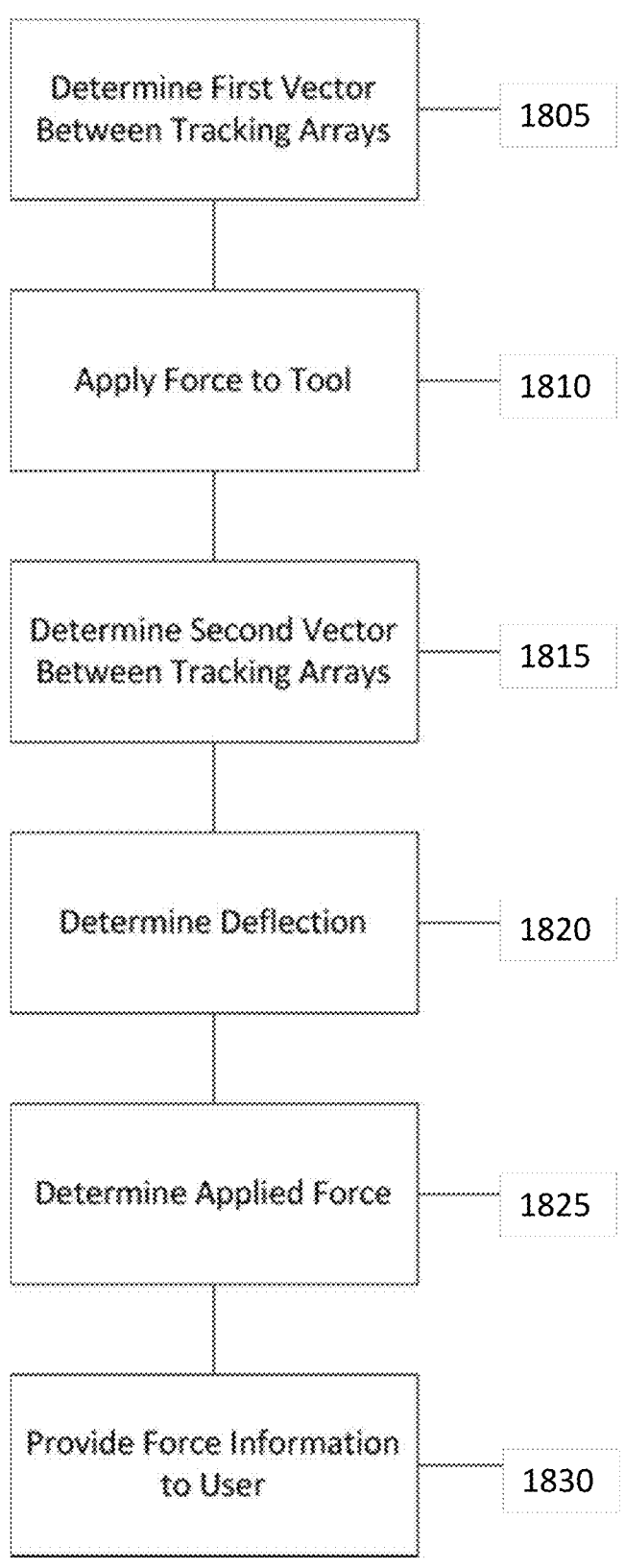
FIG. 18 depicts an illustrative flow diagram for determining an applied force using an optical tracking system in accordance with an embodiment

FIG. 18 depicts a flow diagram of an illustrative method of determining an applied force using an optical tracking system in accordance with an embodiment. As shown in FIG. 18, an optical tracking system may determine 1805 a first vector between a first tracking array on a tool, such as a retractor, and a second tracking array on the tool. The first vector may include a first distance and a first direction. In an embodiment, the first direction may be determined with respect to a frame of reference. For example, when performing a TKA surgical procedure, the frame of reference may be defined by a portion of the patient's anatomy, such as the tibia or the femur on which the TKA surgical procedure is being performed. Other frames of reference may be used depending upon the application for which the force is being applied. Identification or determination of the frame of reference may be performed using one or more additional tracking arrays as will be apparent to those of ordinary skill in the art. In an embodiment, the first vector may be determined 1805 in an initial condition, such as when the tool does not have a force applied to it. In some embodiments, the optical tracking system may determine 1805 the first vector in response to receiving an input from a user. For example, a user may press a button designating that the first vector is to be recorded at a particular time.

A force may be applied 1810 to the tool. In some embodiments, the force may be applied 1810 to the tool after the tool has been inserted into a knee during a TKA surgical procedure in order to perform a joint laxity test. In some embodiments, the force may be applied 1810 by a surgeon pushing or pulling on the tool. In some embodiments, the tool used to apply 1810 the force and the manner in which the force is applied may be determined based on the application for which the force is being applied.

The optical tracking system may determine 1815 a second vector between the first tracking array and the second tracking array. The second vector may include a second distance and a second direction. In an embodiment, the second direction may be determined with respect to the frame of reference. In an embodiment, the second vector may be determined 1815 in a stressed condition, such as when the force has been applied. In an embodiment, the optical tracking system may determine 1815 the second vector between the first and second tracking arrays as the force is being applied. In some embodiments, the optical tracking system may determine 1815 a plurality of vectors between the first and second tracking arrays in real or near real time prior to and/or as the force is being applied and may record information pertaining to the plurality of vectors over time. In some embodiments, the optical tracking system may determine 1815 the second vector in response to receiving an input from a user similar to the manner described above in reference to determining 1805 the first vector.

An amount of deflection in the tool may be determined 1820. The amount of deflection may be determined 1820 with respect to the frame of reference discussed above. In an embodiment, the amount of deflection may be determined 1820 based on an initial position of the second tracking array and a position of the second tracking array when the force is applied. Alternate and/or additional tool deflection values may be determined within the scope of this disclosure.

The applied force may be determined 1825 based on at least the amount of deflection, the modulus of elasticity for the tool, and the moment of inertia for the tool. In some embodiments, the magnitude of the force may be determined 1825. In some embodiments, the magnitude of the force and the direction in which the force is applied (i.e., a vector representing the applied force) may be determined 1825.

In some embodiments, a processor that is part of or operably connected with the optical tracking system may be used to identify the location of each tracking array. The processor may determine 1825 one or more vectors for the applied force based on, for example, formula (2) or a corresponding formula based on the geometry of the tool used to apply the force. In some embodiments, the applied force may be separated into a plurality of vectors. For example, when performing a joint laxity measurement in a TKA procedure, the magnitude of the force in a direction that is in line with the tibia and the magnitude of the force in a direction that is perpendicular to the tibia may each be provided to a surgeon. The magnitude of the inline force may allow a surgeon to know whether a proper amount of force is being applied to the knee to determine the joint laxity. In contrast, the magnitude of the force in the perpendicular direction may identify, for example, wasted effort on behalf of the surgeon. In some embodiments, three vectors may be computed to determine the applied force in orthogonal directions.

In some embodiments, a user may provide information regarding the modulus of elasticity and the moment of inertia for the tool in order to determine 1825 the magnitude of the applied force. In some embodiments, characteristics of the tool, including the modulus of elasticity and the moment of inertia, may be known in advance of the application of force. In such embodiments, the applied force may be determined 1825 by accessing a lookup table because all other variables in the force determining equation may be known (e.g., L, x, E, and I in equation (2) may each have a constant value for a given tool). For example, the force-displacement relationship may be characterized through a calibration procedure by which a plurality of applied force magnitudes and the corresponding deformations of the tool are tracked and recorded. In some embodiments, the force-displacement relationship may be used to generate a best-fit equation. In some embodiments, the force-displacement values may be recorded as entries in a look-up table. During a procedure, the deformation of the tool may be measured and compared to values in the look-up table in order to determine 1825 the magnitude of the force. In some embodiments, interpolation may be used to determine a magnitude of an applied force for which the deformation is between two recorded values. Other methods of determining 1825 the magnitude of the applied force may also be performed as will be apparent to those of ordinary skill in the art.

In some embodiments, one or more of the variables in the force determining equation may be marked or encoded on the tool. In an embodiment, an alphanumeric designator may be used to denote one or more of the variable values. In an embodiment, a barcode designator may be used to denote one or more of the variable values. In an embodiment, a QR code designator or other multi-dimensional barcode designator may be used to denote one or more of the variable values. In some embodiments, a designator may be used to access a table that associates values for one or more of the variables with the tool.

In some embodiments, a calibration device may be used to determine one or more of the values for the variables in the force determining equation. For example, the tool may be inserted into the calibration device and a known force may be exerted against the tool. One or more measurements may be taken prior to and as the force is being applied to the tool in order to determine one or more of the values for the variables in the force determining equation. Additional and/or alternate methods and systems may be used to determine the values for the variables as will be apparent to those of ordinary skill in the art.

In some embodiments, a particular tool having particular characteristics may be selected based on the amount of force that is intended to be applied. For example, a first tool that is more flexible may be selected if a magnitude of the applied force is intended to be in a first range that is relatively low, and a second tool that is more rigid may be selected if a magnitude of the applied force is intended to be in a second range that is relatively high. In some embodiments, a processing system may direct a user to select a particular tool based on the intended applied force.

The information pertaining to the magnitude and direction of the applied force may be provided 1830 to a user. In some embodiments, numerical values for the magnitude and/or direction may be displayed 1830 to the user. In some embodiments, the displayed numerical values may be updated substantially in real time based on the force that is being applied to the tool at that time.

In some embodiments, the magnitude and direction of the applied force may be displayed 1830 on a display associated with or in operable communication with the tracking system. In some embodiments, the magnitude and direction of the applied force may be displayed 1830 on an augmented reality headset worn by a user.

In some embodiments, a maximum magnitude of the applied force may be provided 1830 to the user. In some embodiments, a minimum magnitude of the applied force may be provided 1830 to the user. In some embodiments, an average magnitude of the applied force over time may be provided 1830 to the user.

In some embodiments, visual feedback information pertaining to the magnitude and/or direction of the applied force may be provided 1830 to the user. For example, if the user is wearing an augmented reality headset, feedback information pertaining to the magnitude may include a visual indication overlaid over the tool, proximate to the tool, or the like. In some embodiments, the visual indication may include a first color, such as green, if more force should be applied, and a second color, such as red, if less force should be applied.

In some embodiments, feedback information for the direction may include an arrow or other visual indication identifying that the user should alter the direction in which the force is applied. In some embodiments, a visual indication identifying a location at which the tool should be positioned in order to apply an appropriate magnitude and direction of force for a given application may be provided 1830 to a user. Alternate or additional information may be provided 1830 to the user within the scope of this disclosure as will be apparent to those of ordinary skill in the art.

The optically tracked device described in reference to FIGS. 16A-16E is merely illustrative of the types of devices that can be used to apply a quantified force to a joint space intraoperatively. Other devices may additionally or alternately be used within the scope of this disclosure to apply a quantified force to a joint. For example, a conventional joint tensioning device, such as a Triathlon R gap sizer-balancer from Stryker Corporation or the Zimmer FuZion®; tensor from Zimmer, Inc., could be used. Alternatively, a load sensing device, such as the Verasense sensor by OrthoSensor, Inc. or the OMNIBotics R device from Corin Group, may be used instead.

One disadvantage of using any of these conventional devices is that each device requires at least a tibial cut and possibly both a tibial cut and a distal femur cut to be performed in advance of use. Options for determining a surgical plan after such cuts are made are more limited because fewer types of adjustments can be performed. The use of such devices may limit adjustments to the surgical plan to, for example, femoral orientation poly sizing and/or ligament release as compared to a much broader range of options available when the joint tensioning device described above in reference to FIGS. 16A-16E is used.

In various computer assisted surgical or robotically assisted surgical systems, the application of a known force can be used for the purpose of ligament balancing. Ligament balancing affects many postoperative criteria for a successful joint replacement, such as a total knee replacement. Proper ligament balancing results in a "balanced knee," which includes most or all of the following characteristics: a full range of movement, symmetrical medial-lateral balance at full extension and 90 degrees of flexion, correct varus/valgus alignment in both flexion and extension, balanced flexion-extension gap without medial-lateral tightness or laxity, a well-tracking patella throughout the range of movement, and correct rotational balance between the tibial and femoral components. In general, a balanced knee contributes to improved alignment and stability for the patient, reduces wear and loosening of the joint, and is likely to increase the range of motion for the patient while reducing pain. In contrast, complications associated with improper ligament balancing include instability of the joint, the possibility of neurovascular damage, and joint pain.

Figure 19:
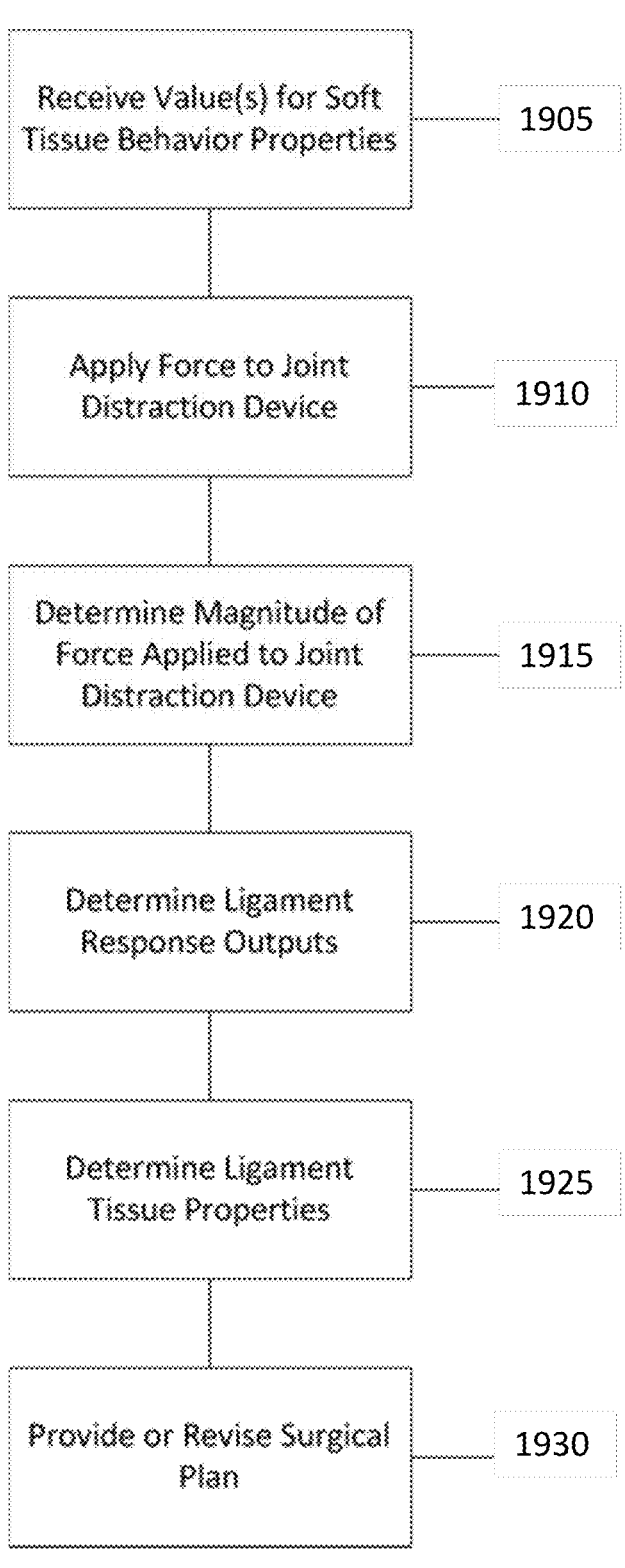
FIG. 19 depicts an illustrative flow diagram for preparing a surgical plan for a joint replacement procedure in accordance with an embodiment.

FIG. 19 depicts a flow diagram of an illustrative method of preparing a surgical plan for a joint replacement procedure in accordance with an embodiment. A CASS or robotically assisted surgical system may include one or more simulation modules that emulate soft tissue behavior in and around the joint and are used to inform a surgeon as to a type of implant, a position of the implant, an orientation of the implant and ligament release or tensioning operations that are needed to achieve well-balanced medial and lateral gaps and well-balanced flexion and extension gaps. A quantified force may be used to provide a more complete assessment of soft tissue behaviors of the joint.

As shown in FIG. 19 the CASS or robotically assisted surgical system may receive 1905 one or more values for properties defining the behavior of soft tissue around a joint. In some embodiments, multi-body dynamic simulations may be performed to assist in the determination of the behavior of soft tissue around a joint. Methods for determining ligament properties are described in more detail below in reference to FIG. 20.

For example, the LifeModeler musculoskeletal simulation software referenced above (or other musculoskeletal simulators) may be used to estimate the behavior and properties of knee ligaments. In such embodiments, musculoskeletal simulations may be customized to model the limb of a specific patient. Key modeling elements may include, for example and without limitation, the patient's bones, joints, muscles, tendons, ligaments, and any implants and/or surgical instruments that are used or are intended to be used within the patient's joint to test the soft tissue behavior. In a multi-body simulation, motion of the various modeling elements can be prescribed and the resulting loading environment inside the joint may be observed.

Figure 20:
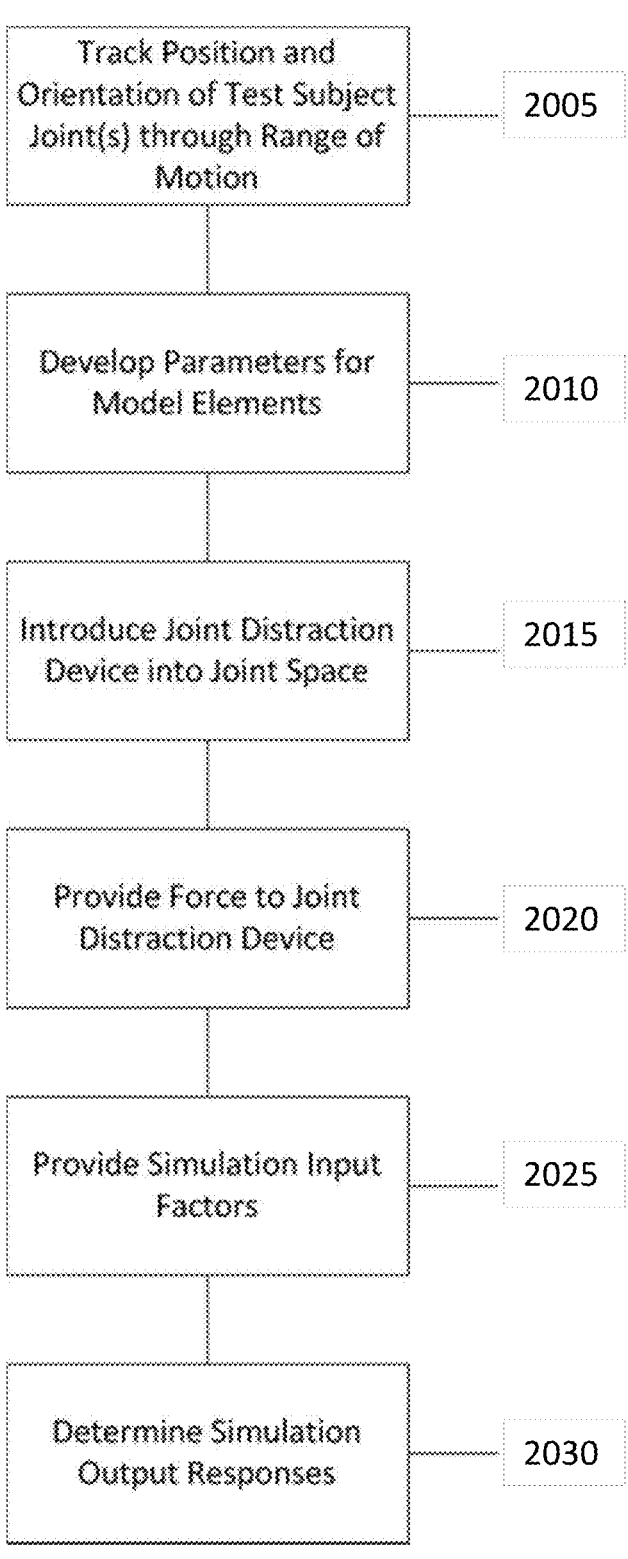
FIG. 20 depicts another illustrative flow diagram for preparing a surgical plan for a joint replacement procedure in accordance with an embodiment.

As shown in FIG. 20, a plurality of joints may be individually tracked 2005 using a surgical navigation system, such as the NAVIO surgical navigation system, when moved through a range of motion in order to precisely determine the position of the various modeling elements. In some embodiments, the plurality of joints may include cadaverous joints in order to reduce the impact of testing on living test subjects. However, range of motion tracking information may be obtained through any means including through experimental tests performed on living subjects.

In some embodiments, the parameters for various model elements for a joint may be developed 2010 using a finite element model. The finite element model may be constructed by, for example, characterizing the movement of the plurality of joints based on the information obtained as the joints are moved through the range of motion. In some embodiments, the characterization may include the position and orientation of various modeling elements surrounding the joint. It is noted that the manner in which the position and orientation of the various modeling elements are tracked in order to prepare a finite element model is not intended to be limited by this disclosure.

Musculoskeletal simulation software may be used to perform a plurality of multi-body simulations based on a model of a joint for a particular patient or a group of patients. The joint model may be based on the properties determined using the finite element model described above. In some embodiments, a virtual joint distraction device may be introduced 2015 into a model representing the joint space. In alternate embodiments, a joint distraction device, such as retractor 1600, may be introduced 2015 into the joint space of one or more test subjects and used 2020 to provide a cantilever load stressing the joint.

In some embodiments, simulation input factors that relate to the implementation of the joint distraction device may be provided 2025 to the musculoskeletal simulator. Such simulation input factors may include, without limitation, a medial-lateral location of the tip of a joint distraction device, an anterior-posterior location of the tip of the joint distraction device, and a magnitude of a force applied to the joint distraction device. In some embodiments, simulation output responses may be recorded 2030. Such simulation output responses may include, without limitation, a joint displacement, one or more joint contact forces, and joint kinematic information.

Values for specific input factors may be determined using design of experiments (DOE) techniques. In addition, such DOE techniques may be used to determine a number of simulations to perform. In various embodiments, at least 100 simulations, at least 1,000 simulations, or at least 10,000 simulations may be performed. DOE techniques may be used to measure the effect of manipulating a plurality of input factor values on desired output responses. In an embodiment, a full factorial or fractional factorial experimental design may be used to characterize the ligament response solution space. In an embodiment, each experimental simulation may include a deep knee bend simulation using a multi-body musculoskeletal analysis application, such as the LifeModeler KneeSIM Lab.

In an embodiment, the above-described input factor values may be updated in each experimental simulation in accordance with the DOE design. For example, a first set of input factor values may be associated with a first simulation, a slightly different set of input factor values may be associated with a second simulation, and so on. In this manner, the set of simulations may determine appropriate values for the output responses under a plurality of conditions. In such embodiments, a virtual joint distraction device may be placed in the joint to apply a varus or a valgus stress, and the knee model may be flexed through a range of motion. As a result of performing a plurality of DOE simulations, information including a plurality of simulation input conditions and the resulting output responses for each simulation may be recorded. A regression analysis may be performed to develop a relationship between the various input factors and a single output response. As a result, the DOE analysis may provide a set of ligament response equations that relate the simulation inputs to the output responses.

The ligament response equations may be used to improve an intraoperative workflow for a navigated or robotically assisted joint replacement surgery, such as a total knee arthroplasty. In some embodiments, a surgeon or other medical professional may preoperatively populate one or more input factor values, such as values relating to patient biometric data (e.g., weight, hip load, and/or limb length). In addition, the musculoskeletal simulation software may receive one or more modeling input factors for the joint. Such modeling input factors may be determined as a result of the finite element modeling described above. In some embodiments, the modeling input factors may include, without limitation, strain-displacement behavior of the ligaments (e.g., stiffness, damping, slack, pre-tension, wrapping behavior, and/or the like), ligament size and location information (e.g., origin and insertion sites, origin and insertion width, number of bundles, and/or the like), and patient anatomy information (e.g., hip load, limb length, cartilage shape, cartilage contact properties, and/or the like).

Referring back to FIG. 19, the surgeon may intraoperatively use a navigated (i.e., tracked) joint distraction device to apply 1910 a varus and/or a valgus stress to the joint. With the joint distraction device in place, the surgeon may move the joint through a full or partial range of motion. As a result, additional input factor information, such as the placement of the joint distraction device and a magnitude of the force applied to the joint distraction device throughout the range of motion may be determined and/or received 1915. In some embodiments, additional input information pertaining to the location and orientation of the bones surrounding the patient's joint may be determined during the range of motion assessment using, for example and without limitation, a surgical navigation system and tracking arrays attached to the bones.

Ligament response equation outputs, including outputs pertaining to joint kinematics and ligament strain, may be determined 1920 based on the received information and the preoperatively assigned input factors. Based on the combination of the known inputs and the output responses, ligament tissue properties for the patient's joint, such as ligament strain and ligament displacement, may also be determined 1925. Based on the above determined information a surgical plan for a joint replacement surgical procedure may be provided or revised 1930. A surgeon may then implement the surgical plan.

In some cases, knowledge of soft tissue properties may be used to achieve proper gap balancing for the knee during the surgical workflow. For example, the NAVIO surgical system may provide gap balancing information to a surgeon based on the characteristics of the patient, the particular implant system being implanted, and the position and orientation of the implant when inserted. In some embodiments, the DOE-derived ligament response equations may be used as an input for the NAVIO surgical system when performing gap balancing.

In some embodiments, statistical uncertainties relating, for example, to a measurement system error and/or a surgical technique error may be included in the ligament response equations. In such embodiments, Monte Carlo simulations may be performed when determining 1920 the ligament response equation outputs to produce a range and probability of likely outcome values. In some embodiments, such analysis may provide a user with a statistical likelihood that the ligament properties have been successfully determined. In alternate embodiments, such analysis may determine whether subsequent ranges of motion analyses are required if a certain likelihood threshold has not been satisfied.

In some embodiments, machine learning operations may be used to replace simulation operations and DOE techniques. In such embodiments, the magnitude of measured joint distraction forces and ligament balancing information may be recorded intraoperatively and used to empirically train a ligament response model. The ligament response model can be continually updated and optimized based on recorded data. Alternatively, the parameters of the ligament response model can be fixed after receiving sufficient training data.

In some embodiments, determined results from the ligament response equations may be used as part of a set of broader knee performance equations. In such embodiments, the set of knee performance equations may suggest implant positions that optimize various biomechanical characteristics including ligament behavior

Example

An arthroplasty procedure is performed by creating an incision in a patient at the surgical site. If necessary, osteophytes are removed from the bones surrounding the joint to create a more consistent surface. A joint distraction device is inserted into a patient's knee. The knee is moved through a range of motion (i.e., flexion) while a constant force is asserted on the joint distraction device. In some cases, the force can be imposed by a robotic arm or similar type of device that is used to assist with the surgical procedure. In other cases, the force is imposed directly by a surgeon. The amount of force is determined by determining the displacement of the joint distraction device using a surgical tracking system. A biomechanical or musculoskeletal simulator is used to identify characteristics of the knee based on the movement of the knee through the range of motion.

Various input factors including patient demographic data and the information from the musculoskeletal simulator are compared with information from previously recorded surgeries to determine a location at which to place a surgical implant, ligament release operations, bony cut planes, or the like. For example, a joint replacement surgery that had a successful outcome for a patient having a similar demographic background and similar joint movement information is identified and used to determine a surgical plan for the current procedure. The identification of the similar procedure is performed using a neural network, DoE techniques, or any other means of comparing the present surgical procedure with past procedures as will be apparent to those of ordinary skill in the art. In other cases, elements of a surgical plan are determined by assembling information from a plurality of similar procedures in order to improve upon the outcomes of past surgeries.

The surgical plan is then followed by performing one or more cuts and/or releasing and/or tensioning one or more ligaments. In some cases, the joint distraction device is reinserted into the joint space after performing one or more of these steps in order to update information regarding the tension in the knee. This additional information can also be compared with previously performed surgical operations in the manner described above. Based upon the measurement after, for example, one of the bone cuts is performed, one or more fine tune adjustments to the surgical plan can be implemented, if necessary, to further strengthen the knee.

One advantage of the above-described example is that the surgical plan is developed in advance of the performance of any bone cuts, which allows for the most flexibility to the surgeon in performing the surgical plan. For example, with systems that determine joint laxity after bone cuts are performed, only ligament tensioning or release or the removal of additional bone may be performed. In the above-described example, however, a determination that less bone should be removed than originally planned may also be performed, thereby preserving surgeon flexibility, which can lead to better patient outcomes.

Additional embodiments may also be considered within the scope of the present disclosure. Such embodiments may be implemented instead of or in concert with one or more of the above-disclosed embodiments. For example, a device developed in accordance with the teachings of the present disclosure may include at least one strain gauge. In an embodiment, the at least one strain gauge may include a sensor. For example, the at least one strain gauge may include one or more of a piezo effect sensor, a Hall effect sensor, and an inductive sensor. Other types of sensors may also be used within the scope of this disclosure.

In an embodiment, the force indicator may include a display. In some embodiments, the display may be in electronic communication with the at least one strain gauge. The display may display, for example, information pertaining to the force applied to the device. In some embodiments, the at least one strain gauge may include a digital strain gauge. In some embodiments, the display may be a digital display. In some embodiments, a digital strain gauge may be configured to record one or more measurements and provide at least one of such measurements to the display. For example, a digital strain gauge may be configured to record one or more of a minimum force measurement and a maximum force measurement. The minimum force measurement may be indicative of a minimum amount of force applied to the device as the joint laxity is being tested. Similarly, the maximum force measurement may be indicative of a maximum amount of force applied to the device as the joint laxity is being tested. Additional and/or alternate measurements may be recorded by a digital strain gauge within the scope of this disclosure. In any of these embodiments, the force indicator may be configured to electronically record an amount of force applied to the portion of the body and transmit the recording of the amount of force to a robotic surgical system or other surgical system.

In an embodiment, a digital strain gauge may include an offset compensation for measurements. The offset compensation may be used to calibrate the device and/or to perform relative measurements based on different amounts of force being applied.

In an embodiment, the device may collect strain data in response to user activation. For example, a user may press a button attached to the device or activate a similar type of trigger to identify a time at which to record the amount of force being applied to the device. In an alternate embodiment, a software module may indicate one or more times to record strain data or the amount of force applied to the body.

In a further embodiment, the at least one strain gauge may be in wireless electronic communication with a robotic surgical system. For example, the at least one strain gauge may include or be in electronic communication with a wireless transmission system. The wireless transmission system may receive information from the at least one strain gauge and convert the information into digital information that may be wireless transmitted to the robotic surgical system.

As disclosed herein, a device quantifying an amount of force applied to a joint during ligament laxity data collection may provide more consistent inputs to a robotic surgical system. Standardizing this input may reduce the amount of intraoperative surgeon interaction with planning software for a robotic surgical system. As such, a more efficient procedure including less variability in surgical outcomes may result.

In addition, the teachings of the present disclosure may decrease the likelihood that a tibial poly insert or other total knee arthroplasty component will need to be recut or resized after implantation, because of the increase in standardization for data collection. Over-stressing or under-stressing the joint during the ligament laxity data collection process may falsely indicate a very tight or very loose joint, which may result in an overcut or undercut during a bone resection.

Furthermore, the teachings of the present disclosure may reduce a surgeon's learning curve when adopting a robotic surgical system. In particular, the devices and methods disclosed herein may enable more productive guidance to be provided to a user regarding whether an amount of force being applied during ligament laxity data collection.

Figure 21:
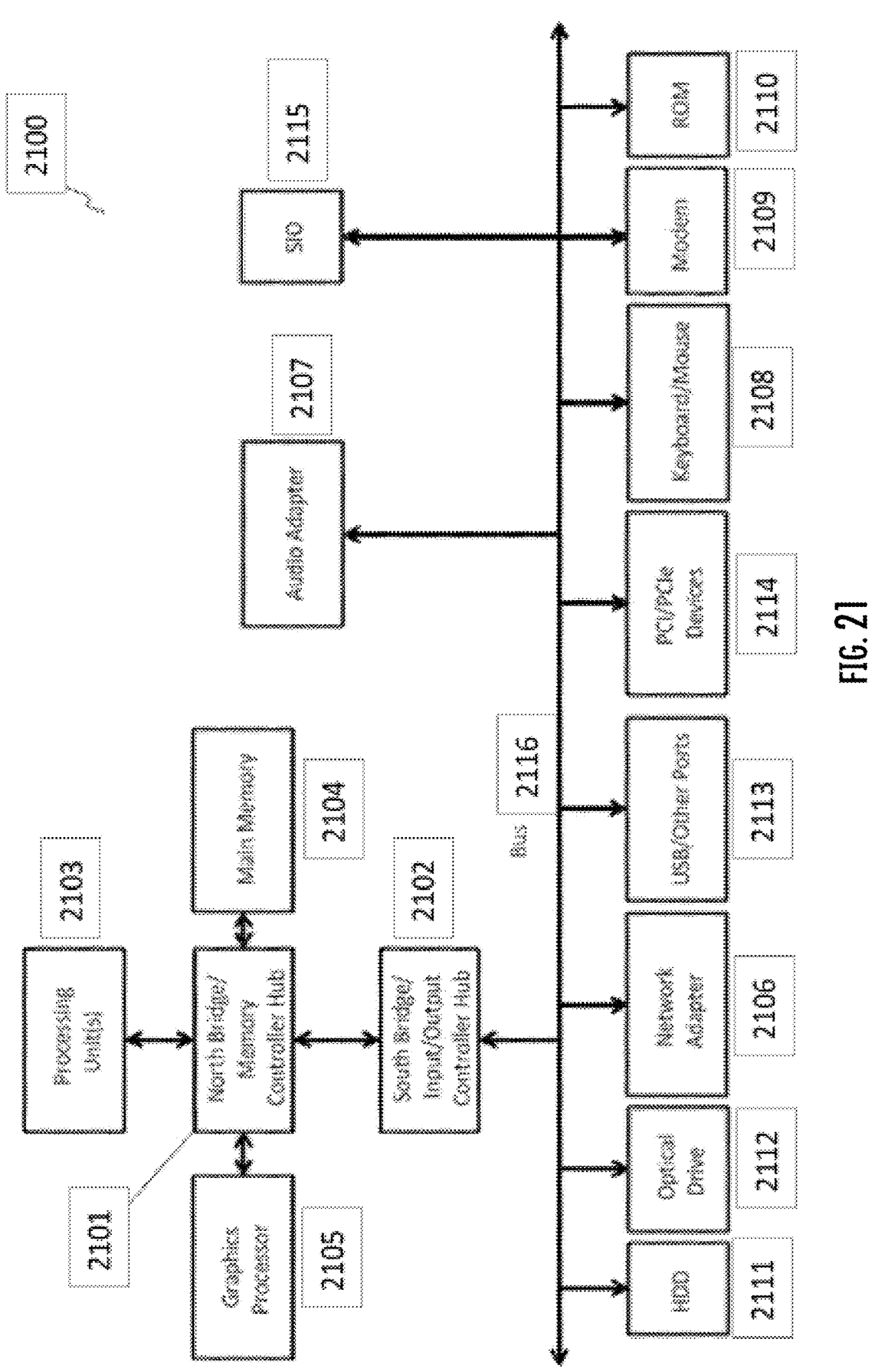
FIG. 21 depicts an illustrative block diagram of a data processing system in which aspects of the illustrative embodiments are implemented.

FIG. 21 illustrates a block diagram of an illustrative data processing system 2100 in which aspects of the illustrative embodiments are implemented. The data processing system 2100 is an example of a computer, such as a server or client, in which computer usable code or instructions implementing the process for illustrative embodiments of the present invention are located. In some embodiments, the data processing system 2100 may be a server computing device. For example, data processing system 2100 can be implemented in a server or another similar computing device operably connected to a surgical system 100 as described above. The data processing system 2100 can be configured to, for example, transmit and receive information related to a patient and/or a related surgical plan with the surgical system 100.

In the depicted example, data processing system 2100 can employ a hub architecture including a north bridge and memory controller hub (NB/MCH) 2101 and south bridge and input/output (I/O) controller hub (SB/ICH) 2102. Processing unit 2103, main memory 2104, and graphics processor 2105 can be connected to the NB/MCH 2101. Graphics processor 2105 can be connected to the NB/MCH 2101 through, for example, an accelerated graphics port (AGP).

In the depicted example, a network adapter 2106 connects to the SB/ICH 2102. An audio adapter 2107, keyboard and mouse adapter 2108, modem 2109, read only memory (ROM) 2110, hard disk drive (HDD) 2111, optical drive (e.g., CD or DVD) 2112, universal serial bus (USB) ports and other communication ports 2113, and PCI/PCIe devices 2114 may connect to the SB/ICH 2102 through bus system 2116. PCI/PCIe devices 2114 may include Ethernet adapters, add-in cards, and PC cards for notebook computers. ROM 2110 may be, for example, a flash basic input/output system (BIOS). The HDD 2111 and optical drive 2112 can use an integrated drive electronics (IDE) or serial advanced technology attachment (SATA) interface. A super I/O (SIO) device 2115 can be connected to the SB/ICH 2102.

An operating system can run on the processing unit 2103. The operating system can coordinate and provide control of various components within the data processing system 2100. As a client, the operating system can be a commercially available operating system. An object-oriented programming system, such as the Java™ programming system, may run in conjunction with the operating system and provide calls to the operating system from the object-oriented programs or applications executing on the data processing system 2100. As a server, the data processing system 2100 can be an IBM'R; eServer™ System pR running the Advanced Interactive Executive operating system or the Linux operating system. The data processing system 2100 can be a symmetric multiprocessor (SMP) system that can include a plurality of processors in the processing unit 2103. Alternatively, a single processor system may be employed.

Instructions for the operating system, the object-oriented programming system, and applications or programs are located on storage devices, such as the HDD 2111, and are loaded into the main memory 2104 for execution by the processing unit 2103. The processes for embodiments described herein can be performed by the processing unit 2103 using computer usable program code, which can be located in a memory such as, for example, main memory 2104, ROM 2110, or in one or more peripheral devices.

A bus system 2116 can be comprised of one or more busses. The bus system 2116 can be implemented using any type of communication fabric or architecture that can provide for a transfer of data between different components or devices attached to the fabric or architecture. A communication unit such as the modem 2109 or the network adapter 2106 can include one or more devices that can be used to transmit and receive data.

Those of ordinary skill in the art will appreciate that the hardware depicted in FIG. 21 may vary depending on the implementation. Other internal hardware or peripheral devices, such as flash memory, equivalent non-volatile memory, or optical disk drives may be used in addition to or in place of the hardware depicted. Moreover, the data processing system 2100 can take the form of any of a number of different data processing systems, including but not limited to, client computing devices, server computing devices, tablet computers, laptop computers, telephone or other communication devices, personal digital assistants, and the like. Essentially, data processing system 2100 can be any known or later developed data processing system without architectural limitation.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to." "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world: through inadvertent error in these procedures: through differences in the manufacture, source, or purity of compositions or reagents; and the like. Typically, the term "about" as used herein means greater or lesser than the value or range of values stated by 1/10 of the stated values, e.g., +10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A device for measuring one or more forces applied to a joint during a surgical procedure, the device comprising:
   a body having a top portion, the body having a first elastic modulus;
   an insertion tool operatively coupled to the top portion of the body, the insertion tool having a second elastic modulus less than the first elastic modulus, wherein the insertion tool has at least one prong sized and shaped to be received between a femoral condyle and a tibial condyle of the joint, and wherein the at least one prong is configured to deflect with respect to the body by concentrating the one or more forces applied to the insertion tool at a predetermined location of the insertion tool; and
   a force indicator module comprising:
      a first optical tracking array disposed on the body; and
      a second optical tracking array that is disposed on the at least one prong of the insertion tool and is positioned and configured to remain exposed outside of the joint while the at least one prong is between the femoral condyle and the tibial condyle;
   wherein the force indicator module is configured such that the one or more forces can be determined based on a relative position between the first and second optical tracking arrays.

2. The device of claim 1, wherein the force indicator module is configured to record a measurement selected from the group consisting of a minimum force measurement, a maximum force measurement, and combinations thereof.

3. The device of claim 2, wherein the measurement is recorded based on one or more received triggers.

4. The device of claim 3, wherein the one or more received triggers are selected from the group consisting of: a user input, a user gesture, a user voice, temporal components, a determined force being applied, a rotational force being applied, and a sensor input.

5. The device of claim 1, wherein:
   the insertion tool further comprises a tongue component having a first long side, a second long side, a first short side, and a second short side, wherein the tongue component is connected to the body solely on the first short side;

the tongue component is parallel to the body when no force is applied to the body; and the tongue component is configured to be displaced from the body at an angle when a force is applied to a portion of the body.

6. The device of claim 5, wherein the angle is proportional to the force applied to the portion of the body.

7. The device of claim 1, wherein the insertion tool is a Hohmann-type retractor.

8. A device for measuring a force applied to a joint during a surgical procedure, the device comprising:

a linear body comprising a handle portion having a first elastic modulus and a tip portion having at least one prong sized and shaped to be received between a femoral condyle and a tibial condyle of the joint and apply the force against one of the femoral condyle and the tibial condyle, the linear body comprising a flexible portion, wherein the flexible portion has a moment of inertia and a second elastic modulus less than the first elastic modulus;

a first optical tracking array operatively connected to the linear body near the handle portion; and a second optical tracking array operatively connected to the linear body near the tip portion;

wherein the first and second optical tracking arrays create a measurable vector detectable by a tracking system while the at least one prong is received between the femoral condyle and the tibial condyle;

wherein the measurable vector is altered when the flexible portion receives the force and deflects by concentrating the force at a predetermined location of the flexible portion; and wherein a magnitude and a direction of the force can be determined based on an amount of deflection.

9. The device of claim 8, wherein;

the first optical tracking array comprises at least one of an active tracker, a passive tracker, an infrared camera system, a stereo camera system, an active LED tracker, a retroreflective marker tracker, and a video tracker; and the second optical tracking array comprises at least one of an active tracker, a passive tracker, an infrared camera system, a stereo camera system, an active LED tracker, a retroreflective marker tracker, and a video tracker.

10. The device of claim 8, wherein the measurable vector comprises an angle that is proportional to the force applied to the flexible portion of the linear body.

11. The device of claim 8, wherein the tip portion comprises at least one of a z-type retractor and a Hohmann-type retractor.

12. The device of claim 8, further comprising a robotic surgical system including the tracking system, which is configured to determine the magnitude and the direction of the force based on the amount of deflection.

13. The device of claim 12, wherein the amount of deflection is recorded based on at least one of a user input, a user gesture, a user voice, temporal components, a determined force being applied, a rotational force being applied, and a sensor input.

14. A system for measuring one or more forces applied to a joint during a surgical procedure, the system comprising:

a device comprising:

a body having a top portion, the body having a first elastic modulus; and an insertion tool operatively coupled to the top portion of the body, the insertion tool having a second elastic modulus less than the first elastic modulus, wherein the insertion tool has at least one prong sized and shaped to be received between a femoral condyle and a tibial condyle of the joint, and wherein the at least one prong is configured to deflect with respect to the body based on the one or more forces applied to the insertion tool at a predetermined location of the insertion tool;

a first optical tracking array disposed on the body;

a second optical tracking array that is disposed on the at least one prong of the insertion tool and is positioned and configured to remain exposed outside of the joint while the at least one prong is between the femoral condyle and the tibial condyle; and a robotic surgical system configured determine a relative position between the first and second optical tracking arrays and, from the relative position, determine the one or more forces applied to the insertion tool.

15. The device of claim 1, wherein a position of the first optical tracking array changes with respect to a position of the second optical tracking array when the at least one prong deflects based on the one or more forces.

* * * * *